(12) United States Patent
Raines et al.

(10) Patent No.: US 9,732,101 B2
(45) Date of Patent: Aug. 15, 2017

(54) BIOREVERSIBLE BORONATES FOR DELIVERY OF MOLECULES INTO CELLS

(71) Applicant: WISCONSIN ALUMNI RESEARCH FOUNDATION, Madison, WI (US)

(72) Inventors: Ronald T. Raines, Madison, WI (US); Thomas P. Smith, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/809,288

(22) Filed: Jul. 27, 2015

(65) Prior Publication Data
US 2016/0024122 A1 Jan. 28, 2016

Related U.S. Application Data

(63) Continuation-in-part of application No. 13/745,737, filed on Jan. 18, 2013, now Pat. No. 9,234,048.

(60) Provisional application No. 62/029,391, filed on Jul. 25, 2014, provisional application No. 61/588,120, filed on Jan. 18, 2012.

(51) Int. Cl.
| C07F 5/02 | (2006.01) |
| C12N 9/96 | (2006.01) |
| C12N 9/22 | (2006.01) |
| C12N 11/00 | (2006.01) |
| A61K 47/48 | (2006.01) |

(52) U.S. Cl.
CPC ........ *C07F 5/025* (2013.01); *A61K 47/48061* (2013.01); *C12N 9/22* (2013.01); *C12N 11/00* (2013.01); *C12Y 301/27005* (2013.01); *C07K 2319/43* (2013.01); *C07K 2319/60* (2013.01)

(58) Field of Classification Search
CPC ....................................................... C07F 5/025
See application file for complete search history.

(56) References Cited

U.S. PATENT DOCUMENTS

| 4,499,082 A | 2/1985 | Shenvi et al. |
| 5,384,410 A | 1/1995 | Kettner |
| 5,594,111 A | 1/1997 | Stolowitz |
| 5,594,151 A | 1/1997 | Stolowitz |
| 5,623,055 A | 4/1997 | Stolowitz |
| 5,744,627 A | 4/1998 | Stowolitz et al. |
| 5,777,148 A | 7/1998 | Stowolitz et al. |
| 5,837,878 A | 11/1998 | Stolowitz et al. |
| 5,846,741 A | 12/1998 | Griffiths et al. |
| 5,859,231 A | 1/1999 | Shaw et al. |
| 6,013,783 A | 1/2000 | Kaiser et al. |
| 6,018,020 A | 1/2000 | Attwood et al. |
| 6,075,126 A | 6/2000 | Stolowitz et al. |
| 6,124,471 A | 9/2000 | Stolowitz et al. |
| 6,156,884 A | 12/2000 | Ahlem et al. |
| 6,350,527 B1 | 2/2002 | Hubbell et al. |
| 6,462,179 B1 | 10/2002 | Stolowitz et al. |
| 6,465,433 B1 | 10/2002 | Adams et al. |
| 6,548,668 B2 | 4/2003 | Adams et al. |
| 6,596,267 B1 | 7/2003 | Hubbell et al. |
| 6,630,557 B2 | 10/2003 | Zhu et al. |
| 6,919,382 B2 | 7/2005 | Hall |
| 6,972,320 B2 | 12/2005 | Raines et al. |
| 7,256,259 B2 | 8/2007 | Raines et al. |
| 7,317,129 B2 | 1/2008 | Raines et al. |
| 7,442,764 B2 | 10/2008 | Rozema et al. |
| 7,842,823 B2 | 11/2010 | Chang |
| 8,637,490 B2 | 1/2014 | Peng et al. |
| 2003/0044840 A1 | 3/2003 | Hall |
| 2003/0059399 A1 | 3/2003 | Holmes-Farley et al. |
| 2007/0141105 A1 | 6/2007 | Stein et al. |
| 2007/0213277 A1 | 9/2007 | Rothbard et al. |
| 2007/0265226 A1 | 11/2007 | Lee et al. |
| 2008/0166361 A1 | 7/2008 | Patel |
| 2009/0148887 A1 | 6/2009 | Brustad et al. |
| 2009/0325903 A1 | 12/2009 | Elliott et al. |
| 2010/0029545 A1 | 2/2010 | Sumerlin et al. |
| 2010/0048866 A1 | 2/2010 | Raines et al. |
| 2010/0267981 A1 | 10/2010 | Baker et al. |
| 2011/0059040 A1 | 3/2011 | Kiser et al. |
| 2011/0201670 A1 | 8/2011 | Mor et al. |
| 2011/0275585 A1 | 11/2011 | Brahmbhatt et al. |
| 2013/0011448 A1 | 1/2013 | Tedebark |
| 2013/0196433 A1 | 8/2013 | Raines et al. |
| 2016/0083706 A1 | 3/2016 | Raines et al. |

FOREIGN PATENT DOCUMENTS

| EP | 1 165 569 | 8/2005 |
| JP | H07-247292 | 9/1995 |
| WO | WO 95/20591 | 8/1995 |
| WO | WO 2010/039088 | 4/2010 |
| WO | WO 2012/113846 | 8/2012 |

OTHER PUBLICATIONS

Adamczyk-Wozniak et al. (Oct. 15, 2009) "Benzoxaboroles-Old compounds with new applications," *J. Organomet. Chem.* 694(22):3533-3541.
Bérubé et al. (2008) "Benzoboroxoles as Efficient Glycopyranoside-Binding Agents in Physiological Conditions: Structure and Selectivity of Complex Formation," *J. Org. Chem.* 73:6471-6479.
Bonné et al. (Nov. 13, 2009) "Boronic Acid Dendrimer Receptor Modified Nanofibrillar Cellulose Membranes," *J. Mater. Chem.* 20:588-594.
Cambre et al. (Sep. 29, 2011) "Biomedical Applications of Boronic Acid Polymers," *Polymer.* 52:4631-4643.
Djanashvili et al. (2005) "Molecular Recognition of Sialic Acid End Groups by Phenylboronates," *Chem. Eur. J.* 11:4010-4018.
Dowlut et al. (2006) "An Improved Class of Sugar-Binding Boronic Acids, Soluble and Capable of Complexing Glycosides in Neutral Water," *J. Am. Chem. Soc.* 128:4226-4227.
Ellis et al. (Feb. 3, 2012) "Boronate-Mediated Biologic Delivery," *J. Am. Chem. Soc.* 134:3631-3634.
International Search Report with Written Opinion corresponding to International Patent Application No. PCT/US2013/22323, mailed Apr. 8, 2013.

(Continued)

*Primary Examiner* — Rosalynd Keys
(74) *Attorney, Agent, or Firm* — Lathrop & Gage LLP

(57) ABSTRACT

Methods for enhancing cellular uptake of cargo molecules by boronating the cargo molecule, particularly with one or more phenylboronic acid groups. Boronation reagents for reversible boronation of cargo molecules, particularly, cargo molecules having one or more amino groups are provided.

27 Claims, 28 Drawing Sheets

(56) References Cited

OTHER PUBLICATIONS

Ivanov et al. (2006) "Interaction of sugars, polysaccharides and cells with boronate-containing copolymers: from solution to polymer brushes," *J. Mol. Recognit.* 19:322-331.
James et al. (2006) "Complexation of Boronic Acids with Saccharides," In; Ch.3 *Boronic Acids in Saccharide Recognition. Royal Society of Chemistry.* Cambridge, United Kingdom. pp. 13-33.
Jay et al. (Dec. 16, 2009) "Multivalent Benzoboroxole Functionalized Polymers as gp120 Glycan Targeted Microbicide Entry Inhibitors," *Mol. Pharm.* 7:116-129.
Mahalingham et al. (Aug. 31, 2011) "Activity and Safety of Synthetic Lectins Based on Benzoboroxole-Functionalized Polymers for Inhibition of HIV Entry," *Mol. Pharm.* 8:2465-2475.
Matsumoto et al. (Aug. 10, 2009) "Noninvasive Sialic Acid Detection at Cell Membrane by Using Phenylboronic Acid Modified Self-Assembled Monolayer Gold Electrode," *J. Am. Chem. Soc.* 131:12022-12023.
Matsumoto et al. (Jun. 23, 2010) "Assessment of Tumor Metastasis by the Direct Determination of Cell-Membrane Sialic Acid Expression," *Angew. Chem. Int. Ed.* 49:5494-5497.
Mothana et al. (Feb. 9, 2010) "Multistep Phase-Switch Synthesis by Using Liquid-Liquid Partitioning of Boronic Acids: Productive Tags with an Expanded Repertoire of Compatible Reactions," *Angew. Chem. Int. Ed.* 49:2883-2887.
Otsuka et al. (2003) "Anomalous Binding Profile of Phenylboronic Acid with N-Acetylneuraminic Acid (Neu5Ac) in Aqueous Solution with Varying pH," *J. Am. Chem. Soc.* 125:3493-3502.
Pal et al. (Jan. 18, 2010) "Design, Synthesis, and Screening of a Library of Peptidyl Bis(Boroxoles) as Oligosaccharide Receptors in Water: Identification of a Receptor for the Tumor Marker TF-Antigen Disaccharide," *Angew. Chem. Int. Ed.* 49:14921495.
Peng et al. (Jul. 13, 2010) "Enhanced gene transfection capability of polyethylenimine by incorporating boronic acid groups," *Chem. Commun.* 46:58885890.
Polsky et al. (2008) "Electrically Addressable Cell Immobilization Using Phenylboronic Acid Diazonium Salts," *Angew. Chem. Int. Ed.* 120:2671-2674.
Santos et al. (2007) "Michael Acceptors as Cysteine Protease Inhibitors," *Mini. Rev. Med. Chem.* 7(10):1040-1050.
Snyder et al. (1958) "Synthesis of Aromatic Boronic Acids—Aldehydo Boronic Acids and a Boronic Acid Analog of Tyrosine," *J. Am. Chem. Soc.* 80(4):835-838.
Springsteen et al. (2002) "A detailed examination of boronic acid—diol complexation," *Tetrahedron.* 58:5291-5300.
Tomsho et al. (Oct. 19, 2011) "Ring Structure and Aromatic Substituent Effects on the pKa of the Benzoxaborole Pharmacophore," *ACS Med. Chem. Letts.* 3(1):48-52.
Chemical Abstract 1958: 82427 of Torssell (1957) "Arylboronic acids I," Arkiv foer Kemi. 10:473-482.—Abstract Only.
Chemical Abstract 1958: 82428 of Torssell (1957) "Arylboronic acids II," Arkiv foer Kemi. 10:497-505.—Abstract Only.
Chemical Abstract 1958: 82429 of Torssell (1957) "Arylboronic acids III. Bromination of tolylboronic acids according to Wolf-Ziegler," Arkiv foer Kemi. 10:507-511.—Abstract Only.
Chemical Abstract 1958: 82430 of Torssell (1957) "Arylboronic acids IV. Nitration of several arylboronic acids and characteristics of the boron-carbon bond," Arkiv foer Kemi. 10:513-521.—Abstract Only.
Chemical Abstracts 1958: 82432 of Torssell (1957) "Arylboronic acids. A review," Svensk Kemisk Tidskrift. 69:34-44.—Abstract Only.
Chemical Abstract 1958: 98219 of Torssell (1957) "Arylboronic acids. V. Effects of arylboronic acids on microorganisms and enzymes," Arkiv foer Kemi. 10:529-540.—Abstract Only.
Chemical Abstract 1958: 82431 of Torssell (1957) "Arylboronic acids. VII. Complex formation between phenylboronic acid and fructose," Arkiv foer Kemie. 10:541-547.—Abstract Only.
Westmark et al. (1996) "Boronic acids facilitate the transport of ribonucleosides through lipid bilayers," *J. Pharm. Sci.* 85:266-269.
Westmark et al. (1996) "Selective Monosaccharide Transport through Lipid Bilayers Using Boronic Acid Carriers," *J. Am. Chem. Soc.* 118:11093-11100.
Yan et al. (2005) "A novel redox-sensitive protecting group for boronic acids, MPMP-diol," *Tetrahedron Letters.* 46:8503-8505.
Yanagie et al. (2008) "Application of Drug Delivery System to Boron Neutron Capture Therapy for Cancer," *Expert Opin. Drug Deliv.* 5(4):427-443.
Yang et al. (2004) "The First Fluorescent Diboronic Acid Sensor Specific for Hepatocellular Carcinoma Cells Expressing Sialyl Lewis X," *Chem. Biol.* 11:439-448.
Zhong et al. (Mar. 4, 2010) "A Reusable Interface Constructed by 3-Aminophenylboronic Acid-Functionalized Multiwalled Carbon Nanotubes for Cell Capture, Release, and Cytosensing," *Adv. Funct. Mater.* 20:992-999.
Cal et al. (2014) "Targeting cancer cells with folic acid-iminoboronate fluorescent conjugates," *Chem. Comm.* 50:5261-5263.
Jia et al. (Mar. 31, 2014) "A boronate-linked linear-hyperbranched polymeric nanovehicle for pH-dependent tumor-targeted drug delivery," *Biomaterials.* 35:5240-5249 (Abstract Only).
Levine et al. (May 30, 2012) "Trimethyl lock: A trigger for molecular release in chemistry, biology, and pharmacology," *Chemical Science.* 3(8):2412-2420.
Li et al. (Jan. 17, 2012) "Well-defined, reversible boronate cross-linked nanocarriers for targeted drug delivery in response to acidic pH values and cis-diols," Angew. Chem. Int. Ed. 51:2864-2869.
Ma et al. (Oct. 11, 2013) "Phenylboronic acid-based glucose-responsive polymeric nanoparticles: synthesis and applications in drug delivery," *Polym. Chem.* 5:1503-1518. (Abstract Only).
McGrath et al. (Oct. 1, 2014) "Diazo compounds for the bioreversible esterification of proteins," *Chem. Sci.* 6:752-755.
Wang et al. (Apr. 7, 2015) "Development of phenylboronic acid-functionalized nanoparticles for emodin delivery," J. Mater. Chem. B. 3:3840-3847.
Wang et al. (Feb. 28, 2013) "Size- and pathotropism-driven targeting and washout-resistant effects of boronic acid-rich protein nanoparticles for liver cancer regression," *J. Control. Release.* 168:1-9. (Abstract Only).
Wang et al. (Aug. 6, 2014) "Fabrication of boronic acid-functionalized nanoparticles via boronic acid-diol complexation for drug delivery," *RSC Adv.* 4:53877-53884.
Yang et al. (May 27, 2014) "A pH-responsive drug nanovehicle constructed by reversible attachment of cholesterol to PEGylated poly(L-lysine) via catechol-boronic acid ester formation," *Acta. Biomater.* 10:3686-3695. (Abstract Only).
Zhao et al. (2009) "Mesoporous silica nanoparticle-based double drug delivery system for glucose-responsive controlled release of Insulin and Cyclic AMP," *J. Am. Chem. Soc.* 131:8398-8400.
Zhao et al. (Aug. 21, 2014) "Boronic acid shell-crosslinked dextran-b-PLA micelles for acid-responsive drug delivery," *Macromol. Biosci.* 14:1609-1618.

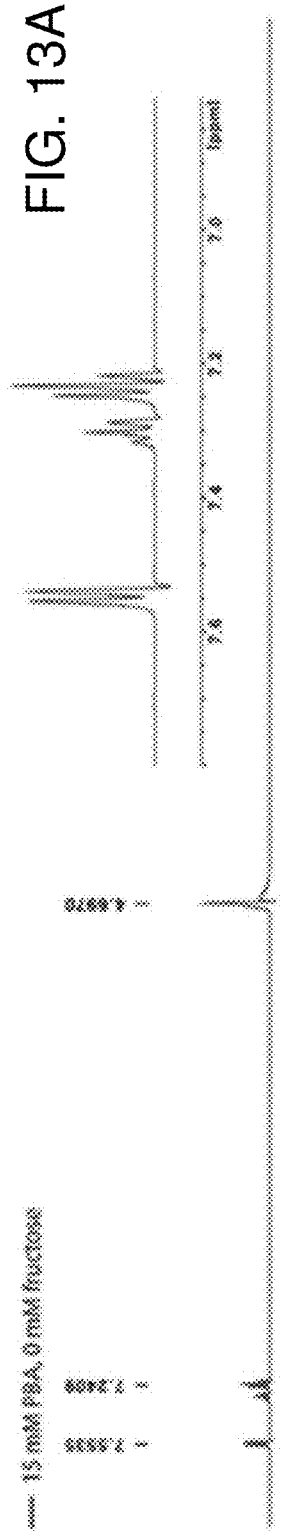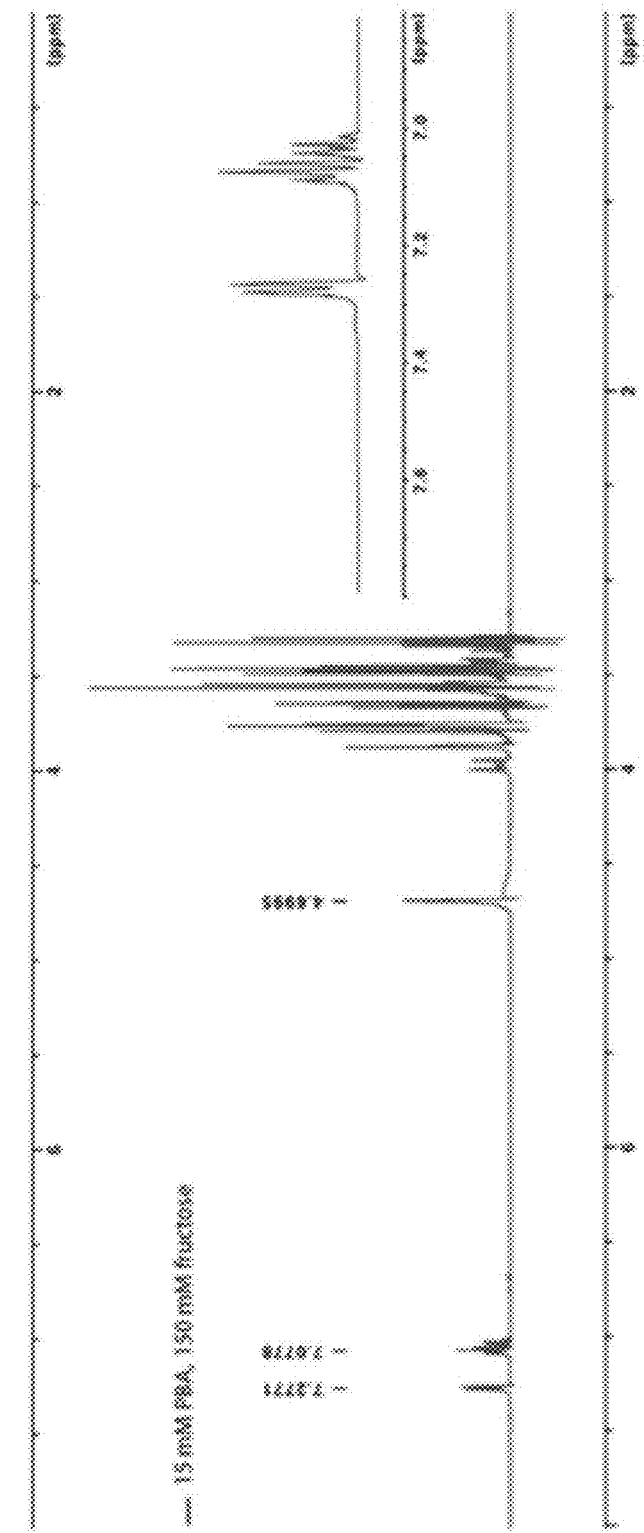
FIG. 13A
FIG. 13B

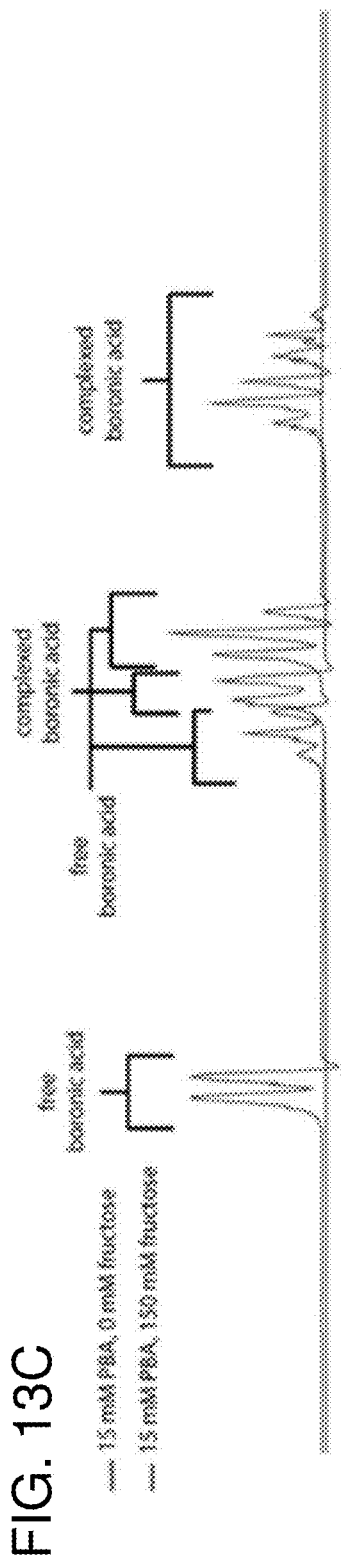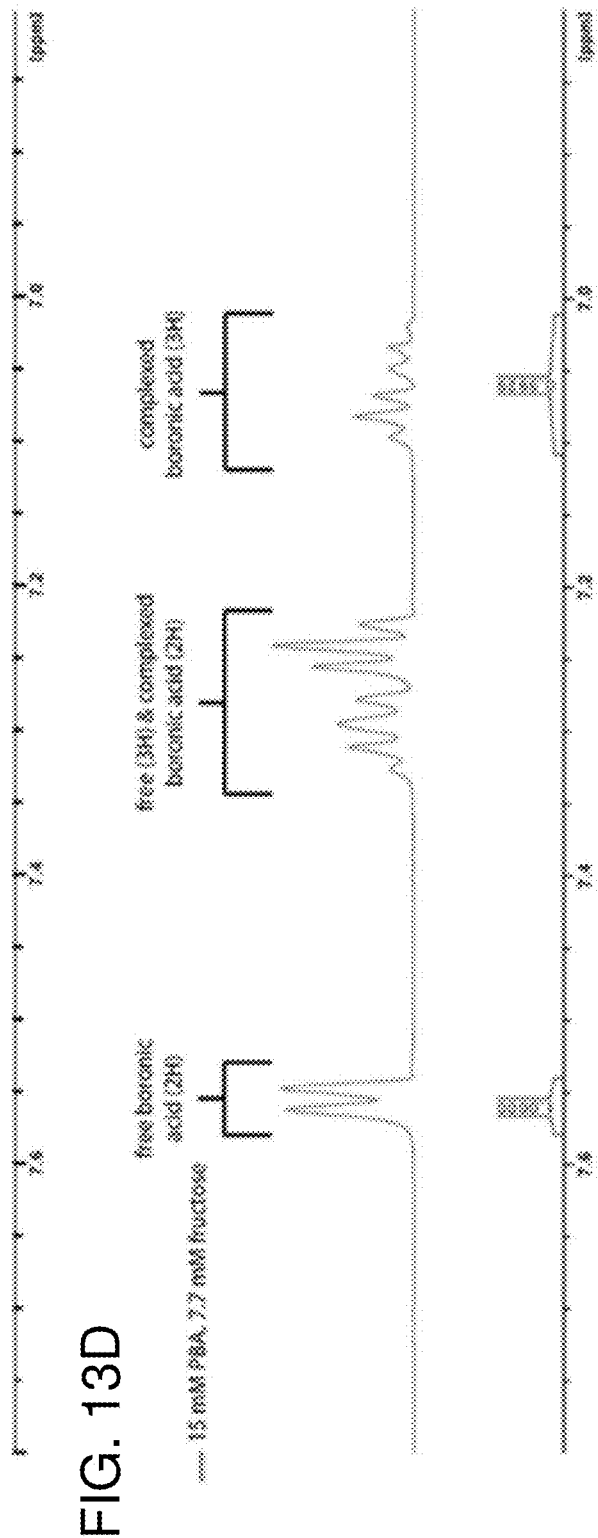
FIG. 13C
FIG. 13D

US 9,732,101 B2

BIOREVERSIBLE BORONATES FOR DELIVERY OF MOLECULES INTO CELLS

CROSS-REFERENCE TO RELATED APPLICATIONS

This application claims the benefit of U.S. provisional application 62/029,391, filed Jul. 25, 2014 which is incorporated by reference herein in its entirety. This application is also a continuation-in-part of U.S. application 113/745,737, filed Jan. 18, 2013, which in turn claims the benefit of U.S. provisional application 61/588,120, filed Jan. 18, 2012.

STATEMENT REGARDING U.S. GOVERNMENT FUNDING

This invention was made with government support under GM044783 awarded by the National Institutes of Health. The government has certain rights in the invention.

BACKGROUND OF THE INVENTION

The utility of many biologic drugs is limited by inefficient cellular delivery [1]. Additional problems include biological instability, poor biodegradability or immunogenicity [1e]. Previous efforts to overcome this limitation have focused largely on the use of cationic domains, including peptidic cationic species (e.g., HIV-TAT, penetratin, and nonaarginine and more generally cell penetrating peptides (CPP)) or non-peptidic cationic species (e.g., PAMAM dendrimers and polyethylimine), to enhance the attraction between a chemotherapeutic agent and the anionic cell surface [2]. Natural ligands (e.g., folic acid, substance P, and the RGD tripeptide) have also been used to facilitate cellular delivery by targeting agents to specific cell-surface receptors [3]. Such methods have been applied, for example, to delivery of peptides, proteins, nucleic acids and analogs thereof, reporters and labels, various pharmaceuticals and drugs and various small molecules as well as particles. Although some of these methods have had some success, there remains a need in the art for additional delivery strategies.

The cell surface of many prokaryotic and eukaryotic cells is coated with a dense forest of polysaccharides known as the glycocalyx [4]. Targeting of therapeutic agents to the glycocalyx might enhance their cellular delivery, as has been demonstrated with lectin conjugates [5]. Boronic acids readily form boronate esters with the 1,2- and 1,3-diols of saccharides [6], including those in the glycocalyx [7]. In addition, boronate groups are compatible with human physiology, appearing in chemotherapeutic agents and other remedies [8]. The present invention relates to the use of pendant boronic acids to mediate the delivery of a cargo molecule into mammalian cells.

Boronic acids have been employed in the development of sensors for glycans [6] and in the development of boron neutron capture therapies for cancer treatment [24]. Boronic acids have also been reported as useful in glucose sensors for the controlled release of insulin [8d]. Certain diboronic acid compounds have been reported useful as fluorescent sensors for certain cancer cells which express sialyl Lewis X [7b]. Boronic acids have been reported useful in drug delivery applications, for example, to transport nucleotides and monosaccharides across liposomal bilayers [8a, 25], for labeling of liposomes for increased affinity for erythrocyte ghosts [7a] and for enhancement of PEI-DNA complexation for transfection reagents [8e]. Phenylboronic acid-(PBA-) functionalized polymers [26, 27] and nanoparticle complexes [28, 29, 30] have been loaded with small-molecule chemotherapeutic agents. These approaches employ large, complex assemblies that use PBA as a reactive functionality [31] or in the architecture of the delivery complex 32-36]. PBA has also been expanded to deliver protein cargos under conditions of oxidative stress [34] and to deliver DNA. [8e, 37]

U.S. Pat. No. 4,499,082 reports certain alpha-aminoboronic acid peptides as reversible inhibitors of proteolytic enzymes. U.S. Pat. No. 6,018,020 relates to boronated amino acid derivatives which are viral proteinase inhibitors. U.S. Pat. Nos. 6,465,433; 6,548,668; and U.S. published application 2009/0325903 report certain amino acid and peptidyl boronic acids as inhibitors of proteasome function and more specifically as inhibitors of HIV replication in an animal. In each of these references, a carboxylic acid group of an amino acid is replaced with a boronic acid group ($-B(OH)_2$) or an ester thereof. Each of these references is incorporated by reference herein in its entirety for its description of amino acids and peptidyl boronic acids and any description therein of methods of synthesis thereof.

U.S. published application 20110059040 relates to methods for inhibiting the activity of a virus or bacterium by contacting the virus or bacterium with a polymer functionalized with at least one boronic acid moiety, including one or more substituted or unsubstituted arylboronic acids, particularly phenylboronic acids. Certain multivalent benzoboroxole functionalized polymers have been reported to inhibit microbicide entry [8b].

U.S. Pat. Nos. 5,594,111; 5,594,151; 5,623,055; 5,777,148; 5,744,627; 5,837,878; and 6,156,884 relate to phenylboronic acid complexing reagents and complexes formed with such complexing reagents which are reported to be useful for preparation of bioconjugates. Similar reports of phenyldiboronic acid complexing reagents and complexes formed therewith are found in U.S. Pat. Nos. 6,075,126; 6,124,471; 6,462,179 and 6,630,577. Each of these references is incorporated by reference herein in its entirety for descriptions of phenylboronic acid compounds and phenyldiboronic acid compounds and methods of synthesis thereof.

The physical properties including sugar binding properties of certain benzoboroxoles and benzoxaborins have been studied [13, 22, 27]. Syntheses of certain benzoboroxoles have been reported [30-36]. A review of applications of benzoboroxoles has been provided [28]. These references are incorporated by reference herein for methods of synthesis and sugar binding properties of benzoboroxoles.

The design, synthesis and screening of a library of peptidyl bis(boroxoles) as receptors for the tumor marker TF-Antigen disaccharide in water has been reported [22]. The library components contained a free amine, a certain PEG linker, two diaminoproponic acids residues to which benzoboroxole groups were attached separated by a central amino acid (where the library components were randomized with 20 selected natural and non-natural amino acids) and a capping group (where the library components were randomized with 20 selected capping groups). This reference is incorporated by reference herein for its description of the library species and methods of synthesis of the library species. Any peptidyl bis(boroxoles) noted in this reference can optionally be excluded from the claims herein.

Gold electrodes activated by phenylboronic acid diazonium salts are reported for the reversible immobilization of eukaryotic cells [7c]. An electrochemical cell sensor for the determination of K562 leukemia cells using 3-aminophenylboronic acid (APBA)-functionalized multiwalled carbon nanotubes (MWCNTs) films is reported [7e]. K562 leukemia cells are reported to be bound to the APBA-functionalized MWCNTs film via boronic acid groups. This reference is incorporated by reference herein in its entirety for descriptions of phenylboronic acid diazonium salts and synthesis thereof.

SUMMARY OF THE INVENTION

The present invention relates to methods for enhancing cellular uptake of a cargo molecule by boronating the cargo molecule, particularly with one or more phenylboronic acid groups. In a specific embodiment, cellular uptake includes at least partial uptake into the cytosol. Cellular uptake may be in vivo or in vitro. The method of the invention is generally useful for the delivery of any desired molecule into a cell and specifically includes nucleic acids and analogs thereof; nucleotides and analogs thereof; peptides and proteins; drugs (e.g., anticancer drugs, alkylating agents, antimetabolite, cytotoxic agents; antibiotics, and the like); reporter molecules or labels (e.g., fluorescent labels, isotopic labels, imaging agents, quantum dots, and the like).

In specific embodiments, the cargo molecule carries an amine functionality which can react with a phenylboronate reagent to facilitate attachment of the phenylboroante to the cargo molecule. In an embodiment, the phenylboronate is attached to the cargo molecule by formation of one or more covalent bonds. In a specific embodiment, the cargo comprises a quantum dot carrying amine functionality. The cargo molecule can include combinations of the species listed above, wherein the species are bonded to each other, particularly where the species are covalently bonded to each other. For example, a cargo molecule may combine a peptide, such as a CPP or a nuclear localizing signal with a nucleic acid, or combine a fluorescent, isotopic or other label with a nucleic acid and or peptide. In a specific embodiment, the cargo is or comprises a molecule which affects, regulates or modulates gene expression in the cell, including a molecule which inhibits or decreases gene expression or a molecule which initiates or enhances gene expression. In a specific embodiment, the cargo molecule is a peptide or a protein, for example, an enzyme. In a specific embodiment, the cargo molecule is a fluorescent protein.

In one embodiment, the boronating method relates to forming one or more bonds between the cargo molecule and one or more phenylboronic acid groups to boronate the cargo molecule. In this embodiment, one or more phenylboronic acids substituted to contain a reactive group, as described herein, are reacted with one or more reactive groups of the cargo molecule. More specifically, the one or more bonds formed may be covalent bonds formed between one or more reactive groups on the cargo molecule and a reactive group on the one or more phenylboronic acid compounds. The reaction of these reactive groups results in the formation of a linking moiety between the phenylboronate group and the cargo molecule. The linking moiety comprises the covalent bond or bonds newly formed by reaction, can also comprise residual moieties from the reactive groups and can contain one or more selected spacer moieties. For example, the reactive groups on the cargo molecule or the reactive groups on the phenylboronate compound can themselves be optionally attached to the cargo molecule or the phenylboronate group, respectively, via a spacer moiety. In this case the linking moiety that results from reaction of the reactive groups contains any such spacing moieties in the starting cargo molecule or phenylboronate compounds, bonds that are formed by reaction of reactive groups and any residue of the reactive groups. In a specific embodiment, the linking moiety between the phenylboronate and the cargo molecule also contains a label which functions to label the cargo molecule.

In a specific embodiment, the phenylboronate groups are bonded to the cargo molecule via linking moieties that can be selectively cleaved. In a more specific embodiment, phenylboronate groups can be cleaved from the cargo molecule after the boronated cargo molecule is introduced into the cell, particularly by cleavage of a lining moiety. In a specific embodiment, the cleavable linker contains a latent reactive group, which is selectively activated to cleave the linker and thereby cleave the phenylboronate(s) from the cargo molecule. In other specific embodiments, the linker is cleaved via selective activation of a latent reactive group on the phenyl boronate which functions to cleave the linker molecule and thereby cleave the phenylboronate(s) from the cargo molecule. In a specific embodiment, the phenylboronates are esterase releasable, e.g., the linker between the phenylboronate and the cargo molecule is cleavable by esterase action. In more specific embodiments, the linker is cleavable by a trimethyl lock mechanism. In other specific embodiments, the linker is a coumarin-based esterase releasable linker moiety.

In a specific embodiment, the linking moiety between the phenylboronate and the cargo molecule also contains a label which functions on binding or ligation of the boronated oligopeptide to the cargo molecule to label the cargo molecule.

In general, the reactive groups of the cargo molecule and the phenyl boronate are selected to achieve the desired linkage and for any desired selectable cleavage, or more specifically to achieve a desired covalent linkage which is optionally selectively cleavable and which is suitable for the desired application of the boronated cargo molecule.

In another embodiment, the boronating method involves attaching a boronated amino acid or a boronated oligopeptide, which are substituted with one or more phenylboronate groups, to the cargo molecule. The boronated amino acid or oligopeptide can be generated by forming covalent bond(s) between one or more reactive groups on an amino acid or oligopeptide and a reactive group on one or more phenylboronic acid compounds. The reaction of these reactive groups results in the formation of a linking moiety between the phenylboronate group and the amino acid or oligopeptide. As noted above, the linking moiety comprises newly formed bonds, particularly covalent bonds, and any residual moieties from the reactive groups.

Additionally, the reactive groups on the amino acid, oligopeptide or the phenylboronate compound are themselves optionally attached to the amino acid, oligopeptide or phenylboronate compound via a spacer moiety. In this case the linking moiety that results from reaction of the reactive groups contains any such spacer moieties in the starting amino acid, oligopeptide or phenylboronate compounds, bonds that are formed by reaction of reactive groups and any residue of the reactive groups. The reactive groups of the oligopeptide may be those that occur naturally in amino acids therein, may be those that occur in non-naturally occurring amino acids introduced into the oligopeptide by any art-known method or they may result from chemical modification of such naturally occurring reactive groups as is known in the art as noted above.

Boronated amino acids and boronated oligopeptides may also be commercially available or be made by art-recognized methods. The boronated amino acid or the boronated oligopeptide can be attached to the cargo molecule to be boronated by any art-recognized method.

For example, a boronated amino acid or oligopeptide can be modified, for example, to contain a ligand which selectively binds to the cargo peptide or protein, such as biotin or a derivative thereof such as biocytin.

In another alternative method, the boronated oligopeptide can be coupled to the cargo molecule employing a crosslinking reagent which may contain 2 or more reactive groups for crosslinking. Homobifunctional and heterobifunctional crosslinking reagents are particularly useful. For example, the boronated oligopeptide can be coupled to the cargo molecule employing a homobifunctional crosslinking reagent or a heterobifunctional crosslinking reagent.

More generally, heterofunctional crosslinking reagents may include a plurality of reactive groups which are the same and one or more different reactive groups. Use of such heterofunctional crosslinking reagents will allow, for example, linking of two or more phenylboronic acid groups to a single cargo molecule.

In another embodiment, boronation of a boronated oligopeptide for attachment to a cargo molecule or boronation of a cargo peptide or protein can be accomplished by introduction of one or more boronated amino acids into the peptide or protein. Boronated amino acids can be introduced onto the peptide or protein directly by solid phase peptide synthesis wherein one or more of the amino acid derivatives employed for peptide synthesis are boronated to contain a phenylboronate group or benzoboroxole group. Alternatively, a boronated oligopeptide can be generated by solid phase peptide synthesis employing one or more boronated amino acids as starting materials for peptide synthesis. The boronated oligopeptide can be boronated cargo (where the cargo is the oligopeptide) or the boronated oligopeptide can thereafter be bound to, ligated to or crosslinked to the cargo which is to be boronated.

Boronated oligopeptides useful as boronated cargo or useful for boronating cargo can include those having 2-30 amino acids and more specifically those having 5 to 20 amino acids. Boronated oligopeptides include those where 60% or less, 50% or less, 40% or less, or 25% or less of the amino acids of the oligopeptide carry a phenylboronate group. Boronated oligopeptides include those carrying 1, 2, 3, 4, 5, 6, 7, 8, 9, or 10 phenylboronic acid groups. Boronated oligopeptides include those comprising one or more glutamic acids and/or aspartic acids which are boronated with phenylboronate groups.

Amino acids boronated with phenylboronate or benzoboroxole are available from art-known methods or are prepared as described above for the boronation of peptides and protein by reaction of a reactive group of the amino acid with a reactive group of a phenylboronate or benzoboroxole compound. The phenylboronate or benzoboroxole groups is bonded to the amino acid via a linking moiety as described above which contains any bond resulting from reaction of the reactive groups, any residue of the reactive group, any spacer moieties in the starting amino acid or phenylboronate or benzoboroxole compound and any optional label.

Boronated peptides, proteins and oligopeptides of this invention are also optionally labeled for direct or indirect detection by any art-known method. In specific embodiments, suitable labels include isotopic labels, dyes, fluorescent or chemiluminescent groups or moieties, radiolabels, haptens and the like. In a specific embodiment, a label may be included in the linking moiety between at least one phenylboronate group and the peptide or protein. In specific embodiments, wherein cleavable linkers are employed, a label may be included in the linking moiety such that the label remains linked to the peptide or protein on cleavage of the linker. In alternative embodiments, wherein cleavable linkers are employed, a label may be included in the linking moiety such that the label is removed from the peptide or protein on cleavage of the linker.

Reactive groups of the cargo peptides or proteins or of oligopeptides or amino acids used for boronation may be those that occur naturally in amino acids (e.g., proteinogenic amino acids) therein, may be those that occur in non-naturally occurring amino acids introduced into the peptide or protein by any art known method or they may result from chemical modification of such naturally-occurring or non-naturally-occurring reactive groups as is known in the art. The reactive groups of peptides or proteins may, among others, be C-terminal carboxylate groups, N-terminal amino groups, and/or amino groups, sulfhydryl groups, hydroxyl groups or carboxylate groups of a side group of any naturally-occurring amino acid of the peptide or protein. In specific embodiments, the reactive groups which are used for boronation are amino groups and the boronation is facilitated by formation of an amide bond. The reactive groups of the peptide or protein may also, among others, be activated ester groups, thioester groups, phosphinothiol ester groups, azide groups, aldehyde and/or ketone groups generated in or introduced into the peptide or protein by any art-known method.

When the cargo molecule is a peptide or protein, boronation can be achieved, for example, by ligating a boronate oligopeptide to the peptide or protein by any known method of peptide ligation, particularly by the formation of an amide bond between the N- or C-termini of the oligopeptide and the peptide or protein. Alternatively, the boronated oligopeptide can be modified, for example, to contain a ligand which selectively binds to the cargo peptide or protein, such as biotin or a derivative thereof such as biocytin.

When the cargo is a nucleic acid or analog thereof, the reactive group used to facilitate boronation may be any of those that occur naturally in nucleic acids, and particularly any of those that occur in nucleoside bases as well as those that occur in non-naturally occurring nucleosides or those that can be introduced into the nucleotide or nucleoside by any art known method or they may result from chemical modification of such naturally-occurring or non-naturally-occurring reactive groups as is known in the art. In specific embodiments, the reactive groups which are used for boronation are amino groups and the boronation is facilitated by formation of an amide bond. The preferred reactive group for boronation of nucleic acids is an exo-amino group of the nucleic acid, e.g., an amino group of a nucleoside base, e.g., the amino groups of cytosine, guanine, or adenine bases or analogs thereof (e.g., isocytosine, isoguanine, diaminopurine or diaminopyridine, among others) which contain amino groups.

In specific embodiments, the invention provides boronation reagents, particularly those which are phenyl boronates or benzoboroxoles. Such reagents can comprise reactive groups and/or latent reactive groups to facilitate bonding to cargo molecules or to facilitate selective cleavage of any linkers formed with cargo molecules. Such reagents can also comprise spacer moieties (within linkers formed) or reporter or label moieties (optionally within linkers formed or otherwise formed in the reagent.)

In specific embodiments, phenylboronic acid and benzoboroxole compounds employed for boronation in this invention have only one boronic acid group —$B(OH)_2$, —$B(OH)$— moiety or B atom in the compound. In specific embodiments, the phenyl ring of phenylboronic acids or benzoboroxole is substituted with one or more electron withdrawing groups. More specifically the phenyl ring of phenylboronic acids, benzoboroxoles, or of the phenylboronic or benzoboroxole groups is substituted at the 2- and/or 4-ring positions (i.e., ortho or para positions) with respect to the bond to the boron with one to four electron withdrawing groups. In specific embodiments, the phenylboronate is substituted at the 2-ring position with a —$(CR_7R_8)_x$—OH group, where x is 1 or 2 and $R_7$ and $R_8$ are as defined below, which respectively form a 5-member boroxole or a 6-member oxaborin ring, where in specific embodiments each $R_7$ and $R_8$ is a hydrogen.

In specific embodiments, the cargo molecule is boronated to contain 4 or more, 5 or more, 10 or more or 20 or more phenylboronate or benzoboroxole groups. In more specific embodiments, the peptide or protein is boronated to contain 2-10 phenylboronate or benzoboroxole groups. In specific embodiments, a cargo molecule can optionally be boronated with two or more different phenylboronate or benzoboroxole groups. In a specific embodiment, a peptide or protein is boronated with one or more phenylboronate or benzoboroxole groups that are all the same.

In an additional embodiment, the invention provides a method for preparation of boronated cargo, boronated peptides, and particularly boronated oligopeptides, by solid phase peptide synthesis employing phenylboronated protected amino acids. Boronated cargo molecules, which are not peptides or proteins, are prepared by ligation of a boronated peptide, particularly a boronated oligopeptide, to the cargo molecule. In a specific embodiment, boronated oligopeptides are prepared by Fmoc solid phase peptide synthesis employing Fmoc-protected boronated amino acids. In a more specific embodiment, Fmoc-protected boronated glutamic acid or Fmoc-protected boronated phenyl alanine are employed to prepare peptides, including oligopeptides which contain one or more boronated glutamic acid residues, one or more boronated aspartic acid residues, one or more boronated phenyl alanine residues or a combination of such amino acid residues.

The invention also specifically provides various Fmoc-protected phenylboronated amino acids for use in solid phase peptide synthesis. The invention also provides a method for boronating a peptide or protein which comprises the step of binding or ligating or crosslinking a boronated oligopeptide reagent with the peptide or protein.

The invention further provides a method for enhancing cellular uptake of a cargo molecule by boronating the peptide or protein with one or more phenylboronate groups and thereafter contacting the boronated peptide or protein with a selected cell. In a specific embodiment, cargo molecule is boronated with two or more phenylboronate or benzoboroxole groups. In a specific embodiment, the phenylboronate is a compound of formula IA or IB (see below). In specific embodiments, the phenylboronate is a benzoboroxole (also called a benzoxaborole) compound of formula IB, wherein x is 1. In specific embodiments, the cargo molecule is boronated by binding, ligation or crosslinking of a boronated oligopeptide to a peptide or protein. In specific embodiments, the cargo molecule is a peptide, protein or a nucleic acid.

More specifically, the invention provides a method for improved delivery of a cargo molecule to a eukaryotic cell, particularly a mammalian cell, which comprises the step of contacting the cell or tissue containing the cell with a boronated cargo molecule. In a specific embodiment, the invention provides a method for improved delivery of a cargo molecule to an an intracellular site. In a specific embodiment, the step of contacting the cell or tissue is conducted in vitro. In a specific embodiment, the step of contacting the cell or tissue is conducted in vivo. In a specific embodiment, the boronated cargo molecule comprises a boronated oligopeptide moiety of this invention. In specific embodiments, the cargo molecule carries two or more phenylboronate groups. In specific embodiments, the cargo molecule is a peptide or protein which is boronated by reaction at one or more carboxylate groups in the peptide or protein. In specific embodiments, the cargo molecule is a peptide or protein which is boronated by reaction at one or more amino groups in the peptide or protein. In a specific embodiment, the cargo protein is an enzyme. In a specific embodiment, the cargo protein itself is not glycosylated (i.e., is not a glycoprotein). In a specific embodiment, the boronated cargo protein retains at least 10% of a selected biological activity of the protein prior to boronation. In a specific embodiment, the boronated cargo enzyme retains at least 10% of the activity of the enzyme prior to boronation. In another specific embodiment, the cargo peptide or protein is an antibody or functional fragment thereof and more specifically is a monoclonal antibody or functional fragment thereof.

In specific embodiments, the cargo molecule is a nucleic acid which is boronated by reaction at one or more amino groups in the nucleic acid. In a specific embodiment, the cargo protein is an enzyme. In a specific embodiment, the cargo protein itself is not glycosylated (i.e., is not a glycoprotein). In a specific embodiment, the boronated cargo nucleic acid retains at least 10% of a selected biological activity of the nucleic acid prior to boronation. In a specific embodiment, the biological activity retained is binding of the nucleic acid to complementary nucleic acid.

The invention further provides kits for enhanced cellular uptake of a peptide or protein which comprise one or more of the phenylboronate compounds of this invention or one or more of the boronated oligopeptide reagents of the invention which are individually packaged therein in selected amounts for use in boronating one or more peptides or proteins for enhanced uptake. The invention also provides kits for boronation of a peptide or protein which comprise one or more of the phenylboronate compounds of this invention or one or more of the boronated oligopeptide reagents of the invention which are individually packaged therein in selected amounts. Reagent kits may further comprise one or more solvents or reagents for carrying out binding, ligation, crosslinking or reaction of a phenylboronate or boronated oligopeptide with a selected peptide or protein. Kits for enhanced cellular uptake may further comprise one or more selected peptides or proteins to be delivered to cells, optional reagents for labeling the peptide or protein, or reagents, media or solvents for contacting cells with the boronated peptide or protein.

Additional embodiments of the invention will be apparent on review of the drawings, the following detailed description and the examples.

BRIEF DESCRIPTION OF THE DRAWINGS

FIGS. 13A-D illustrate the determination of the $^1$H NMR peaks corresponding to the aryl protons in bound and free boronic acid. (13A) $^1$H NMR spectrum of solution 1. (13B) $^1$H NMR spectrum of solution A. (13C) Overlay of aromatic region of spectra from panels A and B. (13D) Example of a spectrum that was interpreted using the overlay from panel C, and used to determine the value of $K_a$ for fructose with PBA. The [B·S]/[B] ratio was calculated from the isolated peaks for the complex (3H, 7.01-7.11 ppm) and the isolated peaks for the free boronic acid (2H, 7.54-7.58 ppm).

DETAILED DESCRIPTION OF THE INVENTION

Figure 22:
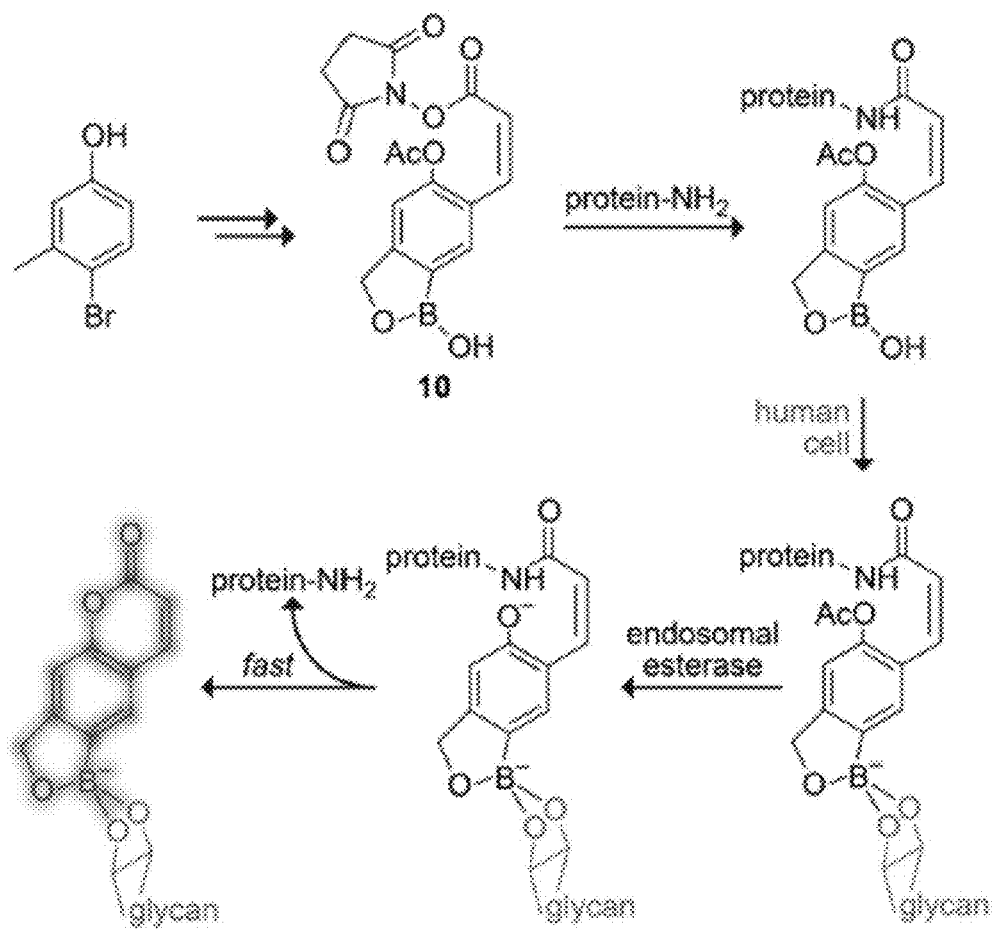
FIG. 22 illustrates a scheme for cellular uptake mediated by boronyl pendants. Boronate 10 is an exemplary boronation reagent (an exemplary benzoboroxole) of the invention used to acylate the amino groups of a cargo molecule, such as a target protein or nucleic acid. Multivalent complexation with cell-surface glycans facilitates entry into endosomes, where esterases will release intact protein. The fluorescence of the coumarin product can be employed to determine uptake.

The invention is based at least in part on the demonstration that pendant phenylboronic acids mediate the delivery of molecules (cargo) into mammalian cells. More specifically, bonding of one or more phenylboronic acids to such molecules, particularly nucleic acids, and peptides or proteins generally enhances uptake of the boronated cargo molecule into mammalian cells. Additionally, in specific embodiments, the boronated cargo molecule retains biological activity of the corresponding non-boronated cargo molecule. FIG. 22 illustrates use of a boronation reagent of the invention (compound 10) to boronate a protein and further illustrates the scheme for cellular uptake of cargo (exemplified by protein). Multivalent complexation with cell-surface glycans is believed to facilitate entry into endosomes, where cargo is released, for example by enzyme action. In the illustrated scheme, esterases release intact cargo protein. In the illustrated example, fluorescence of the coumarin by-product of release can be employed to assess uptake of cargo molecule.

More specifically herein, boronation of peptides and proteins, e.g., RNase A, lysozyme and avidin, is shown to generally enhance uptake of the boronated peptide or protein into mammalian cells.

The term "enhancement of cellular uptake" refers to enhancement of uptake of a boronated cargo molecule compared to uptake of the analogous non-boronated cargo molecule. Enhancement of cellular uptake can be measured by any art-known method and useful methods are exemplified in the examples. In specific embodiments, enhancement of cellular uptake of 2-fold or higher relative to the non-phenylboronated cargo molecule is obtained. Enhancement of cellular uptake may be assessed in terms of % internalization compared to non-boronated cargo molecule. In specific embodiments, enhancement of % internalization of 50% or more compared to controls is obtained.

Enhanced delivery of boronated cargo, particularly boronated proteins, e.g., boronated RNase A is described hereafter in more detail.

In specific embodiments, the invention provides methods and reagents for boronating cargo molecules, and particularly boronating of amino acids, peptides, proteins, nucleic acids and analogs thereof and nucleosides and analogs thereof with phenylboronate or benzoboroxole groups to enhance uptake of such cargo molecules into cells.

In specific embodiments, the invention provides methods and reagents for boronating nucleotides, nucleic acids and analogs thereof.

In specific embodiments, the invention provides methods and reagents for boronating peptides and proteins.

In specific embodiments, the invention provides methods and reagents for boronating cargo molecules which contain one or more amino groups wherein boronation is facilitated by formation of one or more amide bonds.

Herein, phenylboronate groups (PB) are chemical groups in which a

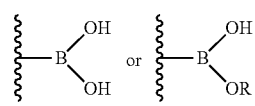

is directly attached to an optionally substituted phenyl ring, where R is an optionally substituted aliphatic group which optionally links to the phenyl ring to form a 5- or 6-member boroxole ring. In specific embodiments, the boronate group is:

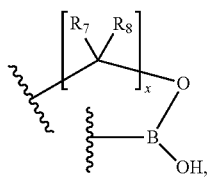

where $R_7$, $R_8$ and x are defined above.

Additional phenylboronates are phenyl groups carrying a —B(OR$_B$)$_2$ where each —R$_B$ is an optionally substituted aliphatic group or optionally substituted heteroaliphatic group, particularly an optionally substituted alkyl group, wherein the two R$_B$ are optionally linked together to form an optionally substituted 5- to 8-member heteroaliphatic ring. In a specific embodiment, the —B(OR$_B$)$_2$ group is:

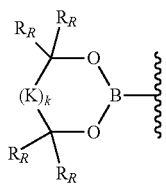

where each $R_R$ is independently hydrogen or alkyl, particularly a C1-C3 alkyl group, k is 0 or 1 and K is selected from an optionally substituted divalent aliphatic or an optionally substituted divalent heteroaliphatic moiety having 1 to 3 atoms in the divalent aliphatic or heteroaliphatic moiety. When k is 0 there is a single bond between the carbons in the ring. In specific embodiments, K is selected from —(CH$_2$)$_{1-3}$—, —(CH$_2$)$_{1-2}$—O—, —CH$_2$—O—CH$_2$—, —O—(CH$_2$)$_{1-2}$—, —(CH$_2$)$_{1-2}$—NR$_R$—, —CH$_2$—NR$_R$—CH$_2$—, —NR$_R$—(CH$_2$)$_{1-2}$—, —(CH$_2$)$_{1-2}$—S—, —CH$_2$—S—CH$_2$—, or —S—(CH$_2$)$_{1-2}$, where each carbon of the K moiety is independently optionally substituted, particularly with one or two —R$_R$ groups. In preferred embodiments, k is 0 and the boronate group has a 5-member ring:

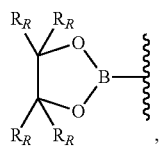

where $R_R$ is as defined above, but in specific embodiments all $R_R$ are methyl groups or all $R_R$ are hydrogen. In other embodiments, k is 1 and K is: —[C(R$_R$)$_2$]$_{1-3}$—, —(CH$_2$)—, —(CH$_2$)$_2$— or —(CH$_2$)$_3$—, —(CH$_2$)$_2$—NR$_R$—(CH$_2$)$_2$—, or —(CH$_2$)$_2$—N(CH$_3$)—(CH$_2$)$_2$—.

In specific embodiments, the phenyl ring of the phenylboronate is also substituted with one, two, three or four non-hydrogen substituents. In specific embodiments, the phenyl ring of the phenylboronate is also substituted with one, two, three or four non-hydrogen substituents which are electron withdrawing groups. Substitution of the phenyl ring with one or more electron withdrawing groups is believed to enhance binding of the boronate group to diols, particularly diols of saccharides. In specific embodiments, phenylboronates of this invention are not bound to a solid, such as a resin or other polymeric material and are not bound to a surface. Phenylboronates useful in the present invention include those of formulas IA and IB and salts thereof as described below.

In specific embodiments, the phenylboronic acids employed for boronation are selected from those having formula IA or IB:

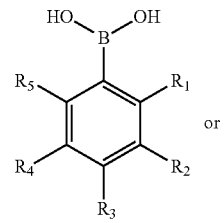

IA

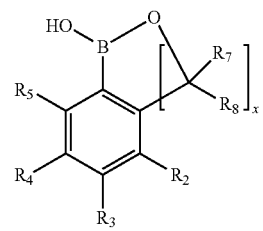

IB (noting that IB is a benzoboroxole structure) and salts thereof, where:

x is 1 or 2;

$R_1$-$R_5$ are independently selected from hydrogen, a straight-chain or branched aliphatic group having 1-8 carbon atoms, an alicyclic group, an aryl group, a heterocyclic group, a heteroaryl group, a —CO$_2$R$_{10}$ group, a —O—CO—R$_{10}$ group, a —CON(R$_{12}$)$_2$ group, a —O—CON(R$_{12}$)$_2$ group; a —N(R$_{12}$)$_2$ group, a —OR$_{10}$ group, a —(CH$_2$)$_m$—OH group, a —(CH$_2$)$_m$—N(R$_{12}$)$_2$ group, a halogen, a nitro group, a cyano group, a —SO$_2$—OR$_{10}$ group, -M, or two adjacent R$_2$-R$_6$, together with the ring carbons to which they are attached, optionally form a 5-8-member alicyclic, heterocyclic, aryl or heteroaryl ring moiety, each of which groups or moieties is optionally substituted;

each R$_7$ and R$_8$ is independently selected from hydrogen or a C1-C3 optionally substituted alkyl group;

wherein:

each R$_{10}$ is independently selected from hydrogen, a straight-chain or branched aliphatic group having 1-8 carbon atoms, an alicyclic group, an aryl group, a heterocyclic group, or a heteroaryl group, each of which groups is optionally substituted;

each R$_{12}$ is independently selected from hydrogen, a straight-chain or branched aliphatic group having 1-8 carbon atoms, an alicyclic group, an aryl group, a heterocyclic group, a heteroaryl group, or where two R$_{12}$ together with the nitrogen to which they are attached can form a 5-8 member heterocyclic or heteroaryl ring moiety, each of which groups or moieties is optionally substituted;

m is an integer from 1-8;

M is a reactive group or a spacer moiety substituted with a reactive group for forming a bond to a cargo molecule and wherein at least one of R$_1$-R$_6$ is M; and wherein optional substitution is substitution by one or more substituents selected from halogen; an oxo group (=O), a nitro group; a cyano group; a C1-C6 alkyl group; a C1-C6 alkoxy group; a C2-C6 alkenyl group; a C2-C6 alkynyl group; a 3-7 member alicyclic ring, wherein one or two ring carbons are optionally replaced with —CO— and which may contain one or two double bonds; an aryl group having 6-14 carbon ring atoms; a phenyl group; a benzyl group; a 5- or 6-member ring heterocyclic group having 1-3 heteroatoms and wherein one or two ring carbons are optionally replaced with —CO— and which may contain one or two double bonds; or a heteroaryl group having 1-3 heteroatoms (N, O or S); a —$CO_2R_{13}$ group; —OCO—$R_{13}$ group; —CON($R_{14}$)$_2$ group; —OCON($R_{14}$)$_2$ group; —N($R_{14}$)$_2$ group; a —$SO_2$—$OR_{13}$ group, —$OR_{13}$ group, —$(CH_2)_m$—$OR_{13}$ group, —$(CH_2)_m$—N($R_{14}$)$_2$, where m is 1-8 and each $R_{13}$ or $R_{14}$ is independently hydrogen; an unsubstituted C1-C6 alkyl group; an unsubstituted aryl group having 6-14 carbon atoms; an unsubstituted phenyl group; an unsubstituted benzyl group; an unsubstituted 5- or 6-member ring heterocyclic group, having 1-3 heteroatoms and wherein one or two ring carbons are optionally replaced with —CO— and which may contain one or two double bonds; or a heteroaryl group having 1-3 heteroatoms (N, O or S) and in addition two $R_{14}$ together with the nitrogen to which they are attached can form a heterocyclic or heteroaryl ring moiety, each of which groups or moieties is optionally substituted;

each of which $R_{13}$ and $R_{14}$ groups is in turn optionally substituted with one or more unsubstituted C1-C3 alkyl groups, halogens, oxo groups (=O), nitro groups, cyano groups, —$CO_2R_{15}$ groups, —OCO—$R_{15}$ groups, —CON($R_{16}$)$_2$ groups, —OCO—N($R_{16}$)$_2$ groups, —N($R_{16}$)$_2$ groups, a —$SO_2$—$OR_{15}$ group, —$OR_{15}$ groups, —$(CH_2)_m$—$OR_{15}$ groups, —$(CH_2)_m$—N($R_{16}$)$_2$ where m is 1-8 and each of $R_{15}$ and $R_{16}$ independently are hydrogen, an unsubstituted C1-C6 alkyl group; an unsubstituted aryl group having 6-14 carbon ring atoms; an unsubstituted phenyl group; an unsubstituted benzyl group, an unsubstituted 5- or 6-member ring heterocyclic group having 1-3 heteroatoms and wherein a ring carbon is optionally replaced with —CO— and which may contain one or two double bonds; or a heteroaryl group having 1-3 heteroatoms (N, O or S) and a total of 5-14 ring atoms; and in addition two $R_{16}$ together with the nitrogen to which they are attached can form an unsubstituted heterocyclic or heteroaryl ring moiety.

In specific embodiments M is a reactive group and more specifically an amine-reactive group. In specific embodiments, M is an amine-reactive group or a spacer moiety substituted with an amine-reactive group for forming one or more amide bonds to a cargo molecule comprising one or more amino group. In specific embodiments, M is M1 which is a latent reactive group or a spacer moiety substituted with a latent reactive group, which latent reactive group does not react with any reactive group in the compound of formula IA or IB, or in any other M group in the in compound, and which is selectively reactive, or can be selectively activated for reaction, after the compound is bonded to the cargo molecule. A latent reactive group can, for example, be activated for reaction inside of a cell for example by enzyme action inside of a cell. A latent reactive group can for example be activated by action of an esterase, for example after the cargo is delivered to a cell. In specific embodiments, M is M2 and is a spacer moiety substituted with a reactive group. More specifically, M2 is a spacer moiety comprising a latent reactive group and substituted with a reactive group for forming a bond to the cargo molecule wherein the latent reactive group does not react with the reactive group or the cargo molecule and can be selectively reacted or activated for reaction after the cargo molecule is boronated. In specific embodiments, the reactive group of M2 is an amine-reactive group. In specific embodiments, the compound of formula IA or IB comprises two -M groups, which more specifically are M1 which is or which comprises a latent reactive group and M2 which is a spacer moiety which comprises a reactive group for bonding to cargo and a latent reactive group. In specific embodiments, the latent reactive groups of M1 and M2 cooperate to effect cleavage of the linker and to cleave the phenyl boronate groups from the cargo molecule. In specific embodiments of formulas IA and IB, $R_3$ or $R_4$ is -M.

In specific embodiments of formula IB, x is 1 and the boronating species is a benzoboroxole. In specific embodiments, each $R_7$ and $R_8$ is independently hydrogen or a methyl group. In specific embodiments, the compound of formula IA or IB contains a single -M group. In specific embodiments, the compound of formula IA or IB contains a single -M group and one of $R_2$-$R_4$ is -M. In specific embodiments, $R_3$ or $R_4$ is -M.

In specific embodiments, the compound of formula IA or IB contains two -M groups, one of which is M1 and the other of which is M2, where M1 is a latent reactive group and M2 is a spacer substituted with a reactive group and which contains a latent reactive group. More specifically, the latent reactive groups of M1 and M2 function together to cleave the boronate from the cargo molecule on selective activation of one or both latent reactive groups.

In specific embodiments of formula IA and IB, M1 and M2 are substituted on adjacent ring carbons in the phenyl ring. More specifically, $R_2$ is M1 and $R_3$ is M2; $R_2$ is M2 and $R_3$ is M1; $R_4$ is M1 and $R_3$ is M2; $R_3$ is M1 and $R_4$ is M2; $R_4$ is M1 and $R_5$ is M2; $R_4$ is M2 and $R_5$ is M1; $R_1$ is M1 and $R_2$ is M2; $R_1$ is M2 and $R_2$ is M1; $R_4$ is M1 and $R_6$ is M2; or $R_4$ is M2 and $R_6$ is M. More specifically in compounds of formula IA, $R_2$ is M1 and $R_3$ is M2; $R_2$ is M2 and $R_3$ is M1; $R_4$ is M1 and $R_3$ is M2; or $R_3$ is M1 and $R_4$ is M2 and more specifically in compounds of formula IB $R_4$ is M1 and $R_3$ is M2; or $R_3$ is M1 and $R_4$ is M2.

In specific embodiments of formula IA or IB, $R_1$, $R_5$ and $R_6$ are independently selected from hydrogen, an optionally substituted straight-chain or branched aliphatic group having 1-8 carbon atoms, a —$CO_2R_{10}$ group, a —O—CO—$R_{10}$ group, a —CON($R_{12}$)$_2$ group, a —O—CO—N($R_{12}$)$_2$ group, a —N($R_{12}$)$_2$ group, a —$OR_{10}$ group, a —$(CH_2)_m$—$OR_{10}$ group, a —$(CH_2)_m$—N($R_{12}$)$_2$ group, a halogen, a nitro group, or a cyano group, where variables are as defined above. In more specific embodiments, $R_1$ and $R_5$ or $R_6$ are independently selected from hydrogen; C1-C3 alkyl group; —$CO_2H$; —$CONH_2$; —$NH_2$; —CON($R_{12}$)$_2$ or —N($R_{12}$)$_2$, where $R_{12}$ is a C1-C6 alkyl group; a hydroxyl; a C1-C3 alkoxyl; a —$(CH_2)_m$—OH or —$(CH_2)_m$—$NH_2$ group where m is 1-3; halogen, nitro group or cyano group.

In specific embodiments of formula IA or IB, $R_2$, $R_3$ and $R_4$ are independently selected from hydrogen, -M, an optionally substituted straight-chain or branched aliphatic group having 1-8 carbon atoms, a —$CO_2R_{10}$ group, a —O—CO—$R_{10}$ group, a —CON($R_{12}$)$_2$ group, a —O—CO—N($R_{12}$)$_2$ group, a —N($R_{12}$)$_2$ group, a —$OR_{10}$ group, a —$(CH_2)_m$—$OR_{10}$ group, a —$(CH_2)_m$—N($R_{12}$)$_2$ group, a halogen, a nitro group, or a cyano group, where variables are as defined above, wherein at least one of $R_2$-$R_4$ is -M. Additionally, two adjacent $R_2$-$R_6$, together with the ring carbons to which they are attached, optionally form a 5- or 6-member alicyclic, heterocyclic, aryl or heteroaryl ring moiety wherein the ring members are optionally substituted.

In specific embodiments, variable groups of formulas IA and IB are optionally substituted as defined above. In more specific embodiments, optional substitution of compounds of formulas IA or IB is substitution of a group or moiety by 1-5 substituents selected from substituents as noted above. In additional embodiments, optional substitution of compounds of formulas IA or IB is substitution of a group or moiety by 1 or 2 substituents selected from substituents as noted above. In specific embodiments, optional substituent groups have 10 or less carbon atoms. In specific embodiments, optional substituent groups have 12 or less atoms. In specific embodiments, optional substituent groups have 6 or less carbon atoms. In specific embodiments, groups as defined for formulas IA and IB are unsubstituted. In specific embodiments, optionally substitution is substitution by one to 7 substituents selected from halogen (F, Cl, Br or I); nitro group; cyano group; a C1-C3 alkyl group; a C1-C3 alkoxy group; a C2-C3 alkenyl group; a C2-C3 alkynyl group; a 5- or 6-member alicyclic ring group, wherein one or two ring carbons are optionally replaced with —CO— and which may contain one or two double bonds; phenyl group; benzyl group; naphthyl group; biphenyl group; —COH; —CO$_2$H; —CONH$_2$; —NH$_2$; —OH; —SH or —SO$_3$H, wherein alkyl, alkenyl, alkynyl, alicyclic ring, phenyl; benzyl; naphthyl; and biphenyl groups are optionally substituted with one or more halogen, —OH group, —SH group, methyl group, methoxy group, trihalomethyl group, cyano group, or nitro group.

In specific embodiments herein, $R_1$-$R_6$ that are not -M do not contain a reactive group as described herein that is in the -M group. In specific embodiments herein, $R_1$-$R_6$ that are not -M may contain reactive groups as defined herein if those reactive groups are protected with an appropriate protective group which selectively prevents their reaction. Such protective groups may be removed if desired after boronation of the peptide or protein.

In specific embodiments, -M is a reactive group or a spacer moiety carrying a reactive group wherein the reactive group:
(1) reacts with one or more of: an amino group, a carboxylic acid group, a sulfhydryl group or a hydroxyl group, particularly where that group is a group of a natural or unnatural amino acid of such an amino acid of a peptide or a protein;
(2) reacts with an aldehyde or ketone group, an azide group, an activated ester group, a thioester group, phosphinothioester, or other group which is introduced into or generated in the amino acid, peptide or protein; or
(3) reacts with one reactive group of a homobidfunctional or a heterobifunctional crosslinking reagent to bond or attach the phenylboronate group substituted with the M group to an amino acid, peptide or protein.

In another embodiment, M is or contains a reactive group that can be ligated to a peptide or protein by a peptide ligation method. In specific embodiments, M is or contains an amino group, a carboxyl group or ester thereof, an activated ester group, an azide, a thioester, or a phosphinolthioester.

In general the optional spacer moiety of the M group is compatible with the reactive group therein (e.g., does not detrimentally affect reactivity of the reactive group) and the spacer itself is not reactive with the compounds to be conjugated. In specific embodiments, the spacer moiety contains from 3-20 atoms (typically C, O, S and/or N atoms which may be substituted with H or non-hydrogen substituents), including residues from the reactive group), and optionally contains one or more carbon-carbon double bonds, and/or a 5- to 8-member alicyclic, a 5- to 8-member heterocyclic, a 6- or 10-member aryl or a 5- or 6-member heteroaryl ring. Carbon atoms in the spacer or linker are optionally substituted with one or more hydroxyl groups, oxo moieties (=O), or halogens (e.g., F). Nitrogen groups in the spacer may be substituted hydrogen or with C1-C3 alkyl groups. The spacer may contain one or two —S—S— and/or —SO$_2$— moieties. The spacer may contain a diol (>C(OH)—C(OH)<) moiety.

In a specific embodiment, the spacer in the linker comprises one or more ether linkages. More specifically, the spacer is or comprises a —O—CH$_2$—O— moiety. In a specific embodiment, the linker between the phenyl boronate and the cargo molecule is or comprises an acetoxymethyl ether. More specifically, the linker is or comprises a —O—CH$_2$—O—CO— moiety. In a specific embodiment of formula IA or IB, any of $R_1$-$R_6$ is —O—CH$_2$—O—CO—CH$_3$ or comprises a —O—CH$_2$—O— or a —O—CH$_2$—O—CO— moiety. In a specific embodiment, M comprises a —O—CH$_2$—O— or a —O—CH$_2$—O—CO—. See: Lavis et al. (2011) [44]

The spacer may be selectively cleavable, for example, by change of conditions (e.g., pH change), addition of a cleavage reagent, or photoirradiation (e.g., UV irradiation). Such selectively cleavable spacers contain a latent reactive group which is selectively reactive or can be selectively activated for reaction. In specific embodiments, a cleavable spacer includes a disulfide bond which is selectively cleavable, for example on treatment with dithiothreitol, a diol moiety which is selectively cleavable by treatment for example with periodate, an ester moiety, which is selectively cleavable by treatment with hydroxylamine, or a sulfone moiety (—SO$_2$—) which is selectively cleavable under alkaline conditions.

In specific embodiments, -M is selected from:
—X or -LX, where X is the reactive group for ligation, bonding or crosslinking to an amino acid, peptide or protein and L is a spacer moiety. A variety of spacer moieties are known in the art to be useful for bioconjugation of molecules to amino acids, peptides and proteins. All such art-known spacer moieties can be employed in this invention, if compatible with the chemistry of the phenylboronate and the amino acid, peptide or protein and which do not detrimentally affect reactivity of chosen reactive groups and which do not themselves react with the phenylboronate, amino acid, peptide, protein or reactive groups.

In specific embodiments, L is selected from the following divalent moieties:
—Y1-L1-Y3-, where Y1 and Y3 are optional and may be the same or different;
—Y1-L1-L2-Y3-, where Y1 and Y3 are optional and may be the same or different and L1 and L2 are different; or
—Y1-L1-[L2-Y2]y-L3-Y3-, where Y1 and Y3 are optional, Y1, Y2 and Y3 may be the same or different, L1 and L3 are optional and L1, L2 and L3 may be the same or different and y is an integer indicating the number of repeats of the indicated moiety;
wherein each L1-L3 is independently selected from an optionally substituted divalent aliphatic, alicyclic, heterocyclic, aryl, or heteroaryl moiety having 1 to 30 atoms and each Y1, Y2 and Y3 is independently selected from: —O—, —S—, —NRc-, —CO—, —O—CO—, —CO—O—, —CO—NRc-, —NRc-CO—, —NRc-CO—NRc-, —OCO—NRc-, —NRc-CO—O—, —N=N—, —N=N—NRc-, —CO—S—, —S—CO—, —S—S—, —SO2-, —CRc(OH)—CRc(OH)—, where Rc is hydrogen or C1-C3 alkyl.

In specific embodiments, y is 1-12 and L1-L3 are selected from:
—(CH$_2$)y- (an alkylene) wherein one or more, and preferably 1-4, carbons of the alkylene are optionally substituted with one or more non-hydrogen substituents selected from halogens, C1-C3 alkyl groups or hydroxyl groups, preferably are 2-6;

a cycloalkylene, having a 3-8-member ring wherein one or more, and preferably 1-4, carbons of the cycloalkylene are optionally substituted with one or more non-hydrogen substituents selected from halogens, C1-C3 alkyl groups or hydroxyl groups, including among others a 1,4-cyclohexylene, a 1,3-cylohexylene, a 1,2-cyclohexylene; a 1,3-cyclopentylene, each of which is optionally substituted;

a phenylene, wherein 1-4 of the ring carbons are optionally substituted with one or more non-hydrogen substituents selected from halogens, C1-C3 alkyl groups, nitro group, cyano group, or hydroxyl groups, including a 1,4-phenylene, a 1,3-phenylene or a 1,2-phenylene, each of which is optionally substituted;

a naphthylene, wherein 1-8 of the ring carbons are optionally substituted with one or more non-hydrogen substituents selected from halogens, C1-C3 alkyl groups, nitro group, cyano group, or hydroxyl groups, including a 2,6-naphthylene, a 2,7-naphthylene, a 1,5-naphthylene, or a 1,4-naphthylene moiety, each of which is optionally substituted;

a biphenylene, wherein 1-8 of the ring carbons are optionally substituted with one or more non-hydrogen substituents selected from halogens, C1-C3 alkyl groups or hydroxyl groups, including a 1,4'-biphenylene, a 1,3'-biphenylene or a 1,2'-biphenylene, each of which is optionally substituted;

an alkenylene, i.e., a divalent alkylene group, containing one or more, preferably 1 or 2 double bonds and having 2-12 and preferably 2-8 carbon atoms, wherein one or more, and preferably 1-4, carbons are optionally substituted with one or more non-hydrogen substituents selected from halogens, C1-C3 alkyl groups or hydroxyl groups, including among others, —CH=CH— and —CH=CH—CH=CH— which are optionally substituted;

a heterocyclene (i.e., a divalent heterocyclic moiety) having a 3-8-member ring with 1-3 heteroatoms, selected from N, O or S, wherein one or more, and preferably 1-4 carbons, or where feasible heteroatoms, of the heterocyclene are optionally substituted with one or more non-hydrogen substituents selected from halogens, C1-C3 alkyl groups, nitro groups, or hydroxyl groups, including among others a 2,4-3H-azepinylene moiety, a piperidinylene (e.g., a 1,4-piperidinylene), a piperazinylene (e.g., a 1,4-piperazinylene), a triazolidinylene (a divalent triazolidinyl) or a triazolylene (a divalent triazolyl) each of which is optionally substituted; or a heteroarylene (i.e., a divalent heteroaryl moiety) having a 5- or 6-member heteroaryl ring having 1-3 heteroatoms selected from N, O or S, wherein one or more, and preferably 1-2 carbons, or where feasible heteroatoms, of the heteroarylene are optionally substituted with one or more non-hydrogen substituents selected from halogens, C1-C3 alkyl groups, nitro groups, or hydroxyl groups, including among others a pyridylene (e.g., 2-5-pyridylene), imidazolylene (e.g., 2,5-imidazolylene, 4,5-imidazolylene), each of which is optionally substituted.

In additional embodiments, the spacer is an ethylene glycol spacer. More specifically, -M is selected from —[(CH$_2$)$_y$—O]$_a$—, where y is 1-4 and a is 1-6, and preferably 1-3.

In additional embodiments, -M is selected from:
—CO—NH—CRaRb—[CO—NH—CRaRb]$_a$—CO—OH, where a is 1-6;
—COO—CRaRb—[CO—NH—CRaRb]$_a$—CO—OH, where a is 1-6;
—O—CO—NH—CRaRb—[NH—CO—CRaRb]$_a$—NH$_2$, where a is 1-6;
—Y4-CRaRb—[W—CRaRb]$_a$—X4, where W is —NH—CO— or —CO—NH—, where a is 1-6; where:

—X4 is a functional group that reacts with one or more of an amino group, a carboxylic acid group or ester thereof, a sulfhydryl group, a hydroxyl group, an azide group, a thioester group, a phoshinothioester group, an aldehyde group or a ketone group of an amino acid, peptide or protein; and —Y4- is —O—, —S—, —NH—, —CO—, —CO$_2$—, —O—CO—, —CO—O—, —CO—NRc-, —NRcCO—, —CO—S—, or —S—CO— and Rc is hydrogen or a C1-C3 alkyl;

Ra and Rb are selected independently from hydrogen, a C1-C8 aliphatic group, an alicyclic, a heterocyclic, an aryl or a heteroaryl group, each of which is optionally substituted or Ra is hydrogen and Rb is a side-group or protected side-group of a proteinogenic amino acids or an amino acid selected from hydroxyproline, ornithine, or citrulline.

In specific embodiments, the phenylboronic acid, except for the -M group or any salt counterion thereof, contains at most 20 carbon atoms.

In specific embodiments, X and X4 are —NH$_2$, —COOH or an activated ester thereof, —SH, —N$_3$, —COH, —CO—CH=CH$_2$, —NH—CO—CH=CH, or —C≡CH.

In specific embodiments, the invention provides boronation reagents of formulas IA and IB wherein M1 is a latent reactive group which can be activated to form —O$^-$, for example by cleavage of an ester bond (e.g., —O—CO—R$_{24}$, where R$_{24}$ is an optionally substituted alkyl or aryl group and specifically can be a —OCO—CH$_3$ group, cleavage of a —O—PO$_3$H$_2$ or related phosphate ester or cleavage of a —O—SO$_2$—R$_{25}$ group where R$_{25}$ is an substituted alkyl or aryl group, particularly a halogenated alkyl or a phenyl substituted with one or more halogens, nitro groups or other electron withdrawing groups.

For example, M1 can be activated by an esterase, an alkaline phosphatase or an exogenous thiol. In this embodiment, M2 carries a latent reactive group which cooperates with the —O$^-$ generated to cleave the M2 linker and cleave the boronate from the cargo molecule. In specific embodiments, M2 carries a trimethyl lock structure or a coumarin-based structure. [45a-f] Each of these references is incorporated herein for details on Specific M1 and M2 groups useful in this invention.

In specific embodiments, M2 is:

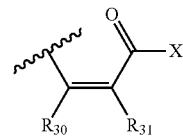

where R$_{30}$ and R$_{31}$ are H, alkyl (particularly C1-C3 alkyl) or R$_{30}$ and R$_{31}$ together with the intervening C=C moiety form a 6-8 member carbocyclic or heterocyclic ring wherein one of the ring carbons can be replaced with —CO—, such as a cyclohexenyl ring or cyclohexenone ring and —COX is an activated ester (e.g., X is a good leaving group), such as NHS esters (N-hydroxysuccinimide esters) or sulfo NHS esters (N-hydroxysulfosuccinimide esters).

In specific embodiments, M2 is:

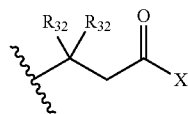

where —COX is an activated ester and each $R_{32}$ independently is a C1-C8 alkyl group or a C3-C8 cycloalkyl group. In a more specific embodiment, each $R_{32}$ is a C1-C3 alkyl group. More specifically, in compounds of formula IA and IB containing this M2, it is preferred that an adjacent carbon on the phenyl ring carries a C1-C8 alkyl group or a C2-C8 cycloalkyl group. More specifically the adjacent carbon on the phenyl ring carries a methyl group or a C2-3 alkyl group.

The invention further provides boronation reagents of the following formulas:

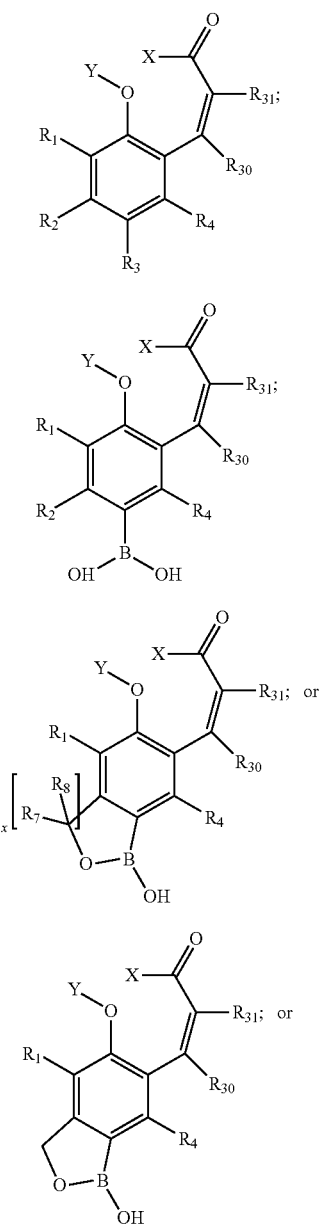

or salts thereof, where $R_1$-$R_4$ take values as defined for formulas IA and IB, except that in the reagent of formula IIA one of $R_2$ or $R_3$ is —B(OH)$_2$ or $R_2$ and $R_3$ together are:

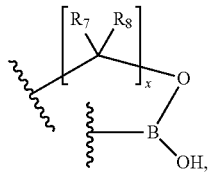

where $R_7$ and $R_8$ are defined above and preferably both are H and x is 1 or 2 and preferably 1;

$R_{30}$ and $R_{31}$ are as defined above;

X—CO— is an activated ester and

—O—Y is a precursor to —O⁻, i.e., Y is a labile group, as described above, and more specifically —OY is —O—CO—$R_{24}$, where $R^{24}$ is an optionally substituted alkyl or aryl group, a —O—PO$_3$H$_2$ or corresponding phosphate ester or a —O—SO$_2$—$R_{25}$ group, where $R_{25}$ is an substituted alkyl or aryl group, particularly a halogenated alkyl or an aryl group substituted with one or more halogens, nitro groups or other electron withdrawing groups. In a specific embodiment, $R_{25}$ is a phenyl group substituted with one or more halogens, nitro groups or other electron withdrawing groups.

The invention also provides boronation reagents of the following formulas:

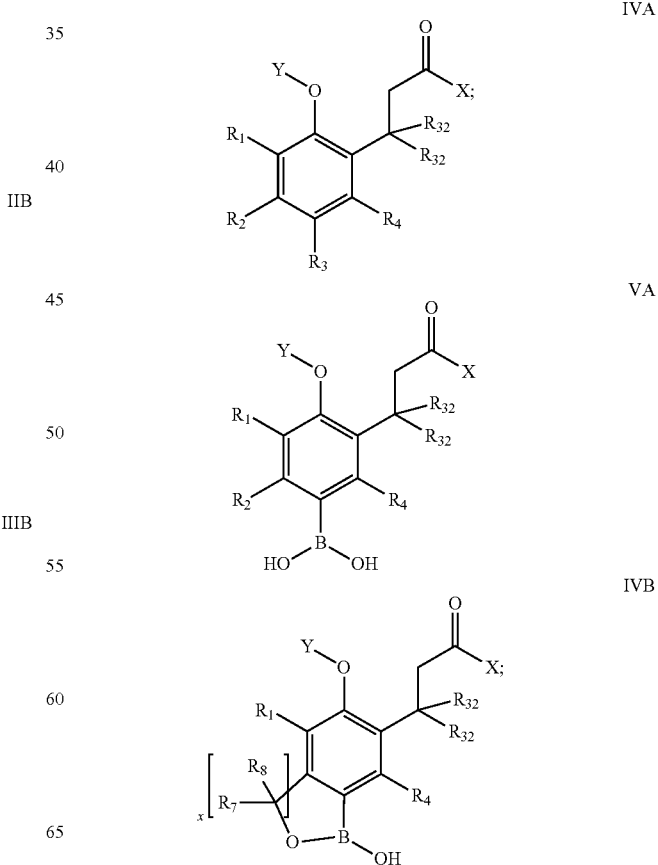

VB

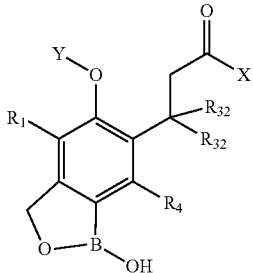

or salts thereof where $R_1$-$R_4$ take values as defined for formulas IA and IB, except that in the reagent of formula IVA one of $R_2$ or $R_3$ is —B(OH)$_2$ or $R_2$ and $R_3$ together are:

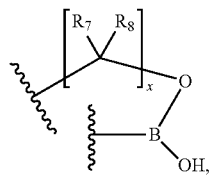

where $R_7$ and $R_8$ are defined above and preferably both are H and x is 1 or 2 and preferably 1 and where in a specific embodiment $R_4$ is a methyl group;

X—CO— is an activated ester and

—O—Y is a precursor to —O$^-$, i.e., Y is a labile group, as described above, and more specifically —OY is —O—CO—$R_{24}$, where $R^{24}$ is an optionally substituted alkyl or aryl group, a —O—PO$_3$H$_2$ or corresponding phosphate ester or a —O—SO$_2$—$R_{25}$ group, where $R_{25}$ is an substituted alkyl or aryl group, particularly a halogenated alkyl or an aryl group substituted with one or more halogens, nitro groups or other electron withdrawing groups. In a specific embodiment, $R_{25}$ is a phenyl group substituted with one or more halogens, nitro groups or other electron withdrawing groups. In specific embodiments, $R_4$ is a C1-C8 alkyl group or a C3-C8 cycloalkyl group. In specific embodiments, $R_4$ is a C1-C3 alkyl group and preferably is a methyl group.

The invention provides the following additional boronation reagents:

VI

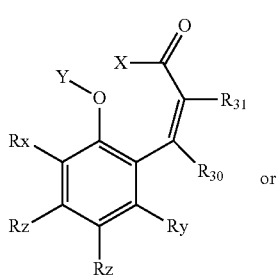

VII

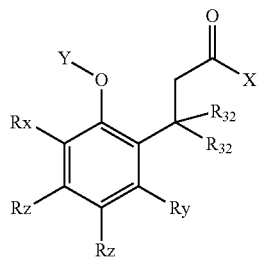

or salts thereof where X—CO—, Y—O—, $R_{30}$, $R_{31}$ are as defined above and Rx, Ry and Rz take values of $R_1$-$R_6$ above with the exception that one of the Rz's is a phenylboronate group of formula IA or IB, wherein one of $R_1$-$R_6$ provides a direct bond to or a linker to the phenyl ring of VI or VII. In a specific embodiment, the direct bond to the phenyl ring is a C—C bond, or a —O—C bond. In a specific embodiment, the linker is a linker as defined above or is selected from —(CH$_2$)$_a$—, —O—(CH$_2$)$_a$—, —S—(CH$_2$)$_a$—, —O—(CH$_2$)$_a$—O—, —(CH$_2$)$_a$—O—, —S—(CH$_2$)$_a$—S—, —CO—(CH$_2$)$_a$—, —OC—(CH$_2$)$_a$—, —CO—(CH$_2$)$_a$—CO—, —(CH$_2$)$_a$—CO—, —NHCO—(CH$_2$)$_a$—, —(CH$_2$)$_a$—CONH—, —NHCO—(CH$_2$)$_a$—CO— or —CO—(CH$_2$)$_a$—NHCO—; where a is an integer from 1-10 or 1-6. In specific embodiments of formula VII Ry is a C1-C8 alkyl group or a C3-C8 cycloalkyl group. In specific embodiments of formula VII Ry is a C1-C3 alkyl group or preferably is a methyl group.

Figure 23:
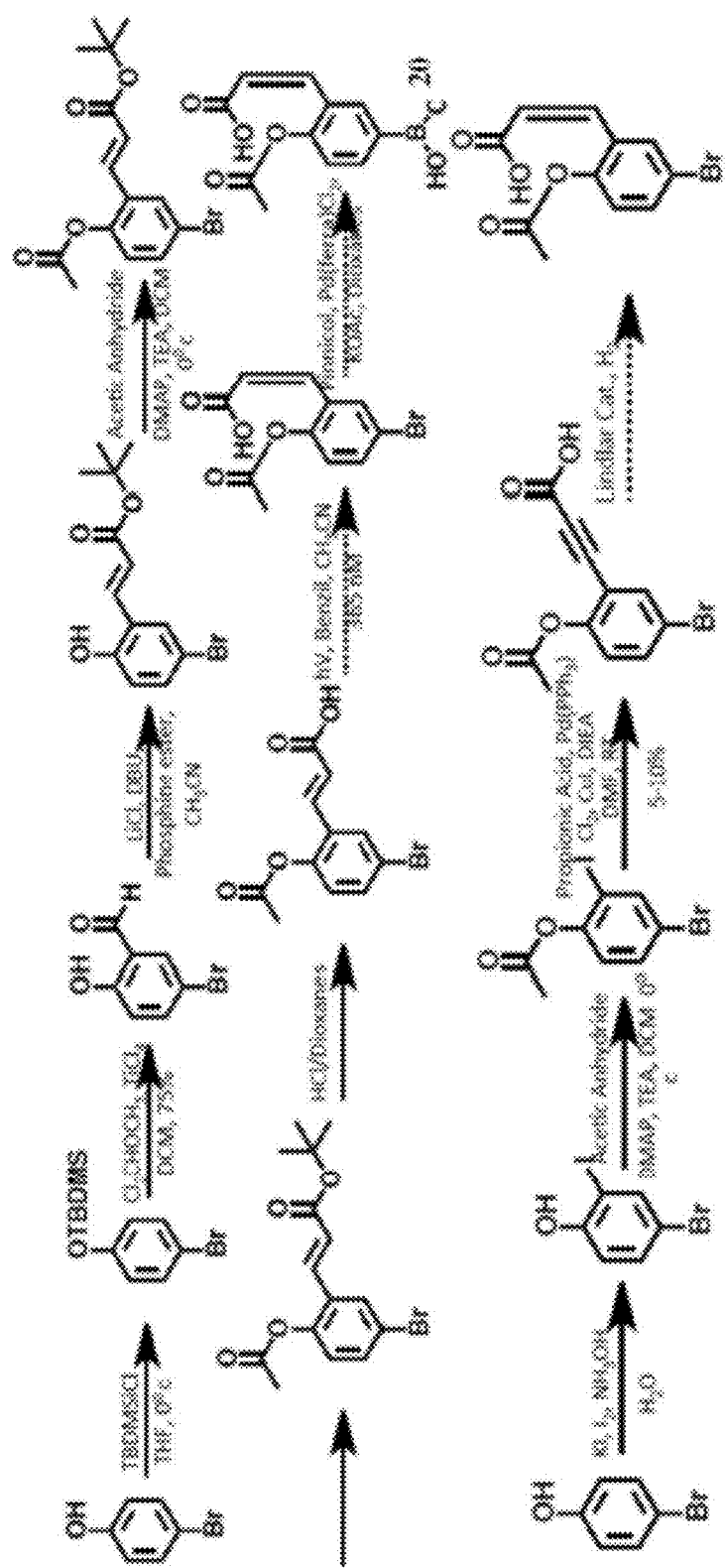
FIG. 23 illustrates synthesis of exemplary boronation reagents of the invention. Synthesis of the phenylboronate 20 is illustrated. The exemplary benzoboroxole is prepared by an analogous synthesis wherein the —$CH_2$—O—B(OH)— moiety of the benzoboroxole is installed by methods that are well known in the art.

Phenylboronate compounds of the invention can be prepared in view of the descriptions herein and methods that are known in the art or by routine adaptation of such methods. Methods useful for synthesis of phenylboronates of this invention can be found, for example, in U.S. Pat. Nos. 5,594,111; 5,594,151; 5,623,055; 5,777,148; 5,744,627; 5,837,878; and 6,156,884, in references [27] and [29-36]. Each of these references is incorporated by reference herein in its entirety for descriptions of such useful synthetic methods. FIG. 23 illustrates synthesis of an exemplary boronation agent of the invention (compound 20). The methods illustrated in FIG. 23 can be routinely adapted for synthesis of benzoboroxoles such as compound 10 illustrated in FIG. 22.

Boronation regents (phenylboronate compounds) of the invention specifically include those of formula:

VIIIA

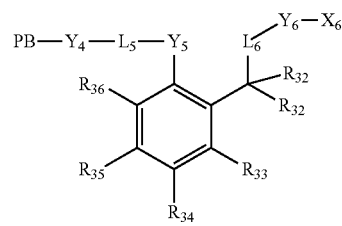

where:
PB is a phenylboronate group;
each $R_{32}$ and $R_{33}$ independently is a C1-C8 alkyl group or a C3-C8 cycloalkyl group;
$R_{34}$-$R_{36}$ are independently selected from hydrogen, a straight-chain or branched aliphatic group having 1-8 carbon atoms, a C3-C8 cycloalkyl group, an alicyclic group, an aryl group, a heterocyclic group, a heteroaryl group, a —$CO_2R_{10}$ group, a —O—CO—$R_{10}$ group, a —$CON(R_{12})_2$ group, a —O—$CON(R_{12})_2$ group; a —$N(R_{12})_2$ group, a —$OR_{10}$ group, a —$(CH_2)_m$—OH group, a —$(CH_2)_m$—$N(R_{12})_2$ group, a halogen, a nitro group, a cyano group, a —$SO_2$—$OR_{10}$ group, -M, or $R_{36}$ together with $R_{35}$ or $R_{35}$ together with $R_{34}$ and the ring carbons to which $R_{36}$-$R_{34}$ are attached, optionally form a 5-8-member alicyclic, heterocyclic, aryl or heteroaryl ring moiety, each of which groups or moieties is optionally substituted;

$Y_4$, $Y_5$ and $Y_6$ are independently selected from —O—, —S—, —NRc-, —CO—, —O—CO—, —CO—O—, —CO—NRc-, —NRc-CO—, —NRc-CO—NRc-, —OCO—NRc-, —NRc-CO—O—, —N=N—, —N=N—NRc-, —CO—S—, —S—CO—, —S—S—, —$SO_2$—, —CRc(OH)—CRc(OH)—, where Rc is hydrogen or C1-C3 alkyl;

$L_5$ and $L_6$ are divalent spacer moieties; and $X_6$ is a leaving group and —$Y_6$—$X_6$ together is a reactive group.

In specific embodiments, each $R_{32}$ and $R_{33}$ are C1-C3 alkyl groups and are preferably methyl groups.

$L_5$ and $L_6$ are defined as for L herein above.

In specific embodiments, $L_5$ and $L_6$ are selected from:
alkylene linkers (—$(CH_2)_y$—) wherein y is 1-12, and preferably 1-4;
alkoxyalkyl linkers —$[(CH_2)_q$—O—$(CH_2)_r]_a$— wherein q and r are zero or integers from 1-4, preferably 0, 1, 2 or 3, as long as one of q and r is not zero, and a is 1-6, preferably 2-4; or
aminoalkyl linkers —$[(CH_2)_s$—$NR_{N^-}(CH_2)_t]_b$— wherein $R_N$ is hydrogen or a C1-C3 alkyl group, s and t are 0 or integers from 1-4, and are preferably 0, 1 or 2 as long as one of s and t is not zero, and b is 1-3 and preferably is 1.

In specific embodiments $L_5$ is —$(CH_2)_2$— and $L_6$ is —$CH_2$—.

In specific embodiments, $Y_6$—$X_6$ together is a reactive group that reacts with one or more of an amino group, a carboxylic acid group or ester thereof, a sulfhydryl group, a hydroxyl group, an azide group, a thioester group, a phoshinothioester group, an aldehyde group or a ketone group of an amino acid, peptide or protein.

In specific embodiments, $Y_6$ is a —CO— and $X_6$ is a leaving group of an activated ester. In specific embodiments, $Y_6$ is —CO— and $X_6$ is a nitro- or halogen-substituted phenolate group. In specific embodiments, $Y_6$ is —CO— and $X_6$ is an N-oxido-succinimidyl or a N-oxido-sulfosuccinimidyl group. In specific embodiments, $X_6$ is pentafluorophenolate, tetrafluorophenolate or p-sulfo-tetrafluorophenolate.

In specific embodiments, $Y_4$ is —CO—, —O—CO—, —CO—O—, —CO—NRc-, —NRc-CO—, —NRc-CO—NRc-, —OCO—NRc-, or —NRc-CO—O—, where Rc is hydrogen or a C1-C3 alkyl. In other specific embodiments $Y_4$ is a moiety other than a —CO—O— or —O—CO— moiety. In specific embodiments, $Y_4$ is —NRc-CO—NRc-. In specific embodiments, $Y_4$ is —NH—CO—NH—.

In specific embodiments, $Y_5$ is —O—. In specific embodiments, —$Y_4$-$L_5$-$Y_5$— is —$NR_N$—$(CH_2)_y$—O—, where y is 2-6, and preferably 2-3, and $R_N$ is hydrogen or unsubstituted C1-C3 alkyl group, particularly hydrogen. In specific embodiments, —$Y_4$-$L_5$-$Y_5$— is —$NR_N$CO—$(CH_2)_y$—O—, or —$CONR_N$—$(CH_2)_y$—O—, or —$NR_N$CONR$_N$—$(CH_2)_y$—O—, where y is 2-6, preferably 2-4.

In specific embodiments, —$Y_4$-$L_5$-$Y_5$— is —$NR_N$—$(CH_2)_y$—CO—, where y is 2-6, preferably 2-3, and $R_N$ is hydrogen or unsubstituted C1-C3 alkyl group, particularly hydrogen. In specific embodiments, —$Y_4$-$L_5$-$Y_5$— is —$NR_N$CO—$(CH_2)_y$—CO—, or —$CONR_N$—$(CH_2)_y$—O—, or —$NR_N$CONR$_N$—$(CH_2)y$—O—, where y is 2-6, preferably 2-4.

Boronation reagents of the invention also include:

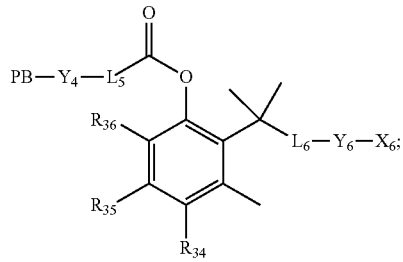

VIIIB

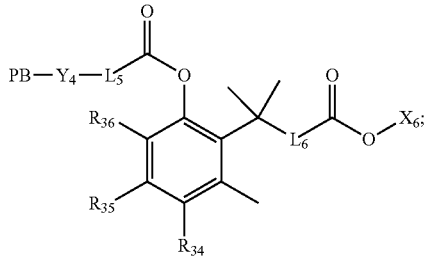

VIIIC

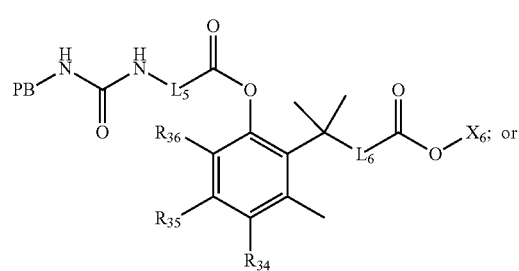

VIIID

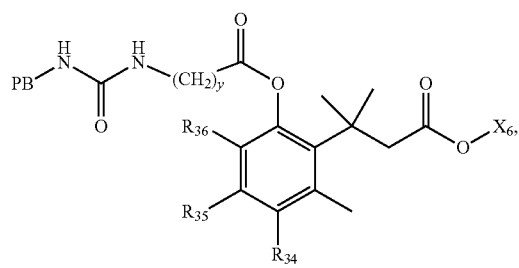

VIIIE where variables are as defined for formula VIIIA. In specific embodiments of formulas VIIIB-VIIIE, $X_6$ is an N-oxido-succinimidyl, a N-oxido-sulfosuccinimidyl group, or a substituted phenolate, including pentafluorophenolate, tetrafluorophenolate, p-nitrophenolate, or p-sulfo-tetrafluorophenolate. In specific embodiments, $R_{34}$-$R_{36}$ are independently a hydrogen, a halide or a C1-C3 alkyl group. In specific embodiments, $R_{35}$ is a methyl group. In specific embodiments, $R_{36}$ is a methyl group. In specific embodiments, $R_{34}$ is hydrogen. In specific embodiments, y is 1-8 or y is 1-3, or y is 1 or 2. In specific embodiments, PB is PB1-PB4 as defined below.

Boronation reagents of the invention further include:

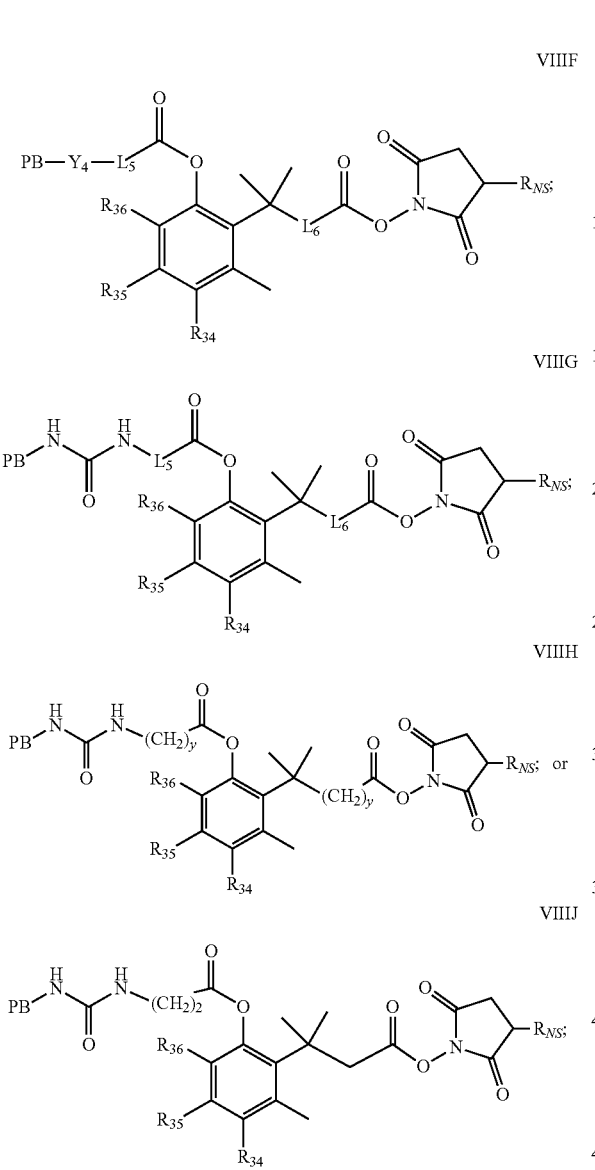

where $R_{NS}$ is hydrogen, $SO_3H$, or $SO_3^-C^+$, where $C^+$ is a cation, particularly an alkali metal cation and more particularly $Na^+$, and other variables are as defined for formula XIIIA. In specific embodiments, $R_{34}$-$R_{36}$ are independently selected from hydrogen, halogen or C1-C8 alkyl or C3-C8 cycloalkyl. In specific embodiments, $R_{34}$-$R_{36}$ are independently selected from hydrogen or a methyl group. In specific embodiments, $R_{34}$ is a hydrogen. In specific embodiments, $R_{36}$ or $R_{35}$ are methyl groups. In specific embodiments, $R_{36}$ is a methyl group and both of $R_{35}$ and $R_{34}$ are hydrogens. In specific embodiments $R_{35}$ is a methyl group and both of $R_{36}$ and $R_{34}$ are hydrogens.

In specific embodiments, reagents of formulas XIIIA-XIIIJ are useful for reaction with amino groups in biological molecules and particularly useful for reaction with amine side chains and the amine terminus of peptides, polypeptides and proteins to introduce one or more phenylboronate groups into the peptide, polypeptide, protein or other biological molecule.

Boronation reagents of this invention further include those of formula XIA:

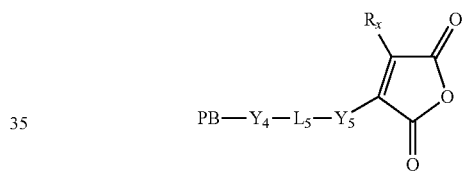

where p-PB is a phenylboronate with the B in the para position with respect to the —$CH_2$—O—, and $X_6$ is a leaving group and —CO—$X_6$ is a reactive group. In specific embodiments, $X_6$ is a leaving group of an activated ester. In specific embodiments, $X_6$ is a nitro- or halogen-substituted phenolate group. In specific embodiments, $X_6$ is an N-oxidosuccinimidyl or a N-oxido-sulfosuccinimidyl group. In specific embodiments, $X_6$ is pentafluorophenolate, tetrafluorophenolate or p-sulfo-tetrafluorophenolate.

These reagents of formula XIA form carbamates on reaction with amino groups, particularly with amino groups of proteins, polypeptides, peptide or other biological molecules. Biological molecules derivatized with these phenylboronate groups undergo oxidative cleavage of the boron bond to the phenyl ring (B—C bond) within cells to form a quinone methide. The quinone methide then breaks down to $CO_2$ and regenerates the amine. These reagents are useful in particularly for reaction with lysine residues of proteins, polypeptides and peptides.

Boronation reagents of the invention also include compounds of formula XA:

$$PB-Y_4-L_5-Y_5 \quad \text{(structure with } R_x \text{ and furandione)}$$

where PB is the phenylboronate group, and $Y_4$, $L_5$ and $Y_5$ are generally as defined herein above and $R_x$ is a hydrogen or an alkyl group, particularly a C1-C3 alkyl group that is unsubstituted.

The reagents of formula XA are useful for bonding phenylboronate groups to biomolecules carrying amino groups, including proteins, polypeptides and peptides. The maleic anhydride of the reagents of formula XA reacts with amino groups to form an amide. At low pH, the proximal carboxylate attacks the amide conjugate to regenerate the reagent and unmodified biomolecule. The phenylboronated biomolecules will be taken up into endosomes of cells which become gradually more acidic, ultimately leading to cleavage of the phenyl boronate groups from the biomolecule.

More specifically for formula XA, $Y_4$ and $Y_5$, are independently a single bond, or a —O—, —S—, —NRc-, —CO—, —O—CO—, —CO—O—, —CO—NRc-, —NRc-CO—, —NRc-CO—NRc-, —OCO—NRc-, —NRc-CO—O—, —N=N—, —N=N—NRc-, —CO—S—, —S—CO—, —S—S—, —$SO_2$—, or —CRc(OH)—CRc(OH)—, where Rc is hydrogen or C1-C3 alkyl; and $L_5$ is a divalent spacer moiety.

In specific embodiments, $L_5$ is selected from:
alkylene linkers (—$(CH_2)_y$—) wherein y is 1-12, and preferably 1-4;
alkoxyalkyl linkers —$[(CH_2)_q$—O—$(CH_2)_r]_a$— wherein q and r are zero or integers from 1-4, preferably 0, 1, 2 or 3, as long as one of q and r is not zero, and a is 1-6, preferably 2-4; or aminoalkyl linkers —[(CH$_2$)s-NR$_N$—(CH$_2$)$_t$]$_b$— wherein R$_N$ is hydrogen or a C1-C3 alkyl group, s and t are 0 or integers from 1-4, and are preferably 0, 1 or 2 as long as one of s and t is not zero, and b is 1-3 and preferably is 1.

In specific embodiments, R$_x$ is hydrogen. In specific embodiments R$_x$ is a methyl group.

In specific embodiments, —Y$_4$-L$_5$-Y$_5$— is —NR$_N$—(CH$_2$)$_t$, where t is 1-4. In specific embodiments, —Y$_4$-L$_5$-Y$_5$— is —NH—(CH$_2$)$_t$, where t is 1-4 and in particular where t is 1. In specific embodiments, —Y$_4$-L$_5$-Y$_5$— is —NR$_N$CO—(CH$_2$)$_y$, where t is 1-4. In specific embodiments, —Y$_4$-L$_5$-Y$_5$— is —CONR$_N$—(CH$_2$)y, where y is 1-4. In specific embodiments, —Y$_4$-L$_5$-Y$_5$— is —NR$_N$-CONR$_N$—(CH$_2$)$_y$, where y is 1-4. In specific embodiments, —Y$_4$-L$_5$-Y$_5$— is —O—(CH$_2$)$_r$, where r is 1-4 and in particular where r is 2 or 3.

In specific embodiments, Y$_6$—X$_6$ together is a reactive group that reacts with one or more of an amino group, a carboxylic acid group or ester thereof, a sulfhydryl group, a hydroxyl group, an azide group, a thioester group, a phoshinothioester group, an aldehyde group or a ketone group of an amino acid, peptide or protein.

Phenylboronate groups (PB) are phenyl groups carrying a —B(OH)$_2$, —B(OH)(OR) or a

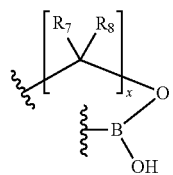

moiety bonded at adjacent carbons of the phenyl ring, where R is an optionally substituted aliphatic group which optionally links to the phenyl ring to form a 5- or 6-member boroxole ring.

Additional phenylboronates are phenyl groups carrying a —B(OR$_B$)$_2$ where each —R$_B$ is an optionally substituted aliphatic group or optionally substituted heteroaliphatic group, particularly an optionally substituted alkyl group, wherein the two RB are optionally linked together to form an optionally substituted 5- to 8-member heteroaliphatic ring. In a specific embodiment, the —B(OR$_B$)$_2$ group is:

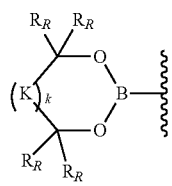

where each R$_R$ is independently hydrogen or alkyl, particularly a C1-C3 alkyl group, k is 0 or 1 and K is selected from an optionally substituted divalent aliphatic or an optionally substituted divalent heteroaliphatic moiety having 1 to 3 atoms in the divalent aliphatic or heteroaliphatic moiety. When k is 0 there is a single bond between the carbons in the ring. In specific embodiments, K is selected from —(CH$_2$)$_{1-3}$—, —(CH$_2$)$_{1-2}$—O—, —CH$_2$—O—CH$_2$—, —O—(CH$_2$)$_{1-2}$—, —(CH$_2$)$_{1-2}$—NR$_R$—, —CH$_2$—NR$_R$—CH$_2$—, —NR$_R$—(CH$_2$)$_{1-2}$—, —(CH$_2$)$_{1-2}$—S—, —CH$_2$—S—CH$_2$—, or —S—(CH$_2$)$_{1-2}$—, where each carbon of the K moiety is independently optionally substituted, particularly with one or two —R$_R$ groups. In preferred embodiments, k is 0 and the boronate group has a 5-member ring:

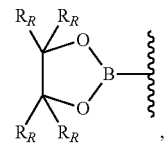

where R$_R$ is as defined above, but in specific embodiments all R$_R$ are methyl groups or all R$_R$ are hydrogen. In other embodiments, k is 1 and K is:
—[C(R$_R$)$_2$]$_{1-3}$—, —(CH$_2$)—, —(CH$_2$)$_2$— or —(CH$_2$)$_3$—, —(CH$_2$)$_2$—NR$_R$—(CH$_2$)$_2$—, or —(CH$_2$)$_2$—N(CH$_3$)—(CH$_2$)$_2$—.

Specific PB include:

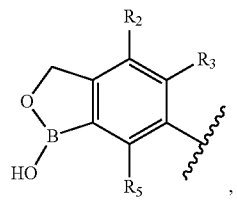

PB1

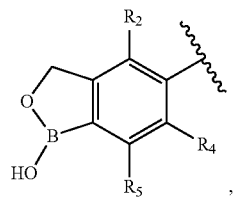

PB2

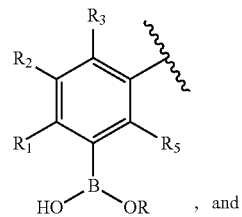

PB3

, and

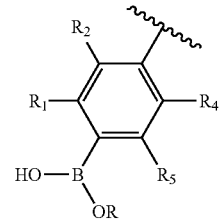

PB4 wherein: x, R$_1$-R$_5$, R$_7$, R$_8$ and R are as defined in formula IA and IB above. In specific embodiments, R$_1$-R$_5$ are all hydrogen. In specific embodiments, R$_7$ and R$_8$ are hydrogens. In specific embodiments, x is 1.

In a specific embodiment of formula PB1, R$_2$, R$_3$ and R$_5$ are all hydrogen. In a specific embodiment of formula PB2, R$_2$, R$_4$ and R$_5$ are all hydrogen. In a specific embodiment of formula PB3, R$_1$, R$_3$ and R$_5$ are all hydrogen and R$_2$ is hydrogen or a halogen. In a specific embodiment of formula PB4, R$_1$, R$_4$ and R$_5$ are all hydrogen and R$_2$ is hydrogen or a halogen. In a specific embodiment of formula PB3 $R_1$-$R_3$, and $R_5$ are all hydrogen. In a specific embodiment of formula PB3 $R_1$-$R_3$ are all hydrogen. In a specific embodiment of formula PB3, R is a —CO—$R_E$, where $R_E$ is hydrogen, a $C_1$-$C_{12}$ alkyl group (preferably C1-C6 alkyl group), an optionally substituted phenyl, or an optionally substituted benzyl group. In a specific embodiment of formula PB4, $R_1$-$R_2$, $R_4$-$R_5$ and R are all hydrogen. In a specific embodiment of formula PB4, $R_1$-$R_2$, and $R_4$-$R_5$ are all hydrogen. In a specific embodiment of formula PB4, R is a —CO—$R_E$, where $R_E$ is hydrogen, a $C_1$-$C_{12}$ alkyl group (preferably C1-C6 alkyl group), an optionally substituted phenyl, or an optionally substituted benzyl group.

In another embodiment, PB is the group PB5 having formula:

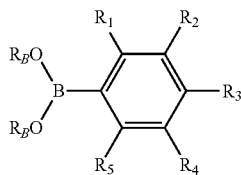

where $R_1$-$R_5$ are as defined for formulas IA and IB above, but wherein one of $R_1$-$R_5$ is a bond or a divalent moiety for bonding directly or indirectly through one or more linkers to a reactive group. For example, PB5 includes among others:

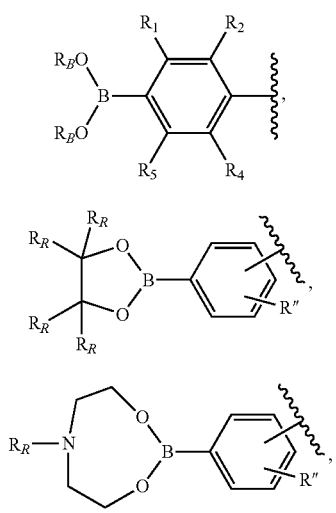

In a specific embodiment of PB5, four of $R_1$-$R_5$ are hydrogens or alkyl groups. In a specific embodiment of PB5, four of $R_1$-$R_5$ are hydrogens and one of the remaining $R_1$-$R_5$ is a single bond or a $Y_4$ or $L_5$ group. In a specific embodiment of PB5, one of $R_1$-$R_5$ is a halogen, particularly a chlorine or a bromine, and one of the remaining $R_1$-$R_5$ is a single bond or a $Y_4$ or $L_5$. In a specific embodiment of PB5, $R_2$ is a halogen and $R_3$ is a single bond or a $Y_4$ or $L_5$ group. In PB5B and PB5C, R" represents 1-4 $R_R$ on any four ring positions with one ring position being a single bond or a divalent moiety for attachment via one or more linkers to a reactive group. In a specific embodiment of PB5B, all of $R_R$ are methyl groups or all of $R_R$ are hydrogens. In a specific embodiment of PB5B or PB5C, R" are hydrogen or methyl groups or all of R" are hydrogen. In a specific embodiment of PB5B or PB5C, three of R" are hydrogen and one of R" is halogen.

PB5A and PB5B and PB5C groups where the single bond is in the para position from the boron group are particularly useful in reagents of formula XIA above to form quinone methides on oxidation once inside a cell.

Boronation reagents of this invention further include:

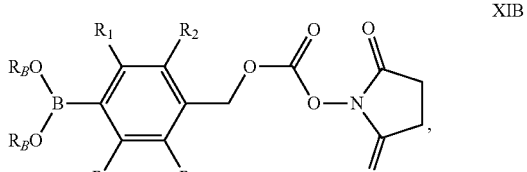

XIB

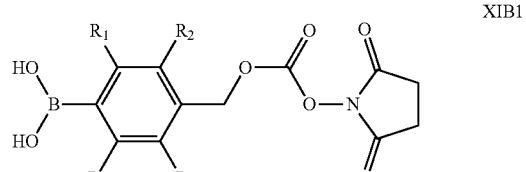

XIB1

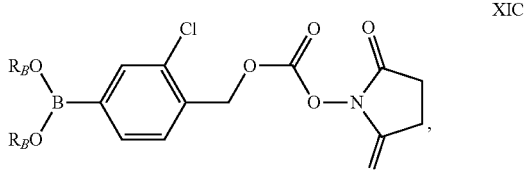

XIC

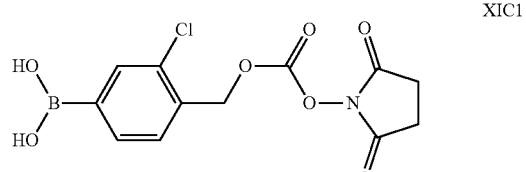

XIC1

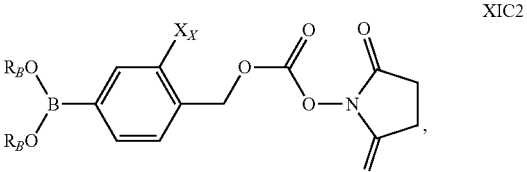

XIC2

XIC2, where $X_x$ is a halogen

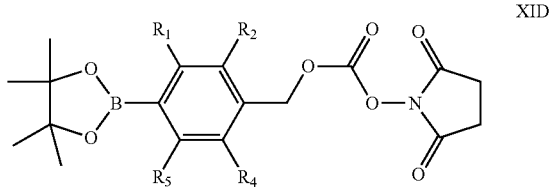

XID

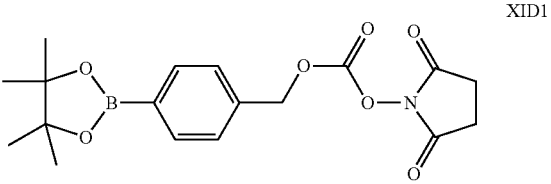

XID1

-continued

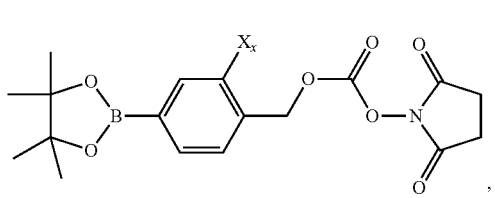
XID2 where $X_x$ is a halogen, wherein $R_1$, $R_2$, $R_3$ and $R_4$ are as defined for formulas IA and IB above. In specific embodiments, $R_1$, $R_2$, $R_3$ and $R_4$ are selected from hydrogen, C1-C3 alkyl, or halogen. In specific embodiments, all of $R_1$, $R_2$, $R_3$ and $R_4$ are hydrogens.

Boronation reagents of the invention further include:

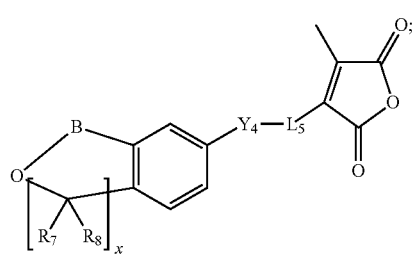
XB

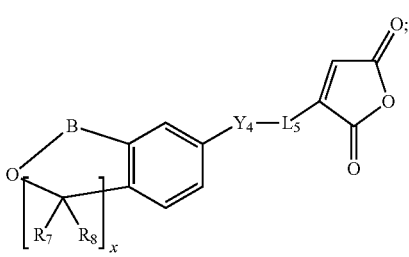
XB1

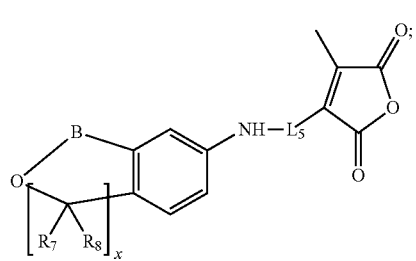
XC

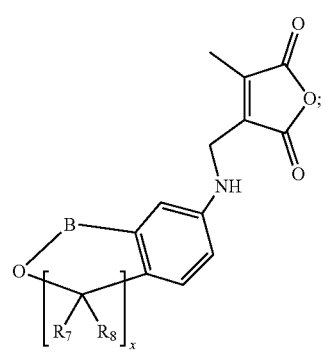
XD

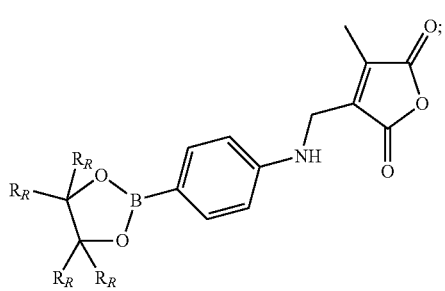
XE

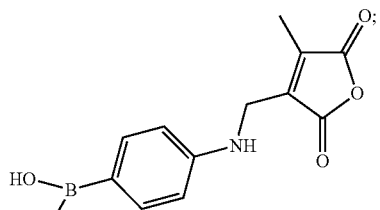
XF

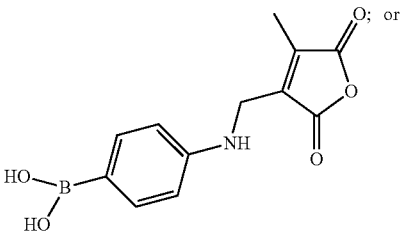
XG

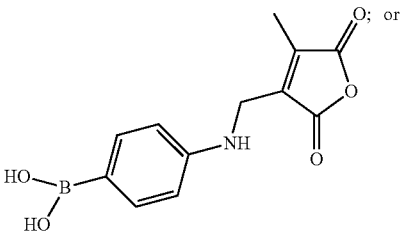
XG1 where variables are as defined above for formula XA.

Figure 24:
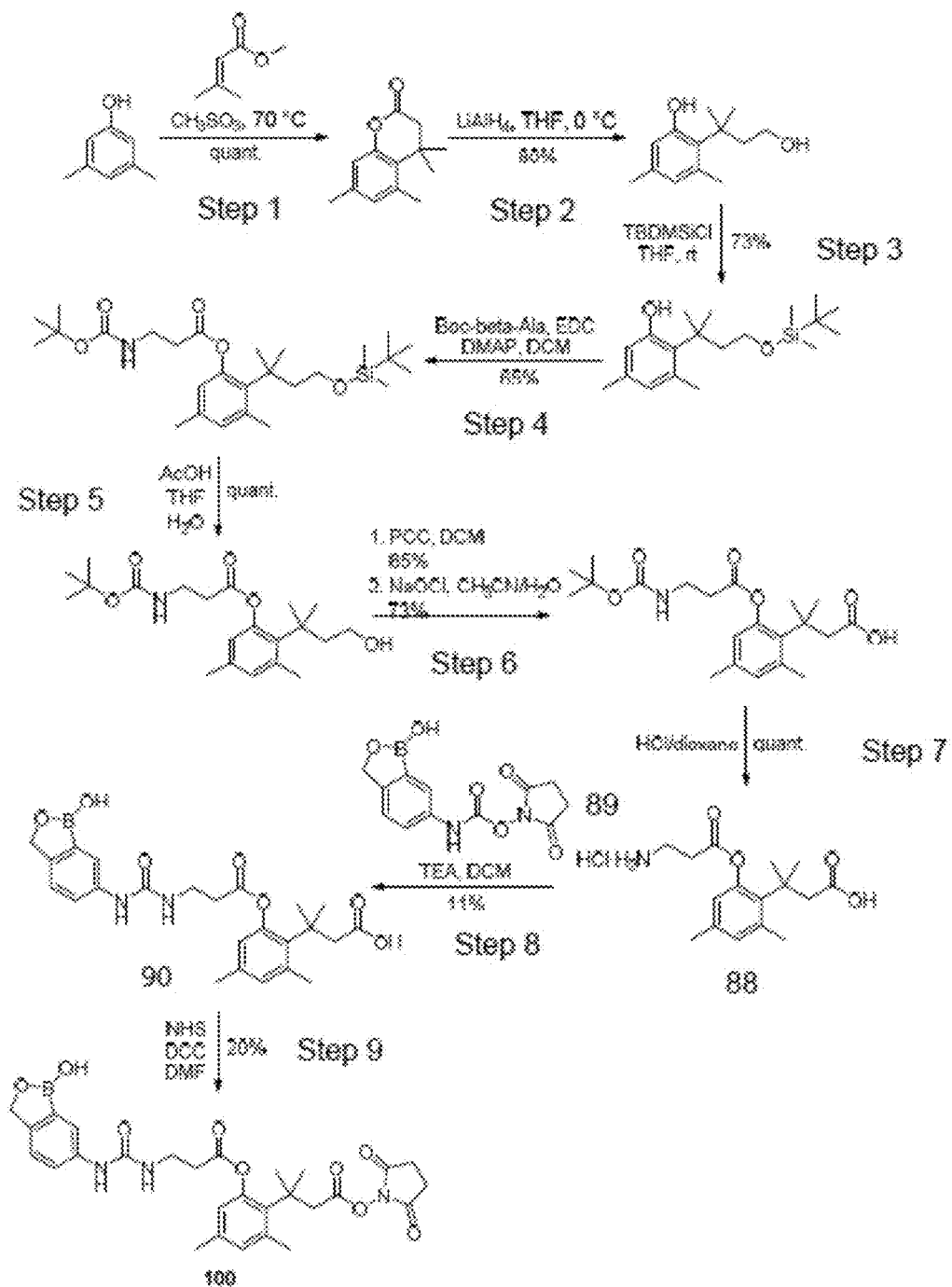
FIG. 24 is a scheme illustrating the synthesis of an exemplary boronation reagent which is bioreversable.
Figure 25:
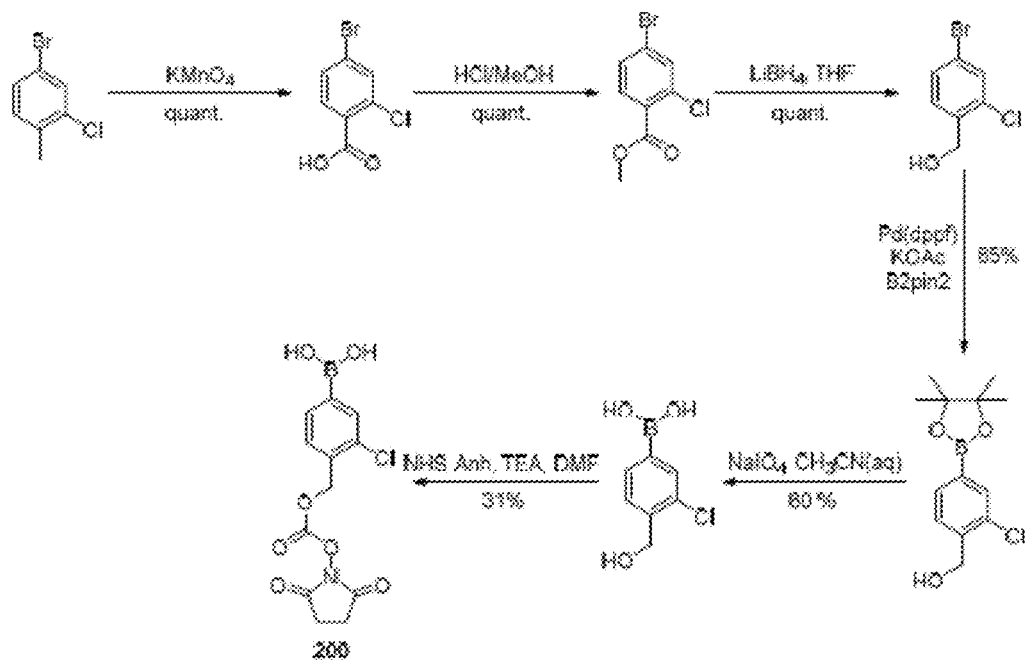
FIG. 25 is a scheme illustrating the synthesis of an exemplary boronation reagent which is bioreversible.
Figure 26:
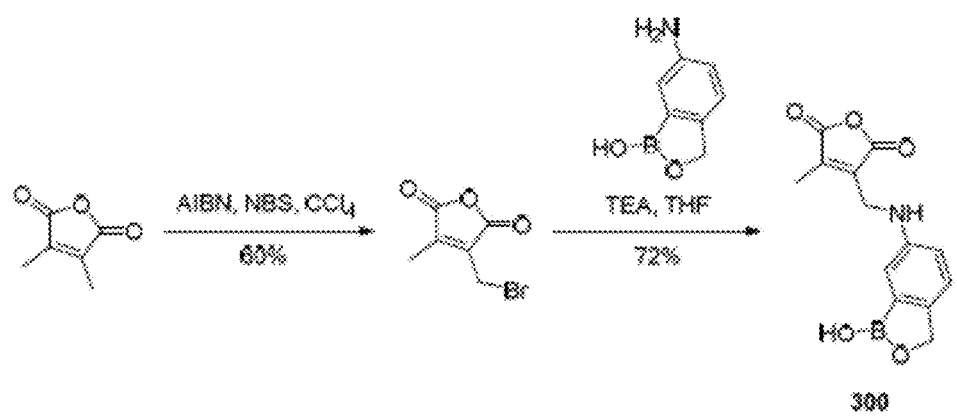
FIG. 26 is a scheme illustrating the synthesis of an exemplary boroantation reagent which is bioreversible.

In specific embodiments, boronation reagents of the invention are compounds 100, 200 or 300 as illustrated in FIGS. 24-26, respectively.

Boronation reagents of formulas VIIIA-VIIIH can be prepared as illustrated in the Scheme of FIG. 24 or by routine adaptation of this method, for example, by choice of starting materials or reagents. Boronation reagents of formulas X1A, X1B, XIB1, XIC, XIC1, XIC2, XID, XID1, and XID2 can be prepared as illustrated in the Scheme of FIG. 25 or by routine adaptation of this method, for example, by choice of starting materials or reagents. Boronation reagents of formulas XIA, XIB, XIB1, XIC, XIC1, XIC2, XID, XID1, and XID2 can be prepared as illustrated in the Scheme of FIG. 25 or by routine adaptation of this method, for example, by choice of starting materials or reagents. Boronation reagents of formulas XA, XB, XB1, XC, XD, XE, XF, XG1, and XG2 can be prepared as illustrated in the Scheme of FIG. 26 or by routine adaptation of this method, for example, by choice of starting materials or reagents. Additional synthetic methods useful in the synthesis of boronation reagents of this invention are found in U.S. Pat. Nos. 7,442,764, 7,842,823 and 8,637,490, each of which is incorporated by reference herein for descriptions of synthesis of phenylboronate compounds.

The schemes of FIGS. 24-26 employ the following abbreviations:

DMAP is 4-dimethylaminopyridine; EDC is 1-ethyl-3-(3-dimethylaminopropyl)-carbodiimide; DCC is dicyclohexyl-carbodiimide; DCM is (dichloromethane); PCC is pyridinium chlorochromate; NHS is N-hydroxysuccinimide; TEA is triethylamine; AIBN is 2,2'-azobis(2-methylpropionitrile); B+NBS is N-bromosuccinimide; TBDMSiCl is t-butyldimethylsilyl chloride; Pd(dppf) is 1,1'-Bis(diphenyl-phosphino)ferrocene]-palladium(II), typically the dichloro-paladium; KOAC is potassium acetate; B2pin2 is bis[pinacolato]diboron.

Boronation reagents as described herein can be employed to add phenyl boronate groups, as defined herein, to an amino acid, particularly lysine with respect to amine-reactive boronation reagents, to a peptide, an oliogpeptide, a polypeptide or a protein or other biological molecule. The boronation reagents herein can be used to add 1 or more phenylboronate groups to such molecules. For example, boronation reagents can be used to derivatize carboxylic acid (or ester) groups or amino groups in a peptide, an oliogpeptide, a polypeptide or a protein or other biological molecule.

In specific embodiments, one to all of the amino groups in such cargo molecules can be reversibly derivatized using the boronation reagents of this invention. In specific embodiments, cargo molecules are derivatized with 1-10 phenyl boronate groups, or 1-5 phenylboronate groups, or 2-7 phenylboronate groups, or 2-5, phenyl boronate groups. In specific embodiments, cargo molecules are derivatized with 2 phenylboronate groups employing the boronation reagents of this invention. In specific embodiments, the boronation reagents of formulas VIIIA, XIA and XA are employed to prepare boronated lysines.

In a related embodiment, the invention provides a phenylboronated oligopeptide for ligation to, binding to or crosslinking with a cargo molecule, such as a nucleic acid, peptide or protein and the boronated peptide or protein which is ligated, bound to or crosslinked with the phenylboronated oligopeptide. In specific embodiments, the phenylboronated oligopeptide contains 2-30 amino acids, contains 2-20 amino acids, contains 2-15 amino acids or contains 5-10 amino acids. In specific embodiments, 75% or fewer of the amino acids of the oligopeptide are boronated. In additional embodiments, 50% or fewer, 25% or fewer or 10% or fewer of the amino acids of the oligopeptide are boronated. In specific embodiments, a phenylboronate group is bonded to an amino acid side group of one or more amino acids of the oligopeptide. In a specific embodiment, a phenylboronate group is bonded to the N-terminus of the oligopeptide. In a specific embodiment, a phenyl boronate is bonded to the C-terminus of the oligopeptide. Phenylboronated oligopeptides include those in which one or more phenylboronated amino acid, such as a boronated glutamate, aspartate, phenyl alanine or lysine alternate in the oligopeptide with one or more non-boronated amino acid, such as glycine or leucine.

Phenylboronated oligopeptides include those containing one or more phenylboronated amino acids, such as a boronated glutamate, aspartate, phenyl alanine or lysine, wherein each boronated amino acid is spaced from other boronated amino acids by one or more non-boronated amino acids, such as a glycine. In such embodiments, the phenylboronate groups may extend over the length of the oligopeptide. In other embodiments, the phenylboronate groups may be located on adjacent amino acids at one end of the oligopeptide, for example at or near the end distal to the site of attachment of the oligopeptide to the peptide or protein.

Any amino acid that is known in the art to be useful in the synthesis of oligopeptides may be employed in the oligopeptides of this invention. Amino acids include any naturally-occurring amino acids or any non-naturally occurring (synthetic) amino acids, and any amino acids occurring in peptides or proteins in nature.

In a specific embodiment, the invention provides a phenylboronated oligopeptide reagent containing a ligand group, such as biotin or a functional derivative thereof. The reagent generically has the formula:

T-L-phenylboronated oligopeptide(where T-L may be at the N-terminus or C-terminus of the oligopeptide).

where T is a ligand group that binds to a cargo molecule, such as a nucleic acid, peptide or protein or a reactive group X (as defined above) that reacts with a reactive group of a cargo molecule, such as a nucleic acid, peptide or protein, particularly that is an amine-reactive, a carboxyl-reactive, a sulfhydryl-reactive, a hydroxyl-reactive, an aldehyde- or ketone-reactive group, an azide-reactive, a thioester reactive or a phosphinothiol reactive group and L is an optionally spacer moiety (as defined above).

On binding to or reacting with a cargo molecule, such as a nucleic acid, peptide or protein, the cargo molecule carries one or more boronated oligopeptide tags: Protein (-T1-L-boronated oligopeptide)$_z$, where z is 1-12 or more and preferably z is 1-6.

In a specific embodiment, the oligopeptide or oligopeptide reagent comprises 2-20 amino acids of which at least two amino acids are boronated as described herein. In more specific embodiments, the oligopeptide carries 3-12 phenylboronate groups. In a specific embodiment, the peptide contains 1-12 amino acids with side groups having an —NH$_2$ group. In a specific embodiment, the peptide contains 1-12 amino acids with side groups having an —COOH group.

In a specific embodiment, T is a ligand which binds to a selected nucleic acid or protein. In a specific embodiment T is biotin or a derivative thereof. Various functional biotin derivatives are known in the art and a number are commercially available. For example, biotin can be readily transformed at its carboxyl terminus for attachment to numerous species. Further, a variety of biotinylation reagents are known in the art which can be employed in preparation of boronated oligopeptide reagents of this invention.

In a specific embodiment, T is a group that can function for peptide ligation to form a peptide bond between the peptide or protein and the boronated oligopeptide. This group may be selected from —NH$_2$, —COOH or an activated ester, a thioester, an azide, a phosphinothioester or the like.

In specific embodiments, spacer groups for phenylboronate compounds and for boronated oligopeptides include among others:

an alkylene chain having 1-20 and preferably 3-10 carbon atoms, an alkyloxylene chain having 1-20 carbon and oxygen atoms and preferably 5-12 carbon or oxygen atoms (an alkylene chain in which one or more non-adjacent CH$_2$ moieties are replaced with —O—);

an acetoxymethyl ether moiety;

an alkylthiolene chain having 1-20 carbon and sulfur atoms and preferably 5-12 carbon or sulfur atoms (an alkylene chain in which one or more non-adjacent $CH_2$ moieties are replaced with —S—); or an alkylaminolene chain (i.e., a divalent alkylene chain in which one or more non-adjacent $CH_2$ moieties are replaced with —NRc-) having 1-20 carbon and nitrogen atoms and preferably 5-12 carbon or nitrogen atoms where Rc is hydrogen or a C1-C3 alkyl group, a 5- or 6-member divalent alicyclic, heterocyclic, aryl or heteroaryl ring moiety, one or two alkylene moieties linked to a 5- or 6-member alicyclic, heterocyclic, aryl or heteroaryl ring moiety.

In specific embodiments, phenylboronate compounds of this invention contain a reactive functional group for attachment of the phenylboronate to a nucleic acid, an amino acid, peptide or protein. The reactive functional group can, for example, be a group that reacts with an amino, a carbonyl, a carboxylate, a carboxylic ester, a sulfhydryl or a hydroxyl group. Preferably such reactive groups react to attach the phenylboronate to the nucleic acid, amino acid, peptide or protein under conditions such that the phenylboronate substantially retains sugar binding activity and which do not substantially detrimentally affect the biological activity of interest of the amino acid, peptide or protein. In a specific embodiment, the phenyl boronate contains an amine reactive group for bonding to an amino group of a nucleic acid base. A variety of reactive groups useful for coupling to a nucleic acid, nucleoside, peptide or protein are known in the art and one of ordinary skill in the art can select among such known reactive groups to practice the methods of the present invention without undo experimentation.

An overview of bioconjugation methods that can be employed for boronation of peptides and proteins is found in Hermanson, G. T. *Bioconjugation Techniques* ($2^{nd}$ Ed.) 2008 Academic Press/Elsevier London, UK. This reference also contains detailed descriptions of homobifunctional and heterobifunctional crossing linking reagents which can be employed to covalently attach a phenylboronate group to an amino acid, peptide or protein.

Amine-reactive groups are exemplified by a carboxylate group, a carboxylate ester group, an acid chloride group, an aldehyde group, an acyl azide group, an epoxide, an isothiocyanate group, an isocyanate group, an imidoester group or an anhydride group. Amines react with carboxylates in the presence of coupling reagents, such as carbodiimides. Amine-reactive groups include active carboxylic acid ester groups, such as succinimidyl ester groups or sulfosuccinimidyl ester groups (e.g., N—OH succinimidyl or N—OH sulfosuccinimidyl groups); haloalkyl ester groups, such as trifluoroalkyl ester groups and hexafluoroalkyl ester groups; halophenyl ester groups, particularly fluorophenyl and chlorophenyl ester groups, including penta- and tetrafluorophenyl ester groups, pentachlorophenyl ester groups; nitrophenyl ester groups, including 2-nitrophenyl, 4-nitrophenyl and 2,4-dinitrophenyl ester groups; as well as other substituted phenyl ester groups, including sulfodichlorophenol ester groups.

Figure 8:
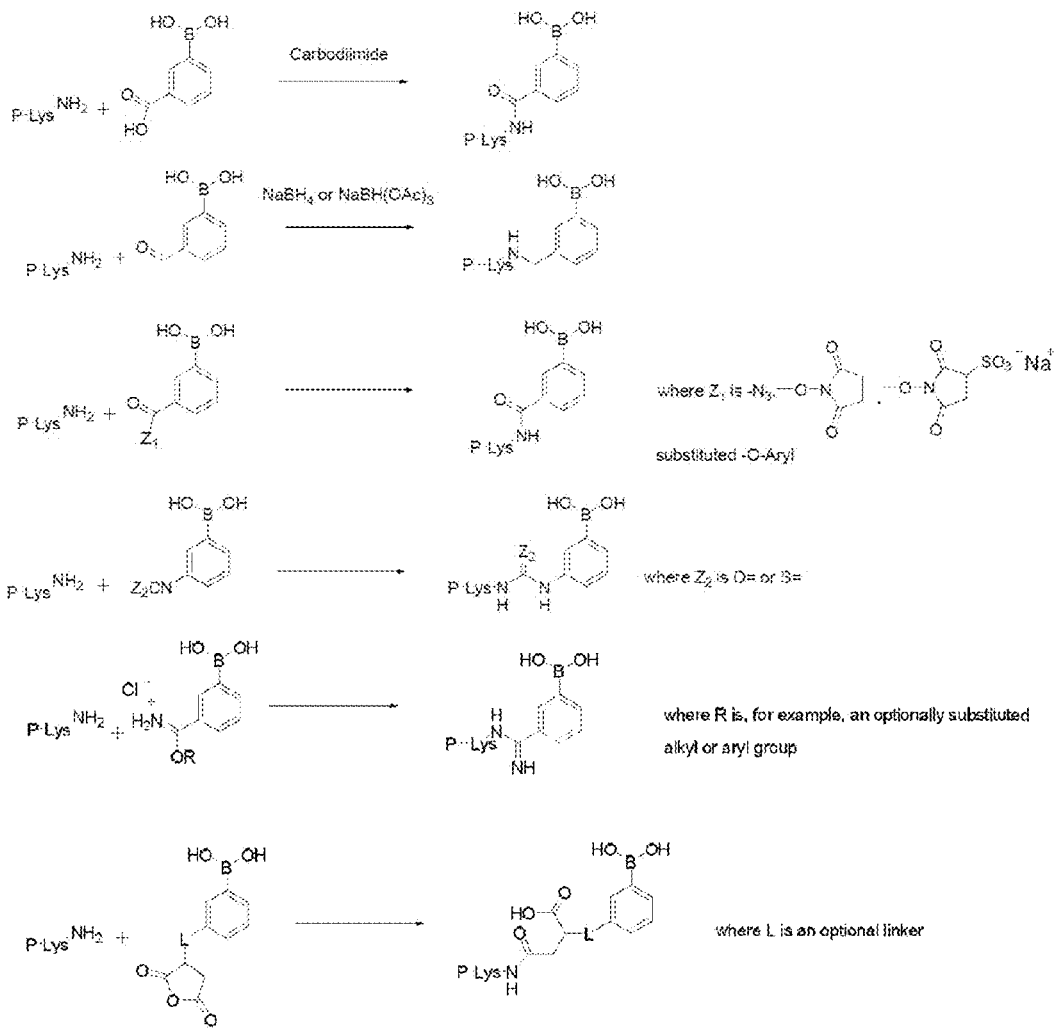
FIGS. 8-12 illustrate exemplary reactive groups and exemplary reactions that can be employed to boronate peptides or proteins with phenylboronic acids. 2-substituted phenylboronic acid is used in these figures to illustrate exemplary reactions. The exemplified reactive groups can be substituted on other ring positions of the phenylboronic acid and other ring positions may be further substituted as described herein. Additionally, analogously substituted phenylboroxoles can be used to boronate peptides and proteins. Examples are given in which the reactive group is directly bonded to the ring of the phenylboronic acid and in which the reactive group is indirectly attached to the phenylboronic acid via a spacer moiety. It will be appreciated by one of ordinary skill in the art that a variety of art-known linking moieties can be employed which are suitable for boronation of peptides and proteins using the illustrated reactions.

Examples of amine-reactive groups and their reactions with amino groups are provided in FIG. 8. For example, carboxylate-substituted phenylboronic acid can be coupled to an amino group of an amino acid, peptide or protein to form an amide linkage employing a coupling agent, such as a carbodiimide. A formyl-substituted phenylboronic acid can be reacted with an amino group of an amino acid, peptide or protein by reductive amination forming a —NH—$CH_2$— linkage. An acylazide-substituted phenylboronic acid can be coupled to an amino group of an amino acid, peptide or protein to form an amide linkage. A phenylboronate substituted with an activated ester —COO—$Z_1$ reactive group can be reacted with an amino group of an amino acid, peptide or protein forming an amide linkage. A phenylboronate substituted with an isocyanate or a isothiocyanate reactive group can be reacted with an amino group of an amino acid, peptide or protein forming a urea or thiourea linkage, respectively. A phenylboronate substituted with an anhydride group, such as a maleic anhydride group can be reacted with an amino group of an amino acid, peptide or protein forming an amide bond where at least a portion of the anhydride forms a spacer between the phenylboronate and the amino group. An imidoester-substituted phenylboronate can be reacted with an amino group of an amino acid, peptide or protein forming an amidine linkage. Reactions analogous to those shown in FIG. 8 can be used to couple the phenylboronate to an amino group of a nucleic acid.

General conditions for carrying out reactions between amine-reactive groups and amino groups of a nucleic acid, an amino acid, peptide or protein are well known in the art and can be carried out by one of ordinary skill in the art without undue experimentation. As illustrated in FIG. 8, the reactive group can be a substituent on the phenyl ring of the phenylboronate or can be contained in the substituent. The reactive groups exemplified in FIG. 8 can also be linked to the phenyl ring of the phenylboronate by a spacer moiety L, such as described herein. It will be appreciated that it may be useful to protect the —$B(OH)_2$ group of the phenylboronate while carrying out such reactions with amino groups. Useful protecting groups for the —$B(OH)_2$ are known in the art, for example, pinacol, perfluoropinacol, pinanediol, ethylene glycol, diethylene glycol, catechol, 1,2-cyclohexanediol, 1-3-propanediol, 2,3-butanediol, glycerol, neopentylglycol, diethanolamine, N-methyldiethanolamine, and 1-(4-methoxyphenyl)-2-methylpropane-1,2-diol can be employed. See for example, Yan J. et al. (2005) [23].

Figure 9:
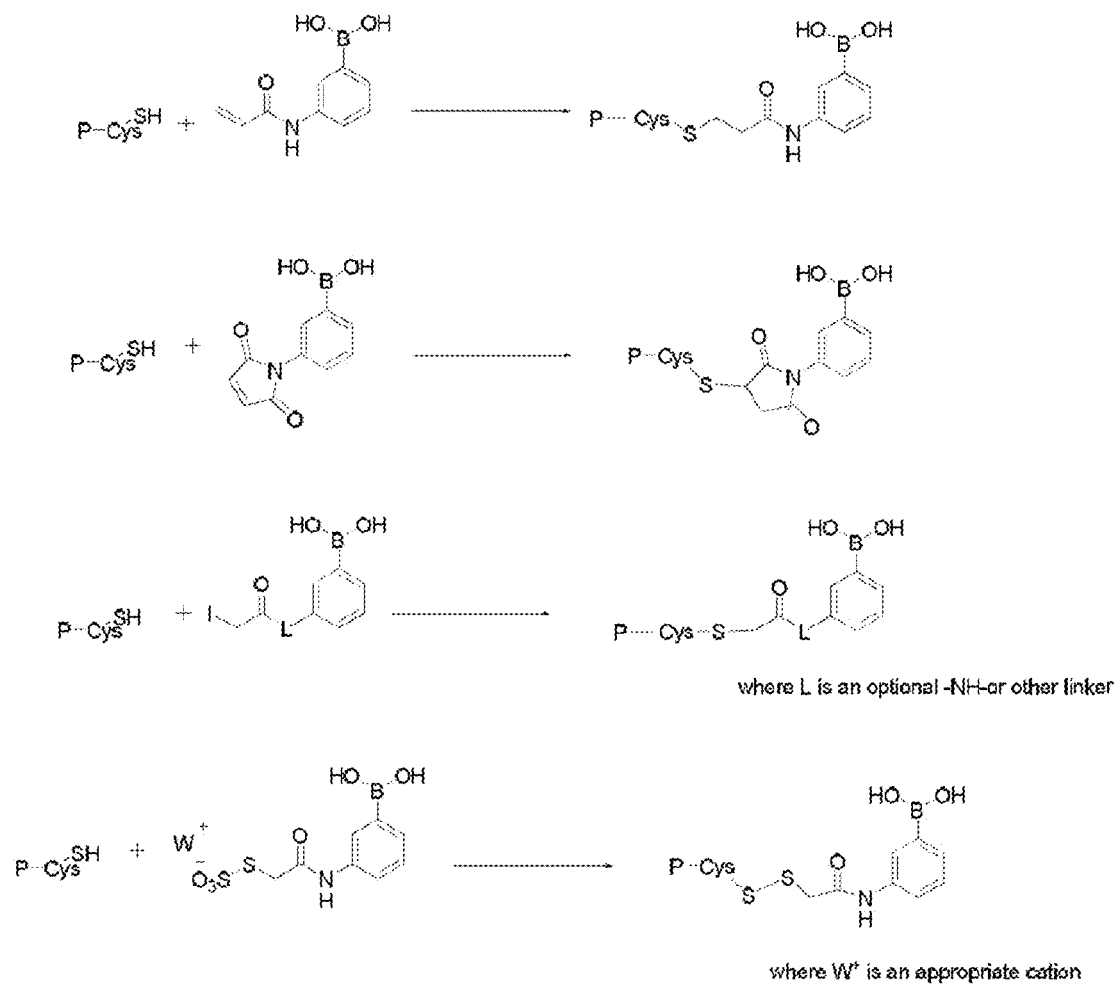

Sulfhydryl-reactive groups are exemplified by haloacetyl and haloacetamidyl groups, particularly iodoacetyl and bromoacetyl or corresponding acetamidyl groups, maleimide groups, haloalkyl groups, halobenzyl groups, acryloyl groups, epoxide groups, groups that undergo thiol-disulfide exchange, such as dipyridyl disulfide groups or 2,2'-dihydroxy-6,6'-dinaphthyldisulfide groups, or thiosulfate groups. Exemplary sulfhydryl-reactive groups are provided in FIG. 9 where the linkages formed are illustrated, for example —S—$CH_2$—$CH_2$—, —S—$CH_2$—CHR—, or —S—S— linkages can be formed (where R depends upon the reactive group employed). General conditions for carrying out reactions between sulfhydryl-reactive groups and sulfhydryl groups of an amino acid, peptide or protein are well known in the art and can be carried out by one of ordinary skill in the art without undue experimentation. As illustrated in FIG. 9, the reactive group can be a substituent on the phenyl ring of the phenylboronate or can be contained in the substituent. The reactive groups exemplified in FIG. 9 can also be linked to the phenyl ring of the phenylboronate by a spacer moiety L, such as described herein. It will be appreciated that it may be useful to protect the —$B(OH)_2$ group of the phenylboronate while carrying out such reactions with sulfhydryl groups. Useful protecting groups for the —$B(OH)_2$ are known in the art as described hereinabove.

Figure 10:
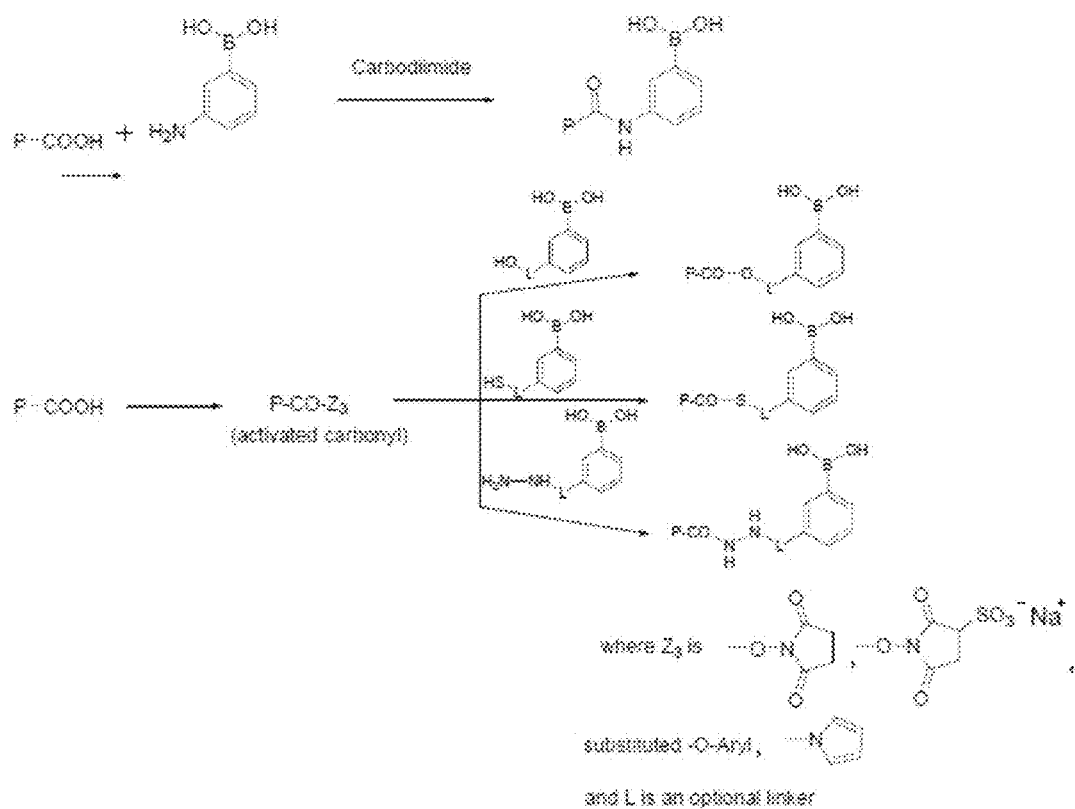

Carboxylate-reactive functional groups are exemplified by amines (e.g., employing a carbodiimide), hydrazine groups, hydrazide groups, sulfonylhydrazide groups, diazoalkyl groups, diazoaryl groups, diazoacetyl groups, hydroxyl groups or sulfhydryl groups. FIG. 10 illustrates coupling of an amino substituent on a phenylboronate with a carboxylic acid group of an amino acid, peptide or protein (P—COOH) employing a coupling reagent such as a carbodiimide. FIG. 10 also illustrates an alternative reaction where the carboxylate group is activated, for example by formation of an active ester or by reaction with carbonyl diimidazole to form an activated carbonyl followed by reaction with a hydroxyl group to form an ester, a sulfhydryl group to form a thioester or a hydrazine to form a hydrazide. As illustrated in FIG. 10, the carboxylate-reactive group can be linked to the phenyl ring of the phenylboronate by a spacer moiety L, such as described herein. Alternatively, the reactive group can be substituted directly on the phenyl ring of the phenylboronate. It will be appreciated that it may be useful to protect the —B(OH)$_2$ group of the phenylboronate while carrying out such reactions with carboxylate groups. Useful protecting groups for the —B(OH)$_2$ are known in the art as described hereinabove.

Figure 11:
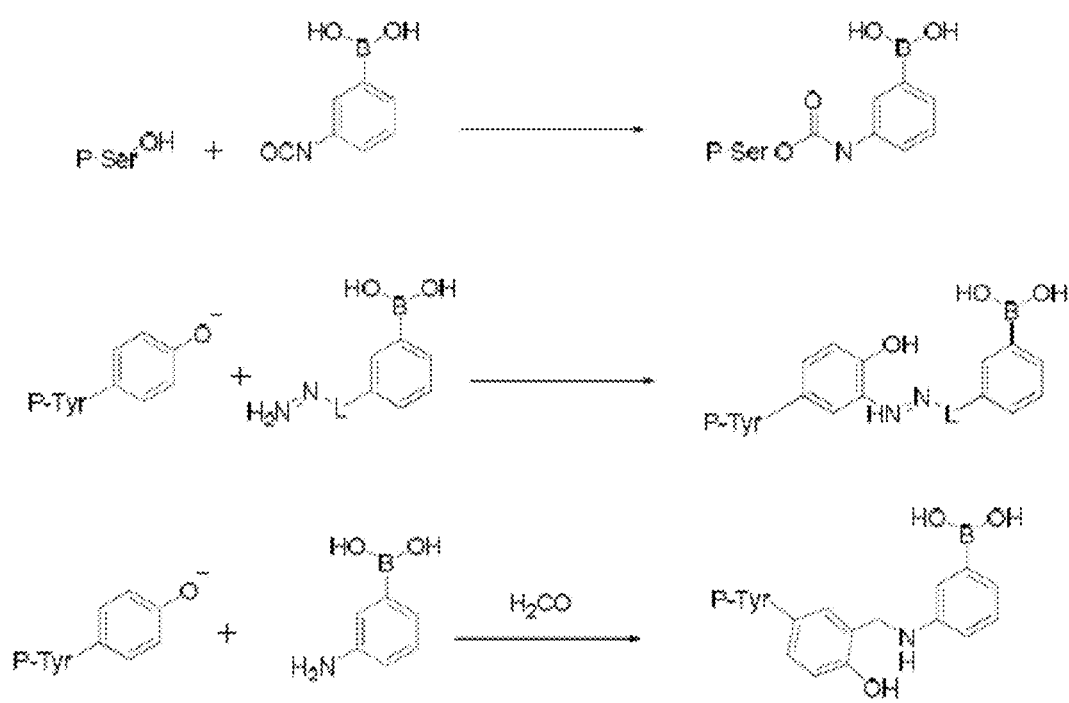

Hydroxyl-reactive functional groups are exemplified by isocyanate groups; epoxide groups; alkyl or aryl halide group, e.g., a halotrityl group; an activated carbamate group, an activated ester group (such as described above), N,N'-disuccinimidyl carbonate groups or N-hydroxysuccinimidyl chloroformate groups. FIG. 11 illustrates reaction of the hydroxyl group of a serine which may be in a peptide or protein with an isocyanate-substituted phenylboronate to form an —OCO—N— linkage. Terminal serines can be treated with periodate to generate an aldehyde which can then be reacted with hydrazine groups, hydroxylamine groups, or amino groups. The hydroxyl group (phenolate) of a tyrosine residue can react with an acylating or alkylating agent forming an ester or ether, respectively, with a diazonium group to form a diazo compound or with an amino group in the presence of an aldehyde (e.g., formaldehyde or glutaraldehyde) to form a Mannich condensation product as also illustrated in FIG. 11. As shown in FIG. 11, the reactive group can be a substituent on the phenyl ring of the phenylboronate. Alternatively the hydroxyl-reactive group can also be linked to the phenyl ring of the phenylboronate by a spacer moiety L, such as described herein. It will be appreciated that it may be useful to protect the —B(OH)$_2$ group of the phenylboronate while carrying out such reactions with carboxylate groups. Useful protecting groups for the —B(OH)$_2$ are known in the art as described hereinabove.

Figure 12:
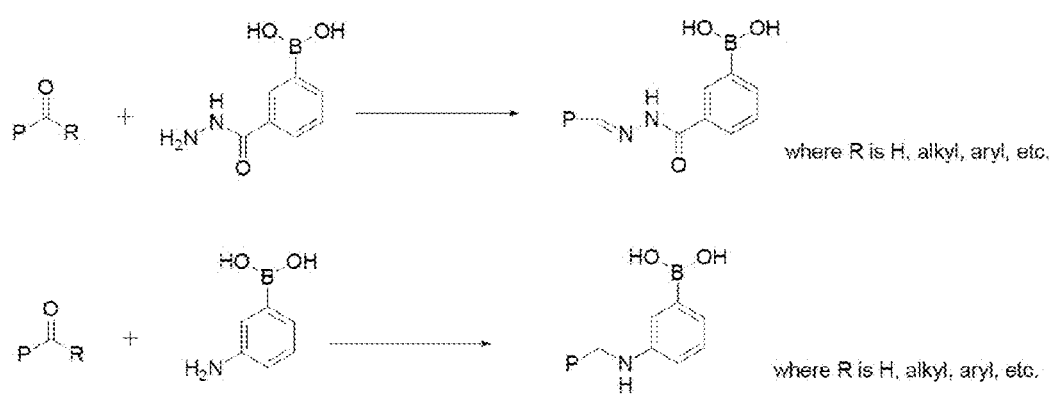

Aldehyde and ketone-reactive groups are exemplified by hydrazine groups and derivatives thereof including hydrazides, semicarbazides and carbohydrazides, and amino groups. Various methods for introduction of aldehyde and ketone groups into amino acids, peptides and proteins are known in the art. For example, N-terminal serine and threonines can be oxidized using periodate to form aldehyde groups. As illustrated in FIG. 12, an aldehyde or ketone group of an amino acid, peptide or protein reacts with a hydrazide group to form a hydrazine. Also as illustrated in FIG. 12, an aldehyde reacts with an amine to form a Mannich condensation product.

Azide groups react with alkenyl or akynyl groups (in so-called Click reactions) to form triazolines or triazoles.

Phosphinothioesters react with azide groups as described in U.S. Pat. Nos. 6,972,320, 7,256,259, and 7,317,129 and U.S. published application US 2010/0048866 to form amide bonds in a traceless Staudinger ligation. Phosphinothioesters can be prepared employing phosphinothiol reagents as also described in these references. Each of these references is incorporated by reference herein in its entirety for descriptions of such ligation reactions, methods of making azides, and methods of making phosphinothioesters.

Aldehyde, ketone, azide, activated esters groups, thioester, or phosphinothiol groups are introduced or generated in amino acids, peptides and proteins to be boronated by any art-known methods and in a specific embodiment by reaction of a protein modifying reagent with one or more of an amino group, a carboxylic acid group, a sulfhydryl group or a hydroxyl group of an amino acid, peptide or protein.

Boronation methods of this invention can employ any art-known peptide ligation method for attaching one or more boronated amino acids or one or more boronated oligopeptides to a peptide or protein for enhancement of cellular uptake of the peptide or protein. Useful peptide ligation methods include, among others, native chemical ligation, expressed protein ligation, methods described in refs [47a-g], Staudinger ligation methods, including those described in U.S. Pat. No. 6,972,320, U.S. Pat. No. 7,256,259 and U.S. Pat. No. 7,317,129, and other references cited in U.S. Pat. No. 6,972,320. Each of these references is incorporated by reference herein in its entirety for descriptions of peptide ligation methods.

Boronation methods of this invention can employ various bioconjugation methods as known in the art. One or ordinary skill in the art in view of the descriptions herein and bioconjugation methods and peptide ligation methods known in the art can conjugate one or more phenylboronate compounds of this invention or one or more boronated oligopeptides of this invention to an amino acid, peptide or protein.

Boronation methods of this invention can employ crossing linking reagents for conjugating phenylboronate compounds to amino acids, peptides or proteins or for conjugating boronated oligopeptides to peptides or proteins. Crosslinking agents effect conjugation of two selected molecules and may also provide a spacer moiety between the conjugated molecules. Coupling agents, such as carbodiimides, are zero-length crosslinking reagents in which a single bond is formed between the molecules with no additional atoms added between the molecules as a spacer or linker. For example, a carbodiimide can be used to conjugate a molecule carrying an group (i.e., an amine) to a molecule carrying a carboxylate group (a carboxylic acid) by formation of an amide bond with formal loss of H$_2$O.

Various carbodiimides are known in the art and a number are commercially available for conjugation including among others EDC (1-ethyl-3-[3-dimethylaminopropyl]carbodiimide hydrochloride), DCC (dicyclohexylcarbodiimide), DIC (diisopropylcarbodiimide), CMC (N-Cyclohexyl-N'-(2-morpholinoethyl)carbodiimide methyl-p-toluenesulfonate), Woodward's reagent K (2-ethyl-5-phenylisoxazolium-3'-sulfonate), and CDI (N,N'-carbonyl diimidazole), each of which is useful for conjugating an amine with a carboxylate. CDI can also be used for conjugating a hydroxyl group to an amine forming a carbamate.

Homobifunctional crosslinking reagents contain two identical reactive groups separated by a spacer or linker moiety. Heterobifunctional crosslinking reagents contain two reactive groups with different selectively for reaction, e.g., an amine-reactive group and a sulfhydryl-reactive group separated by a spacer or linker moiety. Various homobifunctional and heterobifunctional crossing linkage reagents are known in the art and a number are commercially available from Pierce (Thermo Scientific), Rockford, Ill., Sigma-Aldrich, St. Louis, Mo. or Molecular Probes (Life Technologies), Eugene Oreg.

Useful homobifunctional crosslinking reagents include those carrying two amine-reactive groups, those carrying two sulfhydryl reactive groups, those carrying two carboxylate reactive groups, or those carrying two aldehyde or ketone reactive groups.

Useful heterobifunctional crosslinking reagents include those carrying one of an amine-reactive group, a sulfhydryl reactive group, a carboxylate reactive group, or an aldehyde or ketone reactive group and one of a different reactive group selected from an amine-reactive group, a sulfhydryl reactive group, a carboxylate reactive group, or an aldehyde or ketone reactive group.

Homobifunctional and heterobifunctional crosslinking reagents can in general contain any spacer or linking moiety compatible with the reactive groups therein wherein the spacer or linker itself is not reactive with the compounds to be conjugated. In specific embodiments, the spacer or linking moiety typically ranges from 3-20 atoms (typically C, O, S and/or N atoms) in length (including residues from the reactive group), and optionally contain one or more carbon-carbon double bonds, and/or a 5- or 6-member alicyclic, heterocyclic, aryl or heteroaryl ring. Carbon atoms in the spacer or linker are often substituted with one or more hydroxyl groups, oxo moieties (=O), or halogens (e.g., F). Nitrogen groups in the linker may be substituted with hydrogen or with C1-C3 alkyl groups. The spacer or linker may contain one or two —S—S— and/or —SO$_2$— moieties which are cleavable. The spacer or linker may be selectively cleavable, for example, by change of conditions (e.g., pH change), addition of a cleavage reagent, or photoirradiation (e.g., UV irradiation). In specific embodiments, a cleavable linker includes one or two disulfide bonds which are selectively cleavable, for example on treatment with dithiothreitol, a cleavable linker contains a diol moiety which is selectively cleavable by treatment for example with periodate, an ester moiety, which id selectively cleavable by treatment with hydroxylamine, a sulfone moiety (—SO$_2$—) which is selectively cleavable under alkaline conditions.

Homobifunctional crosslinking reagents can be used, for example, to conjugate an amino group of a nucleic acid, an amino acid, peptide or protein with an amine substituent on a phenylboronate compound. Amine-reactive groups employed in homobifunctional crosslinking reagents include among others, activated ester groups, such as NHS esters (N-hydroxysuccinimide esters) or sulfo NHS esters (N-hydroxysulfosuccinimide esters), imidoester group, such as methylimidate salts, isothiocyanate groups and aryl halide groups, such as difluorobenzene derivatives. Amine-reactive homobifunctional include among others:
dithiobis(succinimidylproprionate) [DSP] and its sulfo-NHS analog [DTSSP], disuccinimidyl suberate [DSS] and its sulfo-NHS analog [BS3], disuccinimidyl tartarate [DST] and its sulfo NHS analog [sulfo-DST], bis(2-succinimidyloxy-carbonyloxy)ethylsulfone [BSOCOES] and its sulfo-NHS analog [sulfo-BSOCOES], ethylene glycol bis(succinimidylsuccinate) [EGS] and its sulfo-NHS analog [sulfo-EGS], disuccinimidyl glutarate [DSG], N,N'disuccinimidyl carbonate [DSC], dimethyl adipimidate [DMA], dimethyl 3,3-dithiobispropionimidate [DTBP], 4,4'-disiothiocyanatostilbene-2,2'-disulfonic acid salts, 1,5-difluoro-2,4-dinitrobenzene [DFDNB], 4,4'-difluoro-3,3'-dinitrodiphenylsulfone.

Homobifunctional crosslinking reagents can be used, for example, to conjugate a sulfhydryl group of an amino acid, peptide or protein with a sulfhydryl substituent on a phenylboronate compound. Sulfhydryl-reactive groups employed in homobifunctional crosslinking reagents include among others, alkyl halide groups, maleimide groups, and dithiopyridyl groups. Sulfhydryl-reactive homobifunctional crosslinking reagents include, among others, 1,4-di-[3'-(2'-pyridyldithio)propionamido]-butane [DPDPB], bismaleimidohexane[BMH], 1,4-bismaleimidyl-2,3-dihyroxybutane [BMDB], 1,8-bismaleimidodiethyleneglycol [BM9PEG)2], bismaleimidoethane [BMOE], dithiobismaleimidoethane [DTME], and N,N'-hexamethylene-bis(iodoacetamide).

Hydroxyl-reactive homobifunctional crosslinking reagents can be used to conjugate a hydroxyl group on an amino acid, peptide or proteins with a hydroxyl group substituent on a phenylboronate compound. Hydroxyl-reactive groups include those having epoxide groups, such as diglycidylethers, particularly 1,4-butanediol diglycidyl ether.

Bis-epoxide reagents can also react with amino groups and sulfhydryl groups. A carboxylate group in an amino acid, peptide or protein can be conjugated to a carboxylate group substituent in a phenylboronate compound, for example, by generating an active ester at the carboxylate groups and esterifying the active esters with an alkanediol crosslinking reagent, such a 1,6-hexane diol, or 1,12-dodecanediol.

Aldehyde/ketone-reactive homobifunctional crosslinking reagents can be used to conjugate an aldehyde or ketone group introduced or generated in an amino acid, peptide or protein with an aldehyde or ketone group substituent on a phenylboronate compound. Bis-hydrazide reagents can be used to crosslink molecules containing aldehyde or ketone groups, examples of such crosslinking reagents include among others adipic acid dihydrazide and carbohydrazide.

Heterobifunctional crosslinking reagents include those which contain an amine reactive group and a sulfhydryl-reactive group. For example, such a heterobifunctional crosslinking reagent can be used to link an amino group in a nucleic acid, an amino acid, peptide or protein with a sulfhydryl substituent in a phenylboronate or alternatively to link a sulfhydryl group in an amino acid, peptide or protein with an amine substituent in a phenylboronate compound.

Exemplary heterobifunctional crosslinking reagents include those carrying an activated ester group, such as an NHS ester (or sulfo-NHS ester) group or a nitrophenyl or other substituted phenyl ester and a maleimide group; those carrying such an activated ester group and a dithiopyridyl group, those carrying an activated ester group and an haloacetyl group (e.g., an iodoacetyl group), or those carrying an imidoester group and a maleimide group.

Exemplary heterobifunctional amine/sulfhydryl-reactive crosslinking reagents include, among others, N-(γ-maleimidobutyryloxy)succinimide ester [GMBS] and its sulfo-NHS analog [sulfo-GMBS], 4-succinimidyloxycarbonyl-α-(2-pyridyldithio)toluene [SMPT], succinimidyl-4-(N-maleimidomethyl)cyclohexane-1-carboxylate [SMCC] and its sulfo-NHS analog [sulfo-SMCC], m-maleimidobenzoyl-N-hydroxy-succinimide ester [MBS] and its sulfo-HNS analog [sulfo-MBS], N-succinimidyl(4-iodoacetyl)-aminobenzoate [SIAB] and its sulfo-HNS analog [sulfo-SIAB], succinimidyl-6-(iodoacetyl)aminohexanoate [SIAX], N-succinimidyl-3-(2-pyridylthio)propionate [SPDP], succinimidyl-4-(p-maleimidophenyl)butyrate [SMPB] and its sulfo-NHS analog [sulfo-SMPB], succinimidyl-([N-maleimidopropionamidol]ethyleneglycol esters [SM(PEG)n, where n is 4, 6, 8, 12, 24] and p-nitrophenyl iodoacetate [NPIA], N-hydroxysuccinimidyl 2,3-dibromopropionate [SDBP].

Heterobifunctional crosslinking reagents useful in this invention for conjugation of an amino acid, peptide or protein with a phenylboronate compound include those which contain a sulfhydryl-reactive group, such as a maleimide or a pyridyldithio group, and a hydrazide which reacts with a carbonyl (aldehyde or ketone). Such reagents are particularly useful for linking a phenylboronate having an aldehyde of ketone substituent with an amino acid, peptide or protein having a sulfhydryl group. In specific embodiments, 4-(4-N-maleimidophenyl)butyric acid hydrazide HCl [MPBH], 4-(N-maleimidomethyl)cyclohexane-1-carboxyl-hydrazide [M$_2$C$_2$H], and 3-(2-pyridyldithio)propionyl hydrazide [PDPH] are such a heterobifunctional crosslinking reagents.

Heterobifunctional crosslinking reagents useful in this invention for conjugation of an amino acid, peptide or protein with a phenylboronate compound include those which contain a sulfhydryl-reactive group, such as a maleimide, and an isocyanate group for reaction with a hydroxyl group. In a specific embodiment, N-(p-maleimidophenyl)-isocyanate is such a heterobifunctional crosslinking reagent.

Heterobifunctional crosslinking reagents also include those which contain one of an amine-reactive, sulfhydryl-reactive, carboxylate-reactive or carbonyl-reactive group and a photoreactive group which is activated on irradiation to reactive with various reactive groups, including nucleophiles, reactive hydrogen, active hydrogen amines or olefins. Such reagents are particularly useful for linking an amino acid, peptide or protein having an amino group, sulfhydryl group, carboxylate group, or carbonyl group with a phenylboronate compound which reacts with the activated photoreactive group.

Photoreactive groups include, among others, optionally substituted aryl azides which are photolyzed to aryl nitrenes or to dihydroazepine groups, diazo or diazopyruvate groups which are photolyzed to reactive carbines, diazirines which are photolyzed to reactive carbenes, and benzophenone groups which are photolyzed to give a highly reactive triplet-state ketone intermediate.

Aryl azides include, among others, phenyl azide groups, fluorinated phenyl azide groups (e.g., tetrafluorophenyl azide groups), hydroxyphenyl azide groups (e.g., ortho or meta hydoxyphenylazide groups), nitrophenylazide groups, or a 7-azido-4-methylcoumarin group. Aryl nitrenes can undergo addition reactions with double bonds, and insertion reactions into active hydrogen bonds (C—H or N—H bonds).

Dehydroazepine intermediates react with nucleophiles by nucleophilic addition, particularly with amines. The aryl group of the aryl azide or the 7-member dehydroazepine ring becomes part of the linker formed on crosslinking.

The triplet state intermediate formed on photolysis of benzophenone reacts with reactive hydrogen containing groups H—R' to form R—C(OH)(Ph)$_2$.

Carbenes formed on photolysis of diazo compounds can insert into active C—H or N—H bonds or add to double bonds. Carbenes formed on photolysis of diazopyruvate groups rearrange to reactive ketenes which reactive with nucleophiles, including amines.

Specific examples of such photoreactive heterobifunctional crosslinking reagents include, among others, N-hydroysuccinimidyl-4-azidosalicyclic acid [NHS-ASA] or its sulfo-NHS analog [sulfo-NHS-ASA], sulfosuccinimidyl-(4-azidosalicylamino)hexanoate [sulfo-NHS-LC-ASA], sulfo-succinimidyl-2-(7-azido-4-methylcoumarin-3-acetamide) ethyl-1,3'-dithiopropionate [SAED], p-nitrophenyl diazopyruvate [pNPDP], p-nitrophenyl-2-diazo-3,3,3-trifluoropropionate [PNP-DTP], 1(p-azidosalicylamido)-4-(iodoacetamido)butane [ASIB], benzophenone-4-iodoacetamide, benzophenone-4-malemide, p-azidobenzoyl hydrazide [ABH], and 4-(p-azidosalicylamido)butylamine [ASBA], N-(2-((2-((4-azido-2,3,5,6-tetrafluoro)benzoyl)amino)ethyl)dithio)ethyl)-maleimide [TFPAM-SS1], With respect to any specific homo- or heterobifunctional crosslinking reagents noted above, it will be appreciated that analog crosslinking reagents having different lengths of linker moiety are also included herein. Homobifunctional crosslinking reagents preferred for use in the present invention are amine-reactive or sulfhydryl-reactive crosslinking reagents. Heterobifunctional crosslinking reagents preferred for use in the present invention are those that contain an amine-reactive group and a sulfhydryl-reactive group.

It will be appreciated by one of ordinary skill in the art that the specific coupling or crosslinking methods described herein can be readily adapted for use with any cargo molecule.

The invention provides a method for improved delivery of a cargo molecule, nucleic acid, peptide or protein to a cell which comprises the step of contacting the cell or tissue containing the cell with a peptide or protein boronated with a phenylboronic acid. Any methods known in the art for contacting a cell or tissue containing the cell can be employed which will bring the boronated cargo molecule into the vicinity of the cell or tissue. Contacting may occur in vitro by addition of a solution containing the boronated cargo molecule to a solution or medium containing or supporting the cell or tissue. Contacting may occur in vivo by any method known in the art for administration of a solution or other composition containing the boronated peptide or protein to an organism containing the cell or tissue.

Any suitable form of administration can be employed in the methods herein. The compounds of this invention can, for example, be administered orally, topically, intravenously, intraperitoneally, subcutaneously, or intramuscularly, in any suitable dosage forms well known to those of ordinary skill in the pharmaceutical arts. The boronated cargo molecules are optionally administered with a pharmaceutical carrier selected upon the basis of the chosen route of administration and standard pharmaceutical practice, such as, for example, as described in Remingtons Pharmaceutical Sciences, 17th edition, ed. Alfonoso R. Gennaro, Mack Publishing Company, Easton, Pa. (1985), which is incorporated herein by reference in its entirety for suitable administration and carriers.

Cargo molecules include nucleic acids, peptides, proteins, small molecule drugs, reporters and labeling (fluorescent labels or isotopic labels for example), imaging agents, contrast agents, particles carrying reactive functional groups, quantum dots carrying reactive functional groups, among others. In general any cargo molecule that is desired to introduce into a cell can be employed in the methods of this invention. Cargo molecules include those having a biological activity. In specific embodiments, biological activity of interest of the cargo molecule is retained on boronation or is recovered on selective removal of boronation after delivery to a cell. In a specific embodiment, the boronated cargo molecule retains at least 10% of a selected biological activity of the cargo molecule prior to boronation. In other specific embodiments, the boronated cargo molecule retains at least 50% of a selected biological activity of the cargo molecule prior to boronation. In a further specific embodiment, the boronated cargo molecule retains at least 80% of the activity of the cargo molecule prior to boronation.

In a specific embodiment, the cargo protein is an enzyme. In a specific embodiment, the cargo protein is not glycosylated (i.e., is not a glycoprotein). In a specific embodiment, the boronated cargo peptide or protein retains at least 10% of a selected biological activity of the protein prior to boronation. In other specific embodiments, the boronated cargo peptide or protein retains at least 50% of a selected biological activity of the protein prior to boronation. In a further specific embodiment, the boronated cargo peptide or protein retains at least 80% of the activity of the peptide or protein prior to boronation. Peptides and proteins include those having enzyme activity.

Cargo peptides include peptide ligands, cytotoxic peptides, bioactive peptides, diagnostic agents, among others. Cargo peptides include those having 2-1000 amino acids, 2-500 amino acids, 2-250 amino acids, 2-100 amino acids, 2-50 amino acids, and 2-25 amino acids and 2-10 amino acids.

Peptides and proteins include antibodies and functional fragments thereof, where the term antibody is used broadly herein. More specifically, antibodies include among others, monoclonal antibodies including humanized antibodies, human antibodies, interspecies antibodies, chimeric antibodies, human monoclonals, humanized monoclonals, interspecies antibodies made by any art-known methods. Functional fragments of antibodies include F(ab')2, F(ab)2, Fab', Fab, Fv, among others, as well as hybrid fragments. Additionally, antibodies include subfragments retaining the hypervariable, antigen-binding region of an immunoglobulin and preferably having a size similar to or smaller than a Fab' fragment. Such fragments and subfragments including single chain fragments or multiple chain fragments, which incorporate an antigen-binding site and exhibit antibody function, are known in the art and can be prepared by methods that are well-known in the art, including by methods of preparing recombinant proteins. Antibodies and fragments thereof include therapeutic antibodies which are known in the art [42]. This reference is incorporated by reference herein in its entirety for descriptions of therapeutic antibodies which can be employed in the present invention.

In a specific embodiment, the cargo molecule is a nucleic acid which may be RNA or DNA, or an analog of a nucleic acid which may be a peptide nucleic acid, a locked nucleic acid, or a phosphoradiamidate morpholino oligomer. Other art-known nucleic acid analogs include carbamate-linked DNA, phosphorothioate-linked DNA, 2'-O-methyl RNA, phosphotriester-linked DNA or methylphosphonate-linked DNA. The cargo nucleic acid can be single- or double-stranded. The nucleic acid can be an oligonucleotide or analog thereof having 2-100, 2-50 or 2-25 bases. The nucleic acid can be SiRNa, microRNa, antisense oligonucleotides, decoy DNA, plasmids or other nucleic acid structures such as minicircles. Nucleic acids and analogs thereof are available from commercial sources, can be isolated from natural source or can be prepared by methods that are well-known in the art.

In a specific embodiment, the boronated cargo nucleic acid retains at least 10% of a selected biological activity of the nucleic acid prior to boronation. In other specific embodiments, the boronated cargo nucleic acid retains at least 50% of a selected biological activity of the nucleic acid prior to boronation. In a further specific embodiment, the boronated cargo nucleic acid retains at least 80% of the activity of the nucleic acid prior to boronation. In a specific embodiment, the biological activity of the nucleic acid that is retained in binding to a complementary nucleic acid or binding to another biological molecule (e.g., a peptide or protein).

Cargo nucleic acids include those having 2-1000 bases, 2-500 bases, 2-250 bases, 2-100 bases, 2-50 bases, and 2-25 bases and 2-10 bases. Nucleic acids include nucleosides and analogs thereof.

In specific embodiments, cargo molecules of this invention include antibodies and various forms and fragments thereof. In specific embodiments, cargo molecules include transcription factors (proteins) which affect transcription of DNA to messenger RNA and thus affect expression of one or more genes. In specific embodiments, transcription factors include one or more DNA-binding domains. Transcription factors include among others tumor suppressors. A specific transcription factor of potential clinical interest is FOXO3 which functions as a trigger for apoptosis (see: A "FOXO" in sight: Targeting Foxo proteins from conception to cancer. [43]. One or more boronation reagents of this invention can be employed to boronate transcription factors, including FOXO transcription factors, and more specifically FOXO3 to facilitate cell uptake thereof. Employing the reversible boronation reagents herein, boronates are removed after cell uptake to facilitate entry into the cytosol of the cell.

In specific embodiments, cargo molecules include proteins that function as tumor suppressors. For example, cargo molecules include PTEN which is a phosphatidylinositol-3, 4,5-trisphosphate 3-phosphatase (see: P Hopkins, et al. Science 2013, 341, 399-402.) PTEN contains a tensin-like domain as well as a phosphatase catalytic domain. PTEN negatively regulates the Akt/PKB signaling pathway functioning as a tumor suppressor. One or more boronation reagents of this invention can be employed to boronate PTEN to facilitate cell uptake thereof. Employing the reversible boronation reagents herein, boronates are removed after cell uptake to facilitate entry into the cytosol of the cell.

In a specific embodiment, the cargo molecule is SCRIB, a scaffold protein which is involved in cell migration, cell polarity and cell proliferation. [48] One or more boronation reagents of this invention can be employed to boronate SCRIB to facilitate cell uptake thereof. Employing the reversible boronation reagents herein, boronates are removed after cell uptake to facilitate entry into the cytosol of the cell.

In specific embodiments exemplified herein boronation reagents of this invention have been employed to derivatize GFP (Green fluorescent protein) with 2 phenylboronate groups to facilitate cellular uptake of the fluorescent protein. The reagents herein can be employed with various fluorescent proteins that are known in the art to facilitate their uptake into cells.

The present invention provides a method of reversibly labeling cargo molecules having one or more or two or more amino groups for cellular uptake with phenylboronate groups wherein the phenyl boronate groups are removed after cellular uptake to facilitate delivery of the cargo molecules to the cytosol of the cell. In specific embodiments, the method employs reagents of formulas VIIIA, XIA or XA (and those of related formulas herein) to react with amino groups on the cargo molecule. Preferably 2 or more amino groups of the cargo molecule are reacted to covalently attach phenylboronate groups, for example via amide linkages. After boronation, the cargo molecule is placed in contact with a cell or tissue and the boronated cargo molecule is taken up into the cell. After uptake into the cell, the phenylboronate groups are removed within the cell, for example, by the action of cellular enzymes (e.g., esterases), oxidation or by a change in pH in the cell. Removal of phenylboronate groups facilitates delivery into the cytosol.

An aliphatic group as used herein refers to a monovalent non-aromatic hydrocarbon group which include straight chain, branched, or cyclic hydrocarbon groups which can be saturated or unsaturated with one or more double bonds or one or more triple bonds. Aliphatic groups may contain portions which are straight-chain or branched in combination with one or more carbon rings. Carbon rings of aliphatic groups may contain one or more double bonds or one or more triple bonds. Carbon rings of aliphatic groups can contain 3- to 10-membered rings. Such carbon rings may be fused and may be bicyclic or tricyclic. Aliphatic groups are optionally substituted with one or more non-hydrogen substituents where optional substituents are described herein. Unless otherwise specified, an aliphatic group can contain 1-20 carbon atoms or can contain 1-10 carbon atoms. Aliphatic groups include those containing 1-3, 1-6, and 1-8 carbon atoms. Aliphatic groups include, among others, alicyclic groups, alkyl groups, alkenyl groups and alkynyl groups.

Heteroaliphatic groups refer generally to aliphatic groups having 1 or more heteroatoms (other than C and H). Specifically heteroatoms of heteroaliphatic groups are selected from N, P, B, O or S. In more specific embodiments, heteroaliphatic groups contain one or more oxygens, nitrogen or sulfur atoms.

An alicylic group as used herein refers to a monovalent non-aromatic cyclic hydrocarbon group which can be saturated or unsaturated with one or more double bonds or one or more triple bonds. Alicyclic rings include those containing 3- to 10-membered carbon rings. Alicyclic groups include those containing one, two, three or more rings which may be fused or linked by straight chain or branched alkylene, alkenylene or alkynylene moieties. Alicyclic groups include bicyclic and tricyclic rings. Alicyclic groups include those in which one or more carbon rings are substituted with a straight-chain or branched alkyl, alkenyl or alkynyl group. To satisfy valence requirements, a ring atom may be substituted with hydrogen or optionally with non-hydrogen substituents as described herein. One or more carbons in an alicyclic group can be —CO— groups, i.e. a carbon can be substituted with an oxo (=O) moiety. Alicyclic groups are optionally substituted with one or more non-hydrogen substituents where optional substituents are described herein. Unless otherwise specified, an alicyclic group can contain 3-20 carbon atoms or can contain 3-12 carbon atoms. Alicyclic groups include those containing 3-6 and 3-8 carbon atoms. Alicyclic groups include among others cycloalkyl, cycloalkenyl, cyclopropyl, cyclobutyl, cyclopentyl, cyclopentadienyl, cyclohexyl, cyclohexenyl and cyclohexadienyl groups, all of which are optionally substituted.

A heterocyclic group as used herein refers to a monovalent non-aromatic cyclic hydrocarbon group wherein one or more of the rings contain one or more heteroatoms (e.g., N, S, O, or P) which rings can be saturated or unsaturated with one or more double bonds or one or more triple bonds. In specific embodiments of this invention, heterocyclic rings which are substituents of the compounds of formulas IA and IB do not contain boron atoms. Heterocyclic rings include those containing 3- to 10-membered rings where 1, 2 or 3 of the ring members are heteroatoms. Heterocyclic groups include those containing one, two, three or more rings which may be fused or linked by straight chain or branched alkylene, alkenylene or alkynylene moieties. Heterocyclic groups include bicyclic and tricyclic groups. Heterocyclic groups include those in which a heterocyclic ring is substituted with a straight-chain or branched alkyl, alkenyl or alkynyl group. To satisfy valence requirements, a ring atom may be substituted with hydrogen or optionally with non-hydrogen substituents as described herein. One or more carbons in a heterocyclic group can be —CO— groups. One or more carbons in a heterocyclic ring can be —CO-groups. Heterocyclic groups are optionally substituted with one or more non-hydrogen substituents where optional substituents are described herein. Ring carbons and, where chemically feasible, ring heteroatoms are optionally substituted. Unless otherwise specified, a heterocyclic group can contain 3-20 carbon atoms, can contain 3-12 carbon atoms or can contain 3-6 carbon atoms. Heterocyclic groups include those containing one or two 4-, 5- or 6-member rings at least one of which has one, two or three N, O or S atoms and wherein a ring optionally has one or two double bonds. Heterocyclic groups include those containing a single 5- or 6-member ring having one, two or three N, O or S atoms and optionally having one or two double bonds. Heterocyclic groups include those having 5- and 6-member rings with one or two nitrogens and one or two double bonds. Heterocyclic groups include those having 5- and 6-member rings with an oxygen or a sulfur and one or two double bonds. Heterocyclic groups include those having 5- or 6-member rings and two different heteroatom, e.g., N and O, O and S or N and S. Heterocyclic groups include those having 5- or 6-member rings and a single heteroatom, e.g., N S or O. In specific embodiments, heterocyclic groups do not include any boron atoms. Specific heterocyclic groups include among others among others, pyrrolidinyl, piperidyl, piperazinyl, pyrrolyl, pyrrolinyl, furyl, thienyl, morpholinyl, oxazolyl, oxazolinyl, oxazolidinyl, indolyl, triazoly, and triazinyl groups, all of which are optionally substituted.

In embodiments herein alicyclic or heterocyclic rings can be formed between certain substitution sites on the molecules of formulas IA or IB. Such rings include the atom(s) of or between the sites of substitution and are defined with respect to the optional presence of heteroatoms, the optional presence of —CO— moieties and the optional presence of double bonds as are alicylic and heterocyclic groups. Unless otherwise specified such rings can contain 5-10-member rings and more preferably contain 5- to 8-member rings and more preferably 5- or 6-member rings. Ring atoms are optionally substituted as described herein.

Aryl groups are monovalent groups containing at least one aromatic ring. Aryl groups include groups having one or more 5- or 6-member aromatic rings. Aryl groups can contain one, two or three, 6-member aromatic rings. Aryl groups can contain two or more fused aromatic rings. Aryl groups can contain two or three fused aromatic rings. Aryl groups may contain one or more non-aromatic alicyclic rings in addition to an aromatic ring. Aryl groups are optionally substituted with one or more non-hydrogen substituents as described herein. Substituted aryl groups include among others those which are substituted with alkyl or alkenyl groups, which groups in turn can be optionally substituted. Specific aryl groups include phenyl groups, biphenyl groups, and naphthyl groups, all of which are optionally substituted as described herein. In a specific embodiment, aryl groups are not substituted with a boron-containing substituent, e.g., —B(OH)$_2$ or a —CH$_2$—B—O— moiety. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Unless otherwise specified, an aryl group can contain 5-20 carbon atoms or can contain 6-14 carbon atoms. Aryl groups also include those containing 6-12 carbon atoms.

Heteroaryl groups are monovalent groups having one or more aromatic rings in which at least one ring contains a heteroatom (a non-carbon ring atom). Heteroaryl groups include those having one or two heteroaromatic rings carrying 1, 2 or 3 heteroatoms and optionally having one 6-member aromatic ring. Heteroaryl groups can contain 5-20, 5-12 or 5-10 ring atoms. Heteroaryl groups include those having at least one aromatic ring containing a heteroatom and one or two alicyclic, heterocyclic or aryl ring groups. Heteroaryl groups include those having one aromatic ring containing a heteroatom and one aromatic ring containing carbon ring atoms. Heteroaryl groups include those having one or more 5- or 6-member aromatic heteroaromatic rings and one or more 6-member carbon aromatic rings. Heteroaromatic rings can include one or more N, O, or S atoms in the ring. Heteroaromatic rings can include those with one, two or three N, those with one or two O, and those with one or two S, or combinations of one or two or three N, O or S. Specific heteroaryl groups include pyridinyl, pyrazinyl, pyrimidinyl, quinolinyl, and purinyl groups. In specific embodiment, heteroaromatic rings that are substituents on compounds of formulas IA or IB do not contain B atoms.

In embodiments herein aryl or heteroaryl rings can be formed between certain substitution sites on the molecules of formulas IA or IB. Such rings include the atom(s) of or between the sites of substitution and are defined with respect to the optional presence of heteroatoms. Unless otherwise specified such rings can contain 5- or 6-member rings and ring atoms are optionally substituted as defined herein.

Alkyl groups are monovalent groups and include straight-chain, branched and cyclic alkyl groups. Unless otherwise indicated alkyl groups include those having from 1 to 20 carbon atoms. Alkyl groups include alkyl groups having 1 to 3 carbon atoms, alkyl groups having from 4-7 carbon atoms and alkyl groups having 8 or more carbon atoms. Cyclic alkyl groups include those having one or more rings. Cyclic alkyl groups include those which have 1, 2 or 3 rings. Cyclic alkyl groups also include those having 3-10 carbon atoms. Cyclic alkyl groups include those having a 3-, 4-, 5-, 6-, 7-, 8-, 9- or 10-member carbon ring and particularly those having a 3-, 4-, 5-, 6-, 7-, or 8-member ring. The carbon rings in cyclic alkyl groups can also carry straight-chain or branched alkyl group substituents. Cyclic alkyl groups can include bicyclic and tricyclic alkyl groups. Alkyl groups are optionally substituted with one or more non-hydrogen substituents as described herein. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, cyclohexyl, decalinyl, and norbornyl, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups. Substituted alkyl group include alkyl group substituted with one or more hydroxyl groups. Substituted alkyl groups include groups substituted with two or more hydroxyl groups, particularly where two hydroxyl groups are substituted on adjacent carbon atoms.

Arylalkyl groups are monovalent alkyl groups substituted with one or more aryl groups wherein the alkyl groups optionally carry additional substituents and the aryl groups are optionally substituted. Specific arylakyl groups are phenyl-substituted alkyl groups, e.g., benzyl groups or phenethyl groups which are optionally substituted. Heteroarylalkyl groups are monovalent alkyl groups substituted with one or more heteroaryl groups wherein the alkyl groups optionally carry additional substituents and the aryl groups are optionally substituted. Alkylaryl groups are monovalent aryl groups substituted with one or more alkyl groups wherein the alkyl groups optionally carry additional substituents and the aryl groups are further optionally substituted. Specific alkylaryl groups are alkyl-substituted phenyl groups such as o-, m- or p-tolyl groups which are optionally substituted. Alkylheteroaryl groups are monovalent alkyl groups substituted with one or more heteroaryl groups wherein the alkyl groups optionally carry additional substituents and the heteroaryl groups are optionally substituted.

Alkenyl groups include monovalent straight-chain, branched and cyclic alkenyl groups which contain one or more carbon-carbon double bonds. Unless otherwise indicated alkenyl groups include those having from 2 to 20 carbon atoms. Alkenyl groups include those having 2 to 4 carbon atoms and those having from 5-8 carbon atoms. Cyclic alkenyl groups include those having one or more rings wherein at least one ring contains a double bond. Cyclic alkenyl groups include those which have 1, 2 or 3 rings wherein at least one ring contains a double bond. Cyclic alkenyl groups also include those having 3-10 carbon atoms. Cyclic alkenyl groups include those having a 5-, 6-, 7-, 8-, 9- or 10-member carbon ring and particularly those having a 5- or 6-member ring. The carbon rings in cyclic alkenyl groups can also carry straight-chain or branched alkyl or alkenyl group substituents. Cyclic alkenyl groups can include bicyclic and tricyclic alkyl groups wherein at least one ring contains a double bond. Alkenyl groups are optionally substituted with one or more non-hydrogen substituents as described herein. Specific alkenyl groups include ethylene, propenyl, cyclopropenyl, butenyl, cyclobutenyl, pentenyl, pentadienyl, cyclopentenyl, cyclopentadienyl, hexylenyl, hexadienyl, cyclohexenyl, cyclohexadienyl, including all isomers thereof and all of which are optionally substituted. Substituted alkenyl groups include fully halogenated or semihalogenated alkenyl groups.

Alkynyl groups include mono-valent straight-chain, branched and cyclic alkynyl group which contain one or more carbon-carbon triple bonds. Unless otherwise indicated alkynyl groups include those having from 2 to 20 carbon atoms. Alkynyl groups include those having 2 to 4 carbon atoms and those having from 5-8 carbon atoms. Cyclic alkynyl groups include those having one or more rings wherein at least one ring contains a triple bond. Cyclic alkynyl groups include those which have 1, 2 or 3 rings wherein at least one ring contains a triple bond. Cyclic alkynyl groups also include those having 3-10 carbon atoms. Cyclic alkynyl groups include those having a 5-, 6-, 7-, 8-, 9- or 10-member carbon ring and particularly those having a 5- or 6-member ring. The carbon rings in cyclic alkynyl groups can also carry straight-chain or branched alkyl, alkenyl or alkynyl group substituents. Cyclic alkynyl groups can include bicyclic and tricyclic alkyl groups wherein at least one ring contains a triple bond. Alkynyl groups are optionally substituted with one or more non-hydrogen substituents as described herein.

An alkoxy group is an alkyl group (including cycloalkyl), as broadly discussed above, linked to oxygen, a monovalent —O-alkyl group. An aryloxy group is an aryl group, as discussed above, linked to an oxygen, a monovalent —O-aryl. A heteroaryloxy group is a heteroaryl group as discussed above linked to an oxygen, a monovalent —O-heteroaryl. Alkenoxy, alkynoxy, alicycloxy, heterocycloxy groups are analogously defined. All of such groups are optionally substituted.

The number of carbon atoms in a given group, such as an alkyl group, can be indicated herein using the expression "Cm" where m is the number of carbon atoms. Thus, the expression "Cm1-Cm2" modifying a given chemical group indicates that the group can contain from m1 to m2 carbon atoms. For example, a C1-C6 alkyl group contains 1 to 6 carbon atoms, exclusive of carbons in any substituent on the alkyl group. Similar expressions can be used to indicate the number of atoms of N (nitrogen), O (oxygen) or other elements in a given group.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

Phenylboronate compounds and boronated oligopeptides of the invention may be in the form of salts. Preferred salts are those that are biologically acceptable for ultimate applications of boronated peptides and proteins and which do not substantially detrimentally affect the effectiveness and properties of the free bases or free acids, and which are not biologically or otherwise undesirable. Salts may be prepared from addition of an organic or inorganic base to the free acid or addition of an organic or inorganic acid to the free base.

Exemplary salts of free bases are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, lactic acid, benzoic acid, cinnamic acid, mandelic acid, methanesulfonic acid, ethanesulfonic acid, p-toluenesulfonic acid, salicylic acid, trifluoroacetic acid, N-acetylcysteine and the like.

Exemplary salts of free acids are formed with inorganic base include, but are not limited to, alkali metal salts (e.g., Li+, Na+, K+), alkaline earth metal salts (e.g., Ca2+, Mg2+), non-toxic heavy metal salts and ammonium ($NH_4$+) and substituted ammonium (N(R')4+ salts, where R' is hydrogen, alkyl, or substituted alkyl, i.e., including, methyl, ethyl, or hydroxyethyl, specifically, trimethyl ammonium, triethyl ammonium, and triethanol ammonium salts), salts of cationic forms of lysine, arginine, N-ethylpiperidine, piperidine, and the like. Compounds of the invention can also be present in the form of zwitterions.

The term kit refers to kits for enhancement of cellular delivery and to kits for boronating cargo molecules, particularly cargo molecules which are nucleic acids, peptides or proteins. In one embodiment, kits of this invention include one or more of the phenylboronate compounds of the present invention or mixtures thereof and optionally reagents for ligating, conjugating or reacting the phenylboronate compound with a cargo molecule, e.g., a nucleic acid, peptide or protein to effect boronation of the cargo molecule. In another embodiment, kits of this invention include one or more boronated oligopeptides of this invention and optionally reagents, such as one or more homo- or heterobifunctional crosslinking reagents, for ligating or conjugating the boronated oligopeptide to a cargo molecule to effect boronation of the cargo molecule. In yet another embodiment, kits of this invention may contain one or more protected boronated amino acids and optionally one or more non-boronated amino acids suitable for carrying out solid phase peptide synthesis of a boronated peptide including a boronated oligopeptide. In this embodiment, kits may also contain resin for carrying out solid phase peptide synthesis as well as reagents, solvents and other components needed for or useful for carrying out solid phase peptide synthesis.

Additionally such kits for synthesis of boronated oligopeptides optionally contain one or more reagents, such one or more coupling reagents, or one or more homo- or heterobifunctional crosslinking reagents, for conjugation of the phenylboronate or boronated oligopeptide to a peptide or protein to effect boronation of the peptide or protein. Kits of the invention may also contain reagents for labeling of cargo molecules including reagents for labeling nucleic acids, peptides and proteins in addition to boronation of cargo molecules. Kits for enhancing cellular uptake of a cargo molecule may further contain one or more cargo molecules which are to be boronated for delivery to cells. Cargo molecules may further contain structural portions including cell penetrating peptides or targeting peptides, such as nuclear localization signals (such as are known in the art). Such kits may additionally comprise cells and cell growth media.

Kits of the invention may comprise a carrier being compartmentalized to receive in close confinement one or more containers, such as vials, test tubes, ampules, bottles and the like. Each of such container means comprises components or a mixture of components needed to perform the indicated boronation, solid phase synthesis of boronated oligopeptide, or enhancement of cellular uptake. The kits of the invention may further comprise one or more additional components (e.g., reagents and/or compounds) necessary or desirable for carrying out one or more particular applications of the compositions of the present invention. In general kits may also contain one or more buffers, control samples, carriers or recipients, vessels for carrying out one or more reactions, vessels for containing cells and the like, one or more additional compositions of the invention, one or more sets of instructions, and the like.

Bovine pancreatic ribonuclease (RNase A) is a small, well-characterized enzyme that has been the object of much seminal work in protein chemistry. [9] If this ribonuclease can gain access to the RNA that resides in the cytosol, then its prodigious catalytic activity can lead to cell death. [10] Hence, RNase A can serve as an ideal model for assessing the delivery of a protein into the cytosol (rather than an endosome) because success can be discerned with assays of cytotoxic activity.

Initially, the affinity of simple phenylboronic acids to certain saccharides (e.g., D-fructose, D-glucose and Neu5Ac) was assessed. Sialic acid is of particular interest because of its abundance in the glycocalyx of cancerous cells. [11] Phenylboronic acid (PBA) binds with higher affinity to sialic acid than to other pyranose saccharides [12] suggesting that simple boronic acids could target chemotherapeutic agents selectively to tumors. Benzoboroxole (2-hydroxymethylphenylboronic acid) has the highest reported affinity for pyranose saccharides [12-13] which are abundant in the glycocalyx. $^1$H NMR spectroscopy was used to evaluate the affinity of PBA and benzoboroxole for fructose, glucose, and N-acetylneuraminic acid (Neu5Ac), which contains a sialic acid moiety, under physiological conditions. The Ka values determined (Table 1) are in gratifying agreement with values determined by other workers using alternative assays. [12a,12c,13] Both benzoboroxole and PBA have greater affinity for Neu5Ac than for glucose and benzoboroxole has greater affinity than PBA for each saccharide in the panel studied.

Initial studies of boronation of RNase employed benzoboroxole. To display benzoboroxole moieties on RNase A, 5-amino 2-hydroxymethylphenylboronic acid (1) was conjugated to protein carboxyl groups of the protein by condensation using a carbodiimide (Scheme 1). Of the 11 carboxyl groups of RNase A, 7.5±2.0 were condensed with boronate 1, as determined by mass spectrometry.

Figure 2:
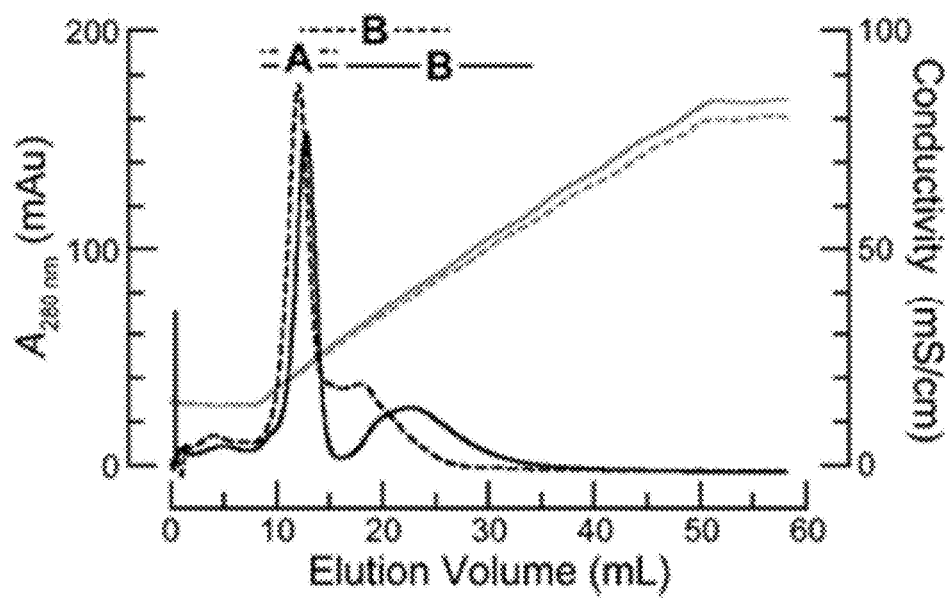
FIG. 2 is an elution profile of a mixture of unmodified RNase A (eluting in region "A") and boronated RNase A (eluting in region "B") from a column of immobilized heparin in the absence (solid line) or presence (dashed line) of fructose (0.10 M).
Figure 3:
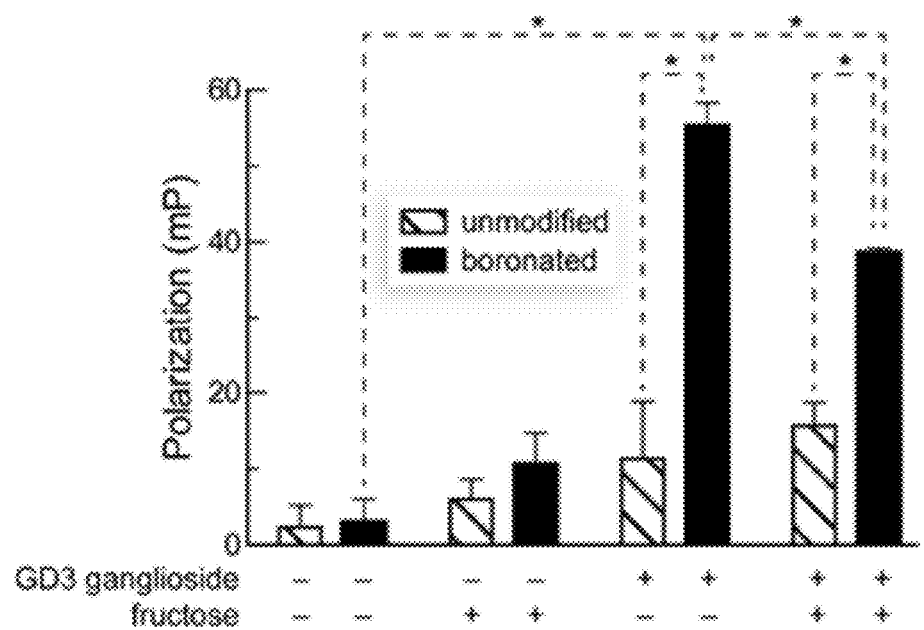
FIG. 3 shows the results of fluorescence polarization assay of ribonucleases binding ganglioside-labeled liposomes in the presence or absence of 10 mM fructose. Data was normalized to polarization of each ribonuclease incubated with non-extruded DOPC lipids. Data points represent the mean (±SD) of triplicate experiments. Asterisks indicate values with $p<0.05$.

As an initial test of the affinity of boronated protein (boronated RNAse A) for oligosaccharides. The retention of boronated and unmodified RNase A on a column of heparin, a common physiological polysaccharide, was compared. Benzoboroxole-boronated RNase A was indeed retained longer on the column (FIG. 2). The prolonged retention is believed due to boron-saccharide complexation. Addition of fructose in the elution buffer (0.10M fructose) diminished the retention of boronated RNAse A. This result is consistent with boron-saccharide complex formation indicating that fructose competes with immobilized heparin for boron complexation. To evaluate the enhanced affinity of boronated RNase A for oligosaccharides, its affinity for ganglioside GD3 within a 1,2-dioleoyl-sn-glycero-3-phosphocholine (DOPC) liposome was measured. This ganglioside has two sialic acid residues and is overexpressed on the surface of cancer cells. [15] By using fluorescence polarization to analyze binding, it was demonstrated that boronation increased the affinity of the protein for the ganglioside, an effect that was abrogated by fructose (FIG. 3). The Kd value of boronated protein for GD3 ganglioside liposomes was (54±11) μM. This affinity is ~440 fold greater than that for the binding of a single benzoboroxole to Neu5Ac (Table 1), consistent with a multivalent interaction between the boronated protein and the ganglioside.

Figure 4A:
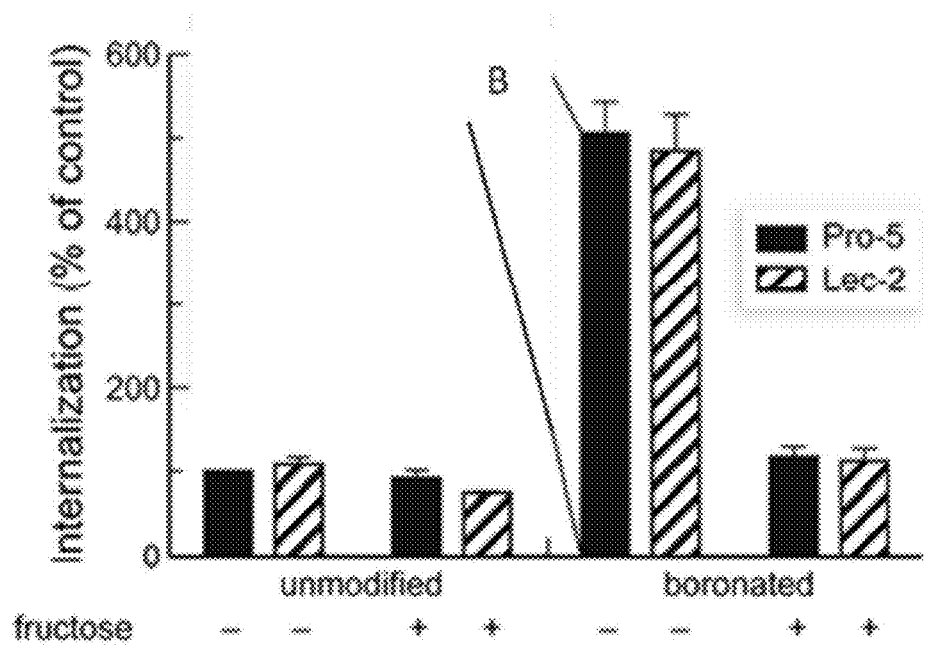
FIG. 4A is a graph of the results of flow cytometry experiments measuring internalization of unmodified and benzoboroxole-boronated RNase A into Pro-5 and Lec-2 cells in the absence or presence of fructose (0.25 M). Flow cytometry data were normalized to the internalization of unmodified RNase A into Pro-5 cells. Error bars represent the SD.

To quantify cellular internalization, fluorophore-labeled protein and flow cytometry was used. To determine concurrently if the pendant boronates elicited selectivity for cells with higher quantities of cell-surface sialic acid, two lines of Chinese hamster ovary cells were compared. Lec-2 cells have lower levels of sialic acid in their glycocalyx than their progenitor line, Pro 5. [16] Boronation of RNase A increased cellular uptake in both cell lines by 4- to 5-fold (FIG. 4A). This enhancement in cell uptake was eliminated by addition of fructose. Cell-surface sialic acid-content was not observed to affect uptake significantly. Confocal microscopy of boronated protein demonstrated punctate staining (FIG. 4B), which is consistent with uptake by endocytosis following complexation with cell-surface saccharides.

Although flow cytometry can quantify protein internalization into a cell, it does not differentiate between proteins in endosomes versus those in the cytosol. Delivery into the cytosol is important for the efficacy of numerous putative chemotherapeutic agents.

Figure 5:
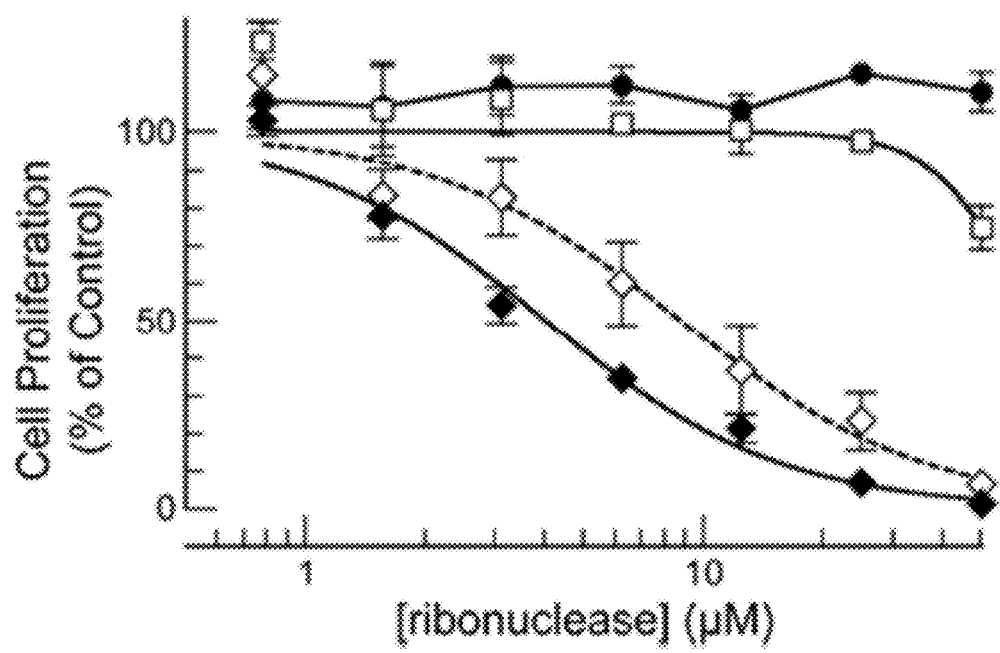
FIG. 5 is a graph showing inhibition of K-562 cell proliferation by unmodified and boronated RNase A. (•, closed circles) Unmodified RNase A (IC50>50 μM); (♦, closed diamonds) boronated RNase A (IC50 4.0±0.3 μM); (◇, open diamonds) boronated RNase A in the presence of fructose (50 mM) (IC50 9±1 μM); (□, open squares) boronated RNase A alkylated with 2-bromoacetate (IC50>50 μM). The proliferation of K-562 cells was measured by the incorporation of [methyl-3H]thymidine. Data points represent the mean (±SEM) of three separate experiments performed in triplicate.

Boronated RNase A retained (17±2)% of its ribonucleolytic activity. [17] Accordingly, boronated RNase A has the potential to be cytotoxic, if it can enter the cytosol. Boronated RNase A inhibited the proliferation of a line of human erythroleukemia cells (K-562; FIG. 5). The addition of fructose diminished cytotoxic activity, presumably by decreasing overall internalization. In contrast, chemically inactivated, boronated RNase A was much less cytotoxic, indicating that ribonucleolytic activity induced toxicity, not the pendant boronates. These results show that boronation not only facilitates cellular uptake of an enzyme, but also allows for its delivery to the cytosol and the maintenance of its catalytic activity.

Boronates have attributes that make them attractive as mediators of drug delivery. First, endosomes become more acidic as they mature. In synergy, the affinity of boronates for saccharides decreases with decreasing pH [12a]. Moreover, the ensuing loss of complexation causes boronates to become more hydrophobic. [18] These attributes are believed to facilitate translocation of proteins with pendant boronates to the cytosol. Second, boronates are not cationic [19], averting the non-specific Coulombic interactions elicited by cationic domains [2], which can lead to high rates of glomerular filtration and opsonization. [20] Finally, numerous diseases are associated with changes in cell-surface glycosylation[11, 21]. Thus, boronic acids with specificity for particular glycans can serve as the basis for targeted delivery strategies. [22]

All references throughout this application, for example patent documents including issued or granted patents or equivalents; patent application publications; and non-patent literature documents or other source material; are hereby incorporated by reference herein in their entireties, as though individually incorporated by reference.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomer, e.g., cis and trans isomers, and each enantiomer or diastereomer of the compound described individual or in any combination.

Compounds of the invention, and salts thereof, may exist in their tautomeric form, in which hydrogen atoms are transposed to other parts of the molecules and the chemical bonds between the atoms of the molecules are consequently rearranged. It should be understood that all tautomeric forms, that may exist, are included within the invention.

The processes for preparation of the compounds herein can use mixtures of isomers, racemates, enantiomers, or diastereomers as starting materials and may result in mixtures of isomers, enantiomers or diastereomers. If desired such mixtures can be separated by conventional methods, for example, by various chromatographic methods or fractional crystallization. Compounds of the invention may be in the free or hydrate form.

One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In boronation methods herein the term consisting essentially of excludes any component not required for successful boronation. In methods of enhancing cellular uptake, the term consisting essentially of excludes any component not required for successful enhancement of uptake of a given peptide or protein. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

THE EXAMPLES

Example 1: Material and Methods

Materials:

N-Acetylneuraminic acid was from Carbosynth (Berkshire, UK). Phenylboronic acid, 2-hydroxymethylphenylboronic acid, and 5-amino-2-hydroxymethylphenylboronic acid were from Combi-Blocks (San Diego, Calif.). BODIPY® FL, STP ester was from Molecular Probes (Eugene, Oreg.). [methyl-3H]Thymidine (6.7 Ci/mmol) was from Perkin-Elmer (Boston, Mass.). N-(3-Dimethylaminopropyl)-N'-ethylcarbodiimide hydrochloride (EDC) and wild-type RNase A (Type III-A) were from Sigma-Aldrich (St. Louis, Mo.) and used without further purification. Ribonuclease substrate 6-FAM-dArUdAdA-6-TAMRA was from Integrated DNA Technologies (Coralville, Iowa). Bovine Serum Albumin (BSA) was from Thermo Scientific (Rockfield, Ill.). Lysozyme, from chicken egg white (Sigma L6876) was from Sigma-Aldrich (St. Louis, Mo.) and used without further purification. Biotinylated peptide was purchased and custom synthesized from Biomatik (Cambridge, Ontario, Canada). NeutrAvidin, Fluorescein conjugated (Thermo 31006) was from Pierce Protein Research Products, Thermo Scientific (Rockford, Ill.). GD3 Ganglioside (bovine milk; ammonium salt), 1,2 dioleoyl-sn-glycero-3-phosphocholine (DOPC), and an extruder were from Avanti Polar Lipids (Alabaster, Ala.). 16S- and 23S-Ribosomal (rRNA) from *E. coli* MRE600 was from Roche Applied Science (Mannheim, Germany).

ES buffer was from Sigma-Aldrich and purified by anion-exchange chromatography to remove trace amounts of oligomeric vinylsulfonic acid. [49]

Spectra/Por® dialysis bags (3500 MWCO) were from Fisher Scientific (Thermo Fisher Scientific, Walham, Mass.). *Escherichia coli* BL21(DE3) cells were from Novagen (Madison, Wis.). Heparin HP column protein purification and analytical columns were from GE Biosciences (Piscataway, N.J.). Non-binding surface (NBS) 96-well plates were from Corning (Corning, N.Y.). Terrific Broth (TB) was from Research Products International Corp (Mt. Prospect, Ill.). SDS-PAGE gels were from Bio-Rad Laboratories (Hercules, Calif.).

Cell culture medium and supplements were from Invitrogen (Carlsbad, Calif.). Phosphate-buffered saline was either Dulbecco's PBS (DPBS) from Invitrogen or the same solution made in the laboratory (PBS), containing (in 1.0 L): 0.2 g KCl, 0.2 g $KH_2PO_4$, 8 g NaCl, and 2.16 g $Na_2HPO_4.7H_2O$ at pH 7.4. All other chemicals used were of commercial reagent grade or better, and were used without further purification.

Instrumentation and Statistics $^1$H NMR spectra were acquired at the National Magnetic Resonance Facility at Madison at 298 K on an Avance III 500 MHz spectrometer with a TCI 500 H—C/N-D cryogenic probe from Bruker AXS (Madison, Wis., $^1$H, 500 MHz). Protein absorbance values were measured on a Varian Cary 50 UV-Vis Spectrometer (Agilent Technologies, Santa Clara, Calif.) and/or a NanoVue spectrometer (GE Healthcare, Piscataway, N.J.). Confocal microscopy was carried out using an Eclipse C1 laser scanning confocal microscope from Nikon (Melville, N.Y.). Flow cytometry was done using a LSRII (BD Biosciences, San Jose, Calif.) at the University of Wisconsin-Madison Carbone Cancer Center Flow Cytometry Facility. The mass of proteins (RNase A, lysozyme, etc.), protein-conjugates, peptides and boronated peptides were confirmed at the University of Wisconsin- Madison Biophysics Instrumentation Facility by matrix-assisted laser desorption/ionization time-of-flight (MALDI-TOF) mass spectrometry with a Voyager-DE-PRO Biospectrometry Workstation from Applied Biosystems (Foster City, Calif.). [methyl-$^3$H]Thymidine incorporation into K-562 genomic DNA was quantified by scintillation counting using a Microbeta TriLux liquid scintillation and luminescence counter from Perkin-Elmer. Fluorescence measurements were made with an infinite M1000 plate reader from Tecan (Männedorf, Switzerland). Calculations for statistical significance were performed with GraphPad Prism version 5.02 software from GraphPad Software (La Jolla, Calif.), and a value of p<0.05 was considered to be significant.

Example 2: Determination of $K_a$ Values by $^1$H NMR Spectroscopy

Methodology to determine the values of $K_a$ for boronic acids and saccharides was adapted from work by Hall and coworkers. [13a, 13b]

A boronic acid (B) and a saccharide (S) were assumed to bind in one modality, B·S:

$$B + S \rightleftharpoons B \cdot S$$

$$K_a = \frac{[B \cdot S]}{[B][S]}$$

The [B·S]/[B] ratio was determined by the integration of aryl protons of the boronic acid·saccharide complex and the free boronic acid. The individual [B], [B·S], and [S] can be calculated from eq. 1-3.

$$[B \cdot S] + [B] = [B_T] \qquad \text{eq. 1}$$

$$\frac{[B \cdot S]}{[B]} + 1 = \frac{[B_T]}{[B]}$$

$$[B] = \frac{[B_T]}{\frac{[B \cdot S]}{[B]} + 1}$$

$$[B \cdot S] = \frac{[B \cdot S]}{[B]}[B], \text{ where } [B] \text{ is calculated from } eq. 1 \qquad \text{eq. 2}$$

$$[B \cdot S] + [S] = [S_T]$$

$$[S] = [S_T] - [B \cdot S], \qquad \text{eq. 3}$$
where $-[B \cdot S]$ is calculated from $eq$ 2

Each value of $K_a$ arose from at least two independent experiments with freshly prepared solutions, and each experiment consisted of a titration with 6-9 different concentrations.

All NMR spectra were analyzed with Topspin 3.0 software from Bruker AXS. NMR experiments were done in a 0.10 M $NaH_2PO_4$ buffer, pH 7.4, containing $D_2O$ (2% v/v). $^1$H NMR experiments consisted of the first increment of a 2D NOSY with gradients for improved water suppression.

A. Representative Procedure for Making a Phenylboronic Acid Solution $NaH_2PO_4$ (3.0 g, 25 mmol) and PBA (phenylboronic acid, 458 mg, 3.75 mmol) were dissolved in distilled, deionized water in a volumetric flask (~200 mL $H_2O$, 5 mL $D_2O$). The pH was adjusted carefully to 7.4 using 10 M NaOH, and additional water was added for a final volume of 250 mL. Final solutions were 15 mM in the boronic acid (PBA=solution 1; benzoboroxole=solution 2) in 0.10 M sodium phosphate monobasic buffer, pH 7.4, containing $D_2O$ (2% v/v).

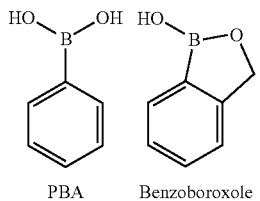

PBA          Benzoboroxole

Determination of the Value of $K_a$ for PBA and Fructose

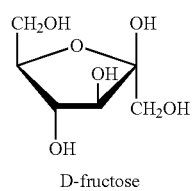

D-fructose

To a 25-mL volumetric flask, D-fructose (674 mg, 3.75 mmol) and ~20 mL of solution 1 was added. The solution was adjusted carefully to pH 7.4 by the addition of 10 M NaOH. (The volume of added NaOH was used in the calculation of the boronic acid concentration.) The volume was then increased to 25 mL by adding solution 1. This procedure resulted in a pH 7.4 solution of PBA (15 mM), D-fructose (150 mM), $NaH_2PO_4$ (0.10 M), and $D_2O$ (2% v/v) (solution A). Mixing various volumes of solution 1 and solution A generated fructose concentrations in the range of 4-14 mM. The [B·S]/[B] ratio was determined for every concentration as follows.

Representative Procedure for Determining the Chemical Shifts of Aryl Protons in Bound and Free Boronic Acids A $^1$H-NMR spectra of solution 1 (FIG. 13A) and solution A (FIG. 13B) were acquired. The two spectra were overlaid to determine which peaks belonged to the bound boronic acid and free boronic acid (FIG. 13C). This analysis was used to interpret the spectra from the titrations with sugars (FIG. 13D).

Determination of the Value of $K_a$ for Benzoboroxole and Fructose

Figure 14:
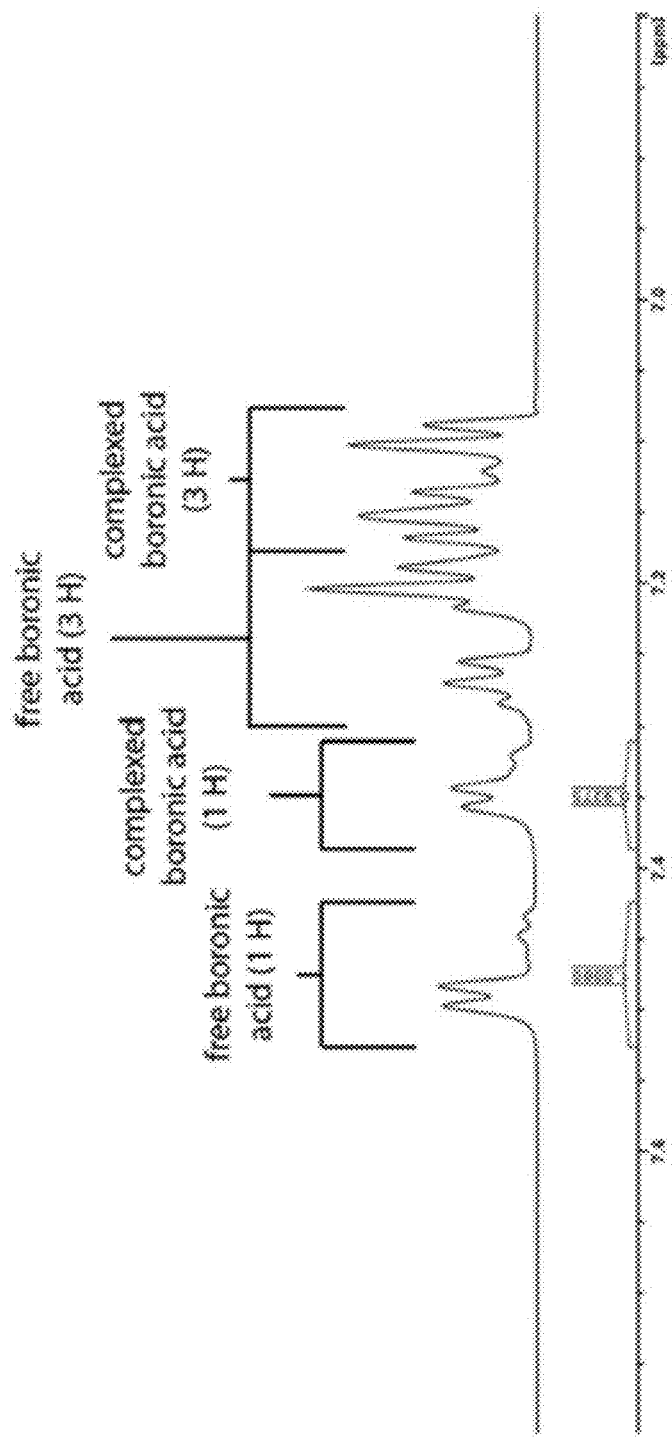
FIG. 14 is a representative $^1$H NMR spectrum that was used to determine the $K_a$ value for benzoboroxole and fructose (10.3 mM). Peaks corresponding to the aryl protons in bound and free boronic acid were determined as described in Example 2 and FIG. 13. The [B·S]/[B] ratio was calculated from the isolated peaks for the complex ($^1$H, 7.31-7.38 ppm, a mixture of isomeric species) and the isolated peaks for the free boronic acid (1H, 7.43-7.53 ppm, a mixture of isomeric species). Additional saccharide decreased the integration of the small peak at 7.44 ppm equally with that at 7.49 ppm, which arise from free boronic acid; and the shoulder peak at 7.31 ppm increased equally with that at 7.35 ppm, which arises from the complex.

To a 25-mL volumetric flask, D-fructose (674 mg, 3.75 mmol) and ~20 mL of solution 2 was added. The solution was adjusted carefully to pH 7.4 by the addition of 10 M NaOH. (The volume of added NaOH was used in the calculation of the boronic acid concentration.) The volume was then increased to 25 mL by adding solution 2. This procedure resulted in a pH 7.4 solution of benzoboroxazole (15 mM), D-fructose (150 mM), $NaH_2PO_4$ (0.10 M), and $D_2O$ (2% v/v) (solution B). Mixing various volumes of solution 2 and solution B generated fructose concentrations in the range of 4-14 mM. The [B·S]/[B] ratio was determined as depicted in FIG. 14. A value for $K_a$ was calculated for every concentration as described above.

Determination of the Value of $K_a$ for PBA and Glucose

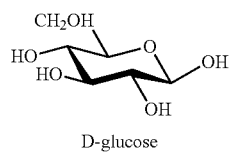

D-glucose

Figure 15:
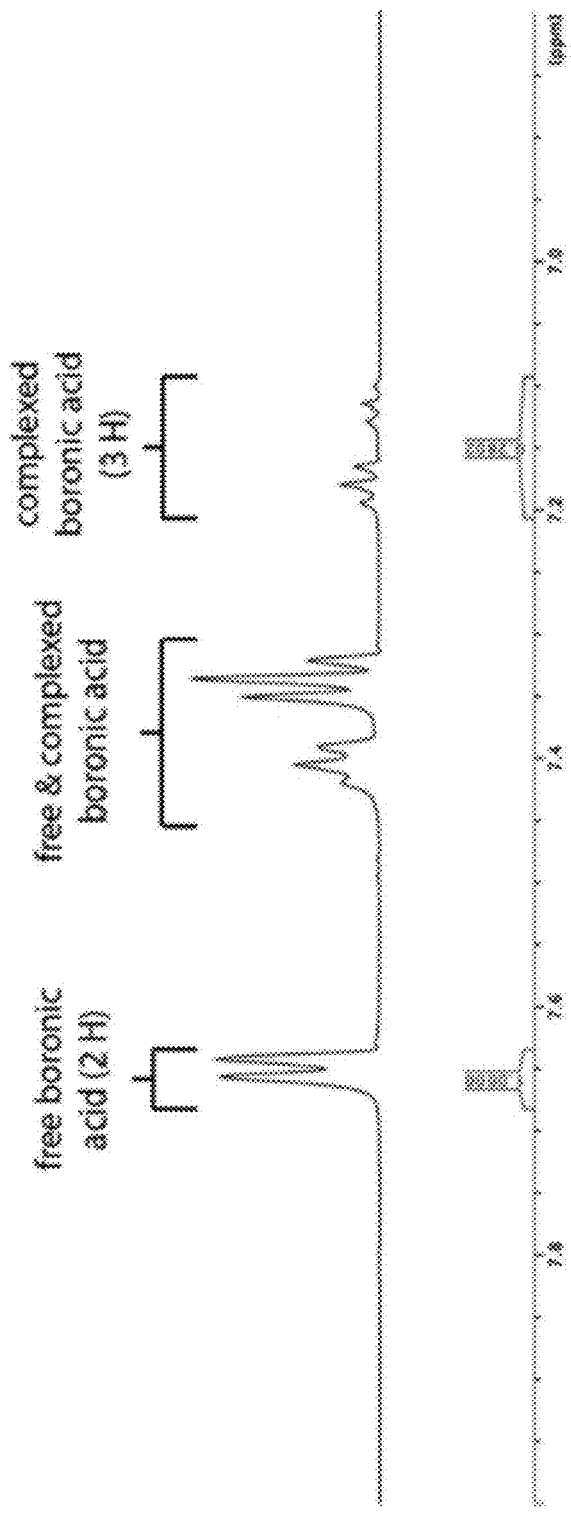
FIG. 15 is a representative $^1$H NMR spectrum that was used to determine the Ka value for PBA and glucose (44.9 mM). Peaks corresponding to the aryl protons in bound and free boronic acid were determined a described above. The [B·S]/[B] ratio was calculated from the isolated peaks for the complex (3H, 7.09-7.21 ppm) and the peaks for the free boronic acid (2H, 7.64-7.68 ppm).

To a 25-mL volumetric flask, D-glucose (2.25 g, 12.5 mmol) and ~20 mL of solution 1 was added. The solution was adjusted carefully to pH 7.4 by the addition of 10 M NaOH. (The volume of added NaOH was used in the calculation of the boronic acid concentration.) The volume was then increased to 25 mL by adding solution 1. This procedure resulted in pH 7.4 solution of PBA (15 mM), D-glucose (500 mM), 0.1 M $NaH_2PO_4$ (0.10 M), and $D_2O$ (2% v/v) (solution C). Mixing various volumes of solution 1 and solution C generated glucose concentrations in the range of 20-70 mM. The [B·S]/[B] ratio was determined as depicted in FIG. 15. A value for $K_a$ was calculated for every concentration as described above.

Determination of the Value of $K_a$ for Benzoboroxole and Glucose

Figure 16:
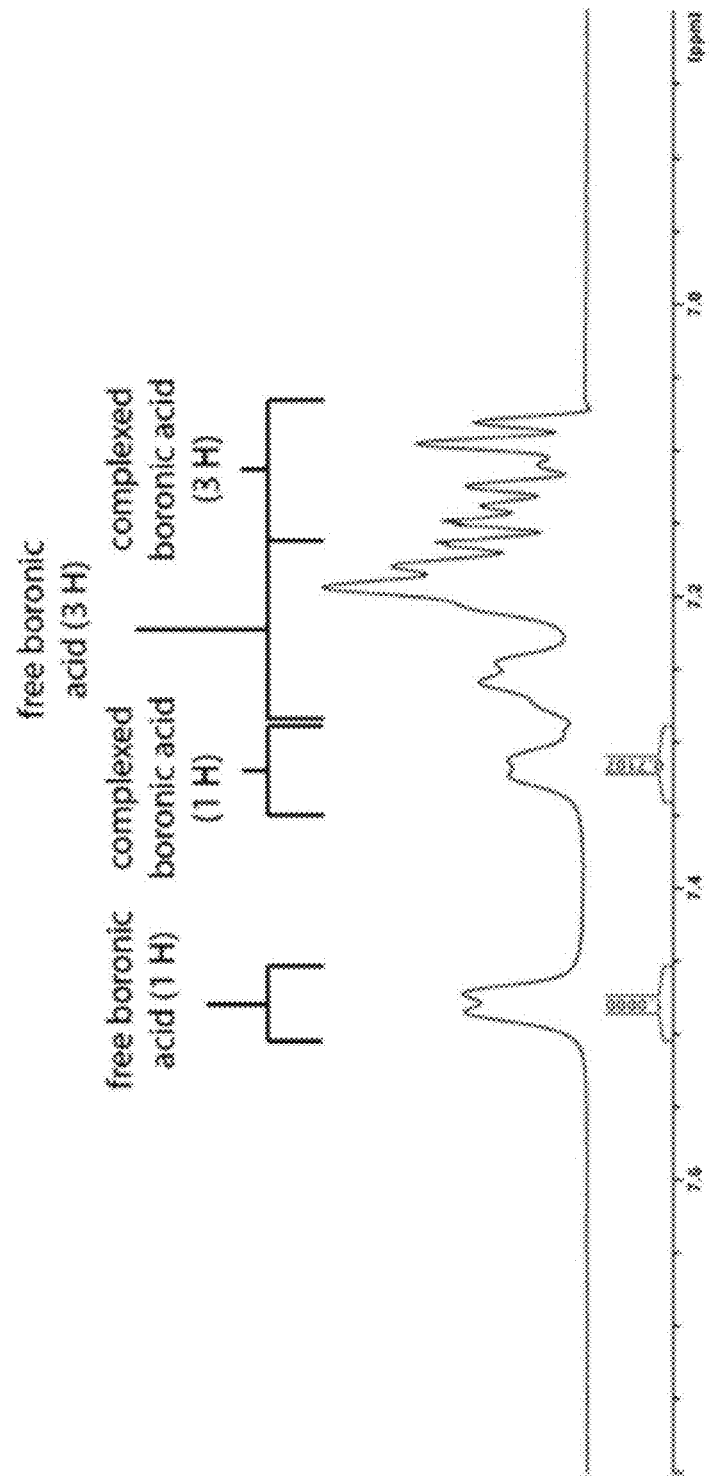
FIG. 16 is a representative $^1$H NMR spectrum that was used to determine the $K_a$ value for benzoboroxazole and glucose (32.9 mM). Peaks corresponding to the aryl protons in bound and free boronic acid were determined a described above. The [B·S]/[B] ratio was calculated from the isolated peaks for the complex ($^1$H, 7.29-7.34 ppm) and the isolated peaks for the free boronic acid ($^1$H, 7.45-7.51 ppm). Note the broadening of the aryl protons, which had been reported for NMR spectra of boronic acids in the presence of pyranose sugars. [13b]

To a 25-mL volumetric flask, D-glucose (2.25 g, 12.5 mmol) and ~20 mL of solution 2 was added. The solution was adjusted carefully to pH 7.4 by the addition of 10 M NaOH. (The volume of added NaOH was used in the calculation of the boronic acid concentration.) The volume was then increased to 25 mL by adding solution 2. This procedure resulted in a pH 7.4 solution of benzoboroxazole (15 mM), D-glucose (500 mM), $NaH_2PO_4$ (0.10 M), and $D_2O$ (2% v/v) (solution D). Mixing various volumes of solution 2 and solution D generated glucose concentrations in the range of 20-70 mM. The [B·S]/[B] ratio was determined as depicted in FIG. 16. Note the broadening of the aryl protons, which had been reported for NMR spectra of boronic acids in the presence of pyranose sugars. [13b] A value for $K_a$ was calculated for every concentration as described above.

Determination of the Value of $K_a$ for PBA and Neu5Ac

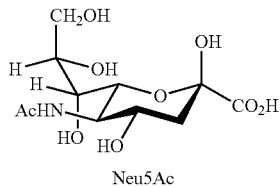

Neu5Ac

Figure 17:
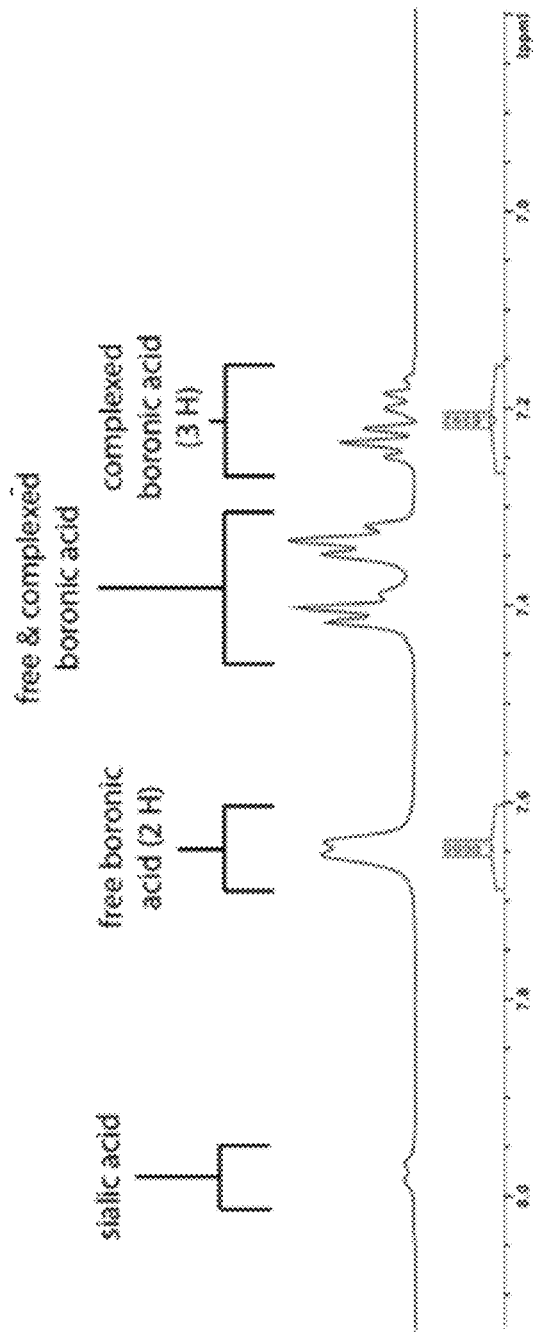
FIG. 17 is a representative $^1$H spectrum that was used to determine the $K_a$ value for PBA with Neu5Ac (35.4 mM). Peaks corresponding to the aryl protons in bound and free boronic acid were determined a described above. The [B·S]/[B] ratio was calculated from the isolated peaks for the complex (3H, 7.15-7.26 ppm) and the isolated peaks for the free boronic acid (2H, 7.6-7.69 ppm). Note that the aryl peaks have been broadened by the addition of the saccharide.

To a 10-mL volumetric flask, Neu5Ac (1.53 g, 5.0 mmol) and ~20 mL of solution 1 was added. The solution was adjusted carefully to pH 7.4 by the addition of 10 M NaOH. (The volume of added NaOH was used in the calculation of the boronic acid concentration.) The volume was then increased to 25 mL by adding solution 1. This procedure resulted in a pH 7.4 solution of PBA (14.2 mM), Neu5Ac (500 mM), $NaH_2PO_4$ (0.10 M), and $D_2O$ (2% v/v) (solution E). Mixing various volumes of solution 1 and solution E, generated Neu5Ac concentrations in the range of 7-65 mM. The [B·S]/[B] ratio was determined as depicted in FIG. 17. A value for $K_a$ was calculated for every concentration as described above.

Determination of the Value of $K_a$ for Benzoboroxole and Neu5Ac

Figure 18:
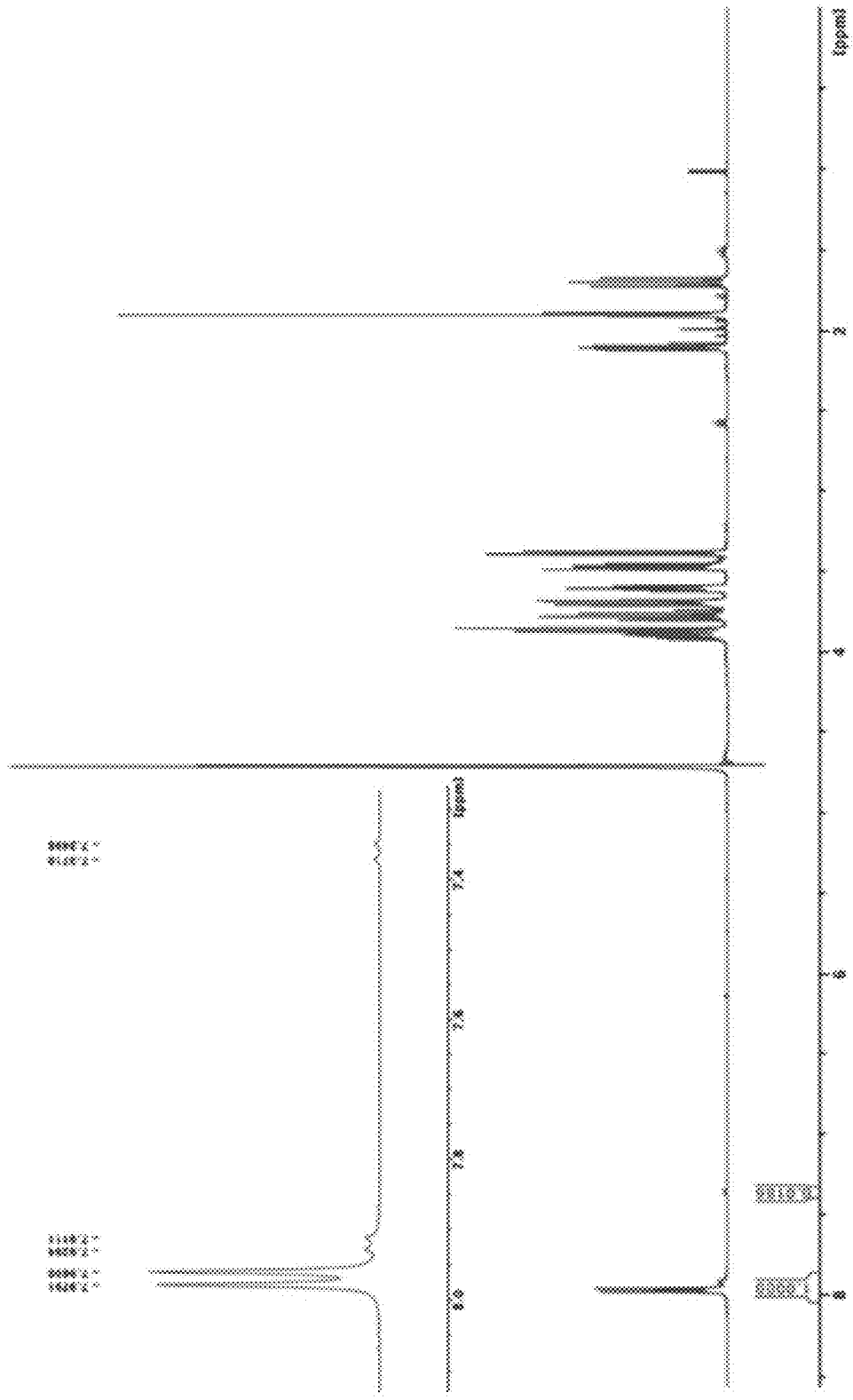
FIG. 18 illustrates the $^1$H NMR spectrum of Neu5Ac. This spectrum indicates a small peak that overlapped with the aromatic regions of the boronic acids. This peak was subtracted out of all NMR spectra used to evaluate the interaction of benzoboroxazole and Neu5Ac.
Figure 19:
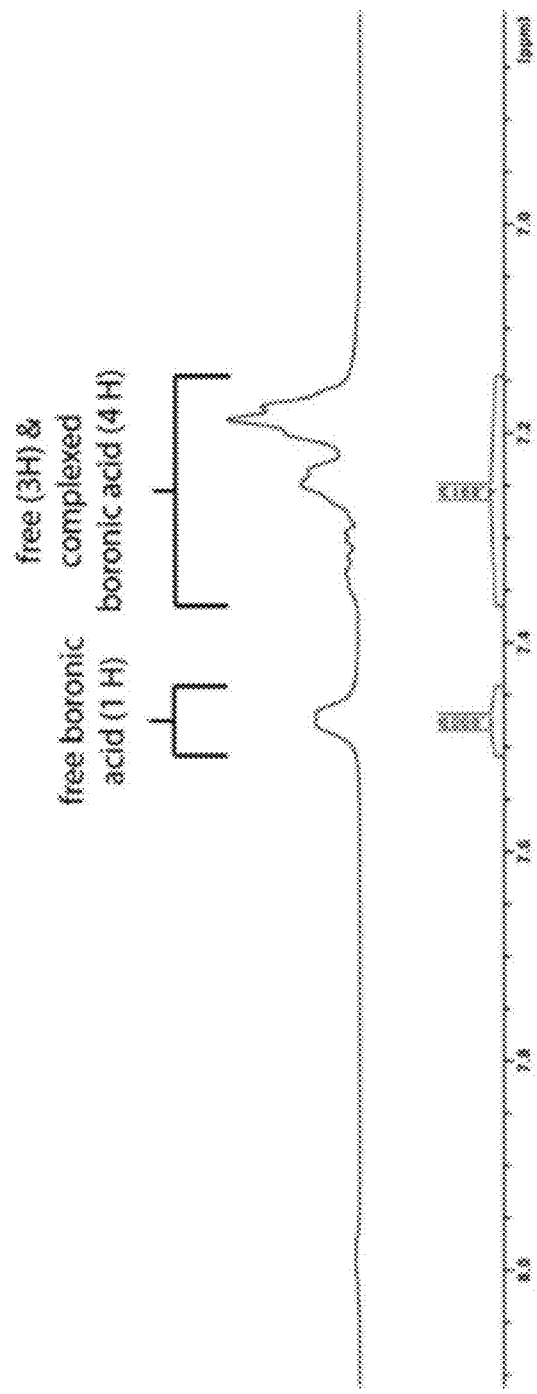
FIG. 19 is a representative $^1$H spectrum that was used to determine the $K_a$ value for benzoboroxazole with Neu5Ac (14.4 mM). Peaks corresponding to the aryl protons in bound and free boronic acid were determined as described in Example 2. The [B·S]/[B] ratio was determined from the isolated peaks for the free boronic acid (1H, 7.44-7.51 ppm) and the remainder of the aromatic region (7.15-7.36 ppm), which represented 3H from the free boronic acid and all 4 aromatic protons from the complex. Unlike fructose and glucose, the single isolated proton of the complexed species (7.33 ppm) was too broad to integrate accurately, and the entire region was used instead.

To a 10-mL volumetric flask, Neu5Ac (1.56 g, 5.0 mM) and ~20 mL of solution 2 was added. The solution was adjusted carefully to pH 7.4 by the addition of 10 M NaOH. (The volume of added NaOH was used in the calculation of the boronic acid concentration.) The volume was then increased to 25 mL by adding solution 2. This procedure resulted in a pH 7.4 solution of benzoboroxazole (14.2 mM), Neu5Ac (500 mM), $NaH_2PO_4$ (0.10 M), and $D_2O$ (2% v/v) (solution F). Mixing various volumes of solution 2 and solution F generated Neu5Ac concentrations in the range of 7-65 mM. The $K_a$ value was calculated for every concentration as previously described. The [B·S]/[B] ratio was determined as illustrated in FIGS. 18 and 19. Apparent in the $^1$H NMR spectrum of Neu5Ac (FIG. 18) is a small peak that overlapped with the aromatic regions of the boronic acids. This peak was subtracted out of all NMR spectra used to evaluate the interaction of benzoboroxazole and Neu5Ac. Unlike similar experiments with fructose and glucose, the single isolated proton of the complexed species (7.33 ppm) was too broad to integrate accurately, and the entire region was used instead. A value for $K_a$ was calculated for every concentration as described above.

Table 1 summaries $K_a$ data measured as described above with comparison to literature values. Measured $K_a$ values are in agreement with those measured by others employing alternative assays. Both PBA and benzoboroxole were found to have greater affinity for Neu5Ac than for glucose. Benzoboroxole was found to have greater affinity than PBA for each saccharide measured.

TABLE 1

Values of $K_a$ ($M^{-1}$) for boronic acids and saccharides

| Boronic Acid | D-fructose | D-glucose | Neu5Ac | Method | Ref. |
|---|---|---|---|---|---|
| PBA | 128 ± 20 | 5 ± 1 | 13 ± 1 | $^1$H NMR in $H_2O$ containing $D_2O$ (2% v/v) [a] | This work |
|  | 160 | 4.6 | 21 | Competition with alizarin red S [a] | [b] |
|  | 79 | 0 | — | $^1$H NMR in $D_2O$ (100% v/v) [a] | [c] |
|  | — | — | 11.6 ± 1.9 | $^{11}$B NMR in $H_2O/D_2O$/MeOH mixture | [d] |
| Benzo-boroxole | 336 ± 43 | 28 ± 4 | 43 ± 5 | $^1$H NMR in $H_2O$ containing $D_2O$ (2% v/v) [a] | This work |
|  | 606 | 17 | — | $^1$H NMR in $D_2O$ (100% v/v) [a] | [c] |

TABLE 1-continued

Values of $K_a$ ($M^{-1}$) for boronic acids and saccharides

| Boronic Acid | D-fructose | D-glucose | Neu5Ac | Method | Ref. |
|---|---|---|---|---|---|
| | — | 31 | — | Competition with alizarin red S [a] | [e] |

[a] Values were determined in 0.10M sodium phosphate buffer, pH 7.4;
[b] G. Springsteen, B. Wang, Tetrahedron 2002, 58, 5291-5300;
[c] M. Dowlut, G. Dennis, J. Am. Chem. Soc. 2006, 128, 4226-4227;
[d] K. Djanashvili, L. Frullano, J. A. Peters, Chem. Eur. J. 2005, 11, 4010-4018;
[e] M. Bérubé, M. Dowlut, D. G. Hall, J. Org. Chem. 2008, 73, 6471-6479.

Example 3: Conjugation of 5-Amino-2-Hydroxymethylphenylboronic Acid to RNase A Generating Benzoboroxole-Boronated RNase A To display benzoboroxole moieties on RNase A, 5-amino-2-hydroxymethyl-phenylboronic acid (1) was conjugated to protein carboxyl groups by condensation using a carbodiimide:

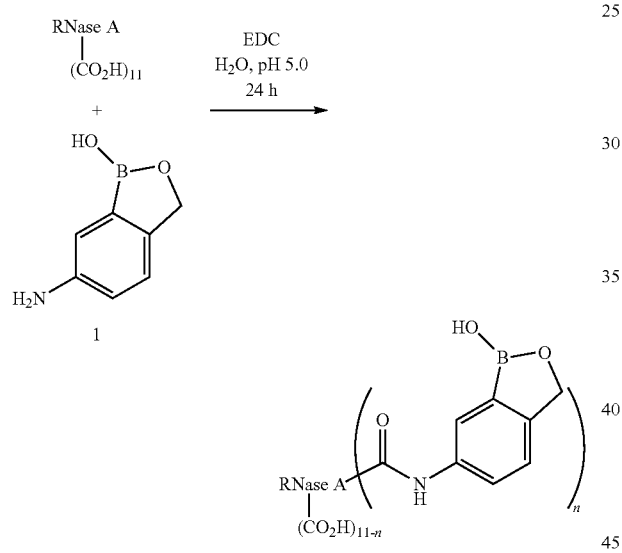

Figure 1A:
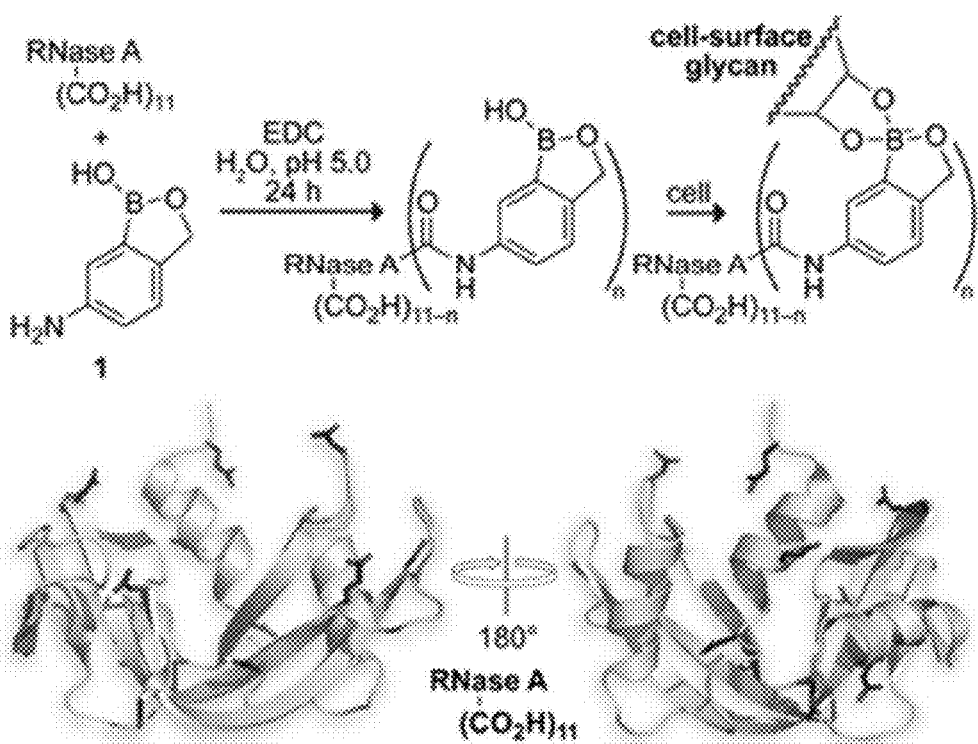
FIGS. 1A and 1B illustrate, respectively, a scheme showing exemplary boronation of RNase A with benzoboroxole groups (A) and its putative mechanism for expediting cellular delivery (B). The location of each carboxyl group of RNase A is depicted in the ribbon diagram (PDB entry 7rsa; [14])
Figure 1B:
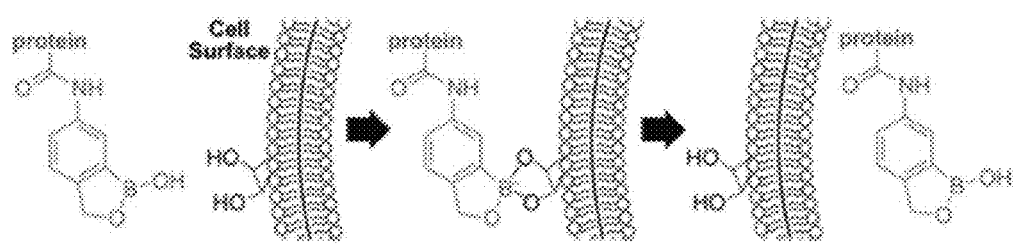

Also see Scheme 1 (FIG. 1A). As noted below of the 11 carboxyl groups of RNase A, on average 5.7±1.6 were condensed with benzoboroxole as determined by mass spectrometry.

5-Amino-2-hydroxymethylphenylboronic acid (1, 320 mg, 1.70 mmol) was added to 30 mL of distilled, deionized $H_2O$, and the resulting solution was adjusted to pH 5.0 with NaOH. To this solution was added RNase A (200 mg, 15 μmol), followed by EDC (640 mg, 3.30 mmol), and the pH was adjusted again to 5.0 with NaOH. The reaction mixture was incubated at ambient temperature overnight on a nutating mixer by BD (Franklin Lakes, N.J.). Additional EDC (360 mg, 1.9 mmol) was added, and the solution was incubated at the same conditions for 3.5 h (24 h total). The solution was then subjected to centrifugation (5 min at 1000 rpm, and 5 min at 5000 rpm) to remove insoluble boronic acid, and dialyzed (3500 molecular weight cutoff) against distilled, deionized $H_2O$ for 3 d at 4° C., with daily water exchanges. The solution was then passed through a 0.45-μm filter and loaded onto a 5-mL HiTrap Heparin HP column. To prepare a high-salt buffer, NaCl (58.4 g, 1.00 mol) was added to 100 mL of a 10× stock solution of PBS. This solution was diluted with distilled, deionized $H_2O$ to a final volume of 1 L, and adjusted to pH 7.4, making a buffer of PBS plus an additional 1 M NaCl. The column was washed with 75 mL of PBS buffer, and protein was eluted with a linear gradient of 225 mL of additional NaCl (0.0-1.0 M) in PBS buffer. Fractions were collected, pooled, concentrated, stored at 4° C., and analyzed by MALDI-TOF mass spectrometry.

Figure 20A:
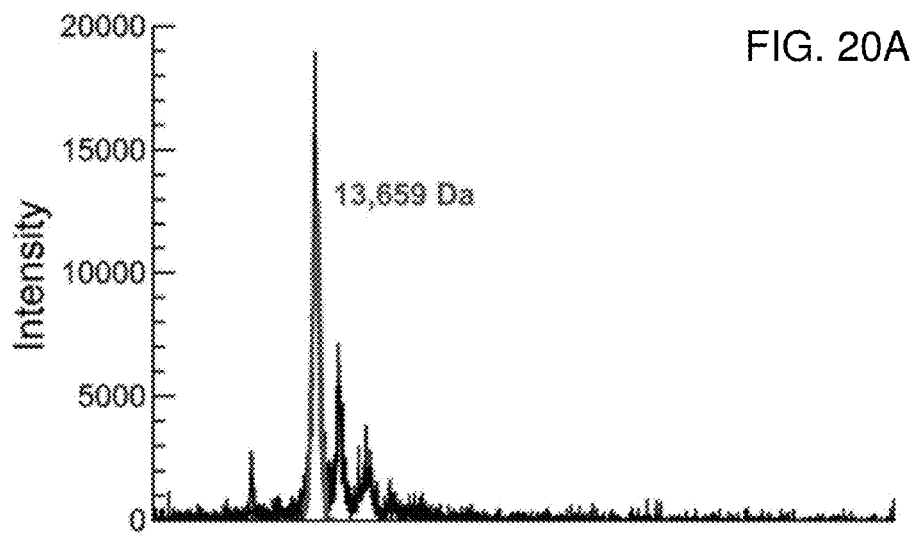
FIGS. 20A and 20B illustrate MALDI-TOF spectra of (20A) unmodified RNase A and (20B) boronated RNase. Data were fitted to a Gaussian curve (red line). The observed molecular mass of unmodified RNase A (13,659 Da) was subtracted from the observed molecular mass of boronated RNase A (14,641 Da) to give 982 Da. This value was divided by the molecular mass of 5-amino-2-hydroxymethylphenylboronic acid after correcting for the water lost during conjugation (148.95 Da–18.02 Da=130.93 Da) to give 7.5±2.0 boronic acids conjugated to RNase A, where SD=2.0 arises from the SD of the Gaussian fit, 265.2 Da, divided by 130.93 Da.
Figure 20B:
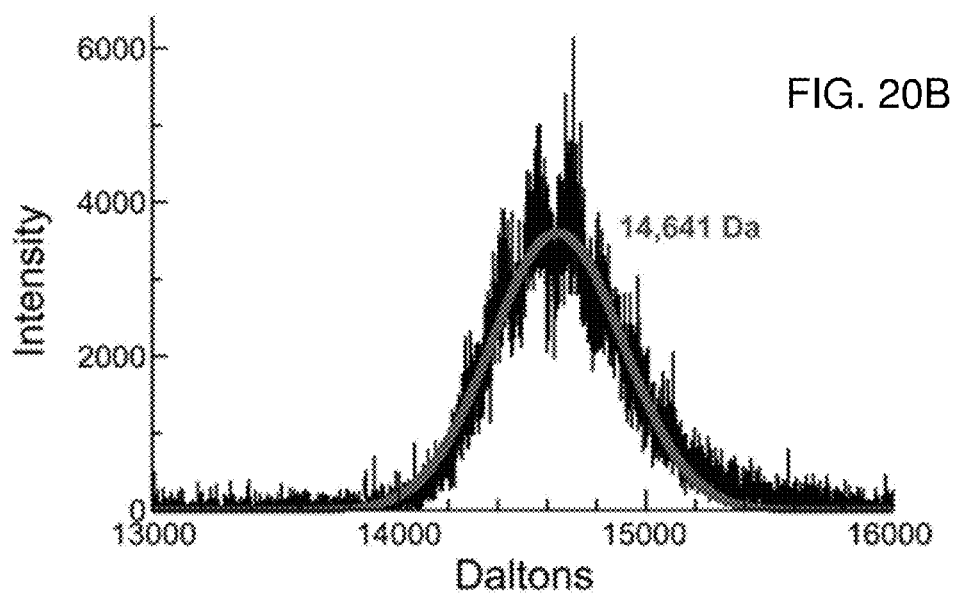

The mass spectrum between 13-16 kDa was fitted to a Gaussian curve with Graph Pad Prism version 5.02 software to determine the average mass (see FIG. 20). Specifically, the mean molecular mass determined for the conjugated RNase A (14,664 Da) was subtracted from the observed molecular mass of unmodified RNase A (13,682 Da) to give 982 Da. This value was divided by the molecular mass of 5-amino-2-hydroxymethylphenylboronic acid corrected for the loss of water during conjugation (185.42 Da-18.02 Da=167.40 Da) to give 5.9±1.6 phenylboronic acids conjugated to RNase A, where SD=1.6 arises from the SD of the Gaussian fit, 265.2 Da, divided by 167.42 Da.

Example 4: Conjugation of 3-Amino-Phenylboronic Acid to RNase A Generating PBA-Boronated RNase A PBA boronated RNase A was synthesized similarly to benzoboroxole-boronated RNase A as described in Example 3.

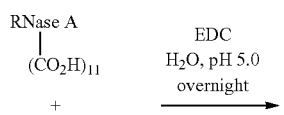

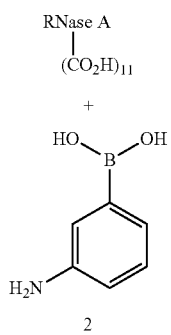

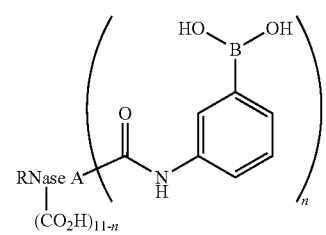

To 30 mL of double deionized H$_2$O was added 3-aminophenylboronic acid (2, 118 mg, 0.9 mmol) and the pH of the solution was adjusted to 5.0 with NaOH. To this solution RNase A (100 mg, 7 μmol) was added, followed by EDC (320 mg, 1.7 mmol), and the pH was re-adjusted to 5.0 with NaOH. Reaction was incubated at ambient temperature overnight on a nutating mixer. The solution was then centrifuged briefly (5 min at 1 k rpm, 5 min at 5 k rpm) to remove insoluble boronic acid and dialyzed (3500 MWCO) against double deionized H$_2$O for 3 d at 4° C., with daily water exchanges. Proteins were loaded onto a 1 mL HiTrap Heparin HP column. To prepare a high-salt buffer, NaCl (58.4 g, 1.00 mol) was added to 100 mL of a 10× stock solution of PBS. This solution was diluted with distilled, deionized H$_2$O to a final volume of 1 L, and adjusted to pH 7.4, making a buffer of PBS plus an additional 1 M NaCl. The column was washed with 30 mL of PBS buffer, and protein was eluted with a linear gradient of 90 mL of additional NaCl (0.0-1.0 M) in PBS buffer. Fractions were collected, pooled, and analyzed by MALDI-TOF mass spectrometry.

The mass spectrum between 13-16 kDa was fitted to a Gaussian curve with Graph Pad Prism version 5.02 software to determine the average mass as described above. Unmodified RNase A control: measured mass 13,657±285.16 Da, expected mass 13,682 Da, therefore, the correction factor=13,682−13,657=25 Da. PBA RNase A: measured mass 14,285±269.7 Da; adding correction factor=gives correct mass of 14,285+25=14,310 Da. Subtracting unmodified RNase mass from corrected mass of conjugate gives 14,310−13,682=628 Da. Each PBA conjugation is 118.79 Da, so on average 5.3±2.3 PBA are conjugated to RNase A.

Example 4: Preparation of Inactivated, Benzoboroxole-Boronated RNase A

RNase A was inactivated by treatment with 2-bromoacetic acid. RNase A (38 mg, 2.8 μmol) was dissolved in 575.5 μL of 0.10 M sodium acetate buffer, pH 4.9. In a separate solution, 2-bromoacetic acid (123 mg, 883 μmol) was dissolved in 9.2 mL of 0.10 M sodium acetate buffer. The resulting solutions were adjusted to pH 5.2. An aliquot (288 μL) of the 2-bromoacetic acid solution was added to the RNase A solution to generate a final concentration of 32 mM 2-bromoacetic acid and 3.2 mM RNase A. The reaction mixture was incubated at ambient temperature for 24 h on a nutating mixer, after which the reaction was dialyzed overnight against distilled, deionized H$_2$O.

The inactivated RNase A was then loaded onto a Mono S HR 16/10 cation exchange FPLC column from Pharmacia. The column was washed with a 40-mL linear gradient of NaCl (0.00-0.05 M) in 10 mM sodium phosphate buffer, pH 6.0, and eluted with a 603-mL linear gradient of NaCl (0.05-0.40 M) in 10 mM sodium phosphate buffer, pH 6.0. Fractions were collected, pooled, and dialyzed overnight at 4° C. against 50 mM sodium acetate buffer, pH 5. Inactivated RNase A was then loaded onto a 5-mL HiTrap Heparin HP column. The column was washed with 10 mL of 50 mM sodium acetate buffer, pH 5.0, and eluted with a 200-mL linear gradient of NaCl (0.0-0.4 M) in 50 mM sodium acetate buffer, pH 5.0. Fractions were collected, and analyzed by MALDI-TOF mass spectrometry. Fractions with molecular mass greater than that of unmodified RNase A were pooled and dialyzed extensively with distilled, deionized H$_2$O at 4° C.

5-Amino-2-hydroxymethylphenylboronic acid (1) was then conjugated to the inactivated RNase A as described above. Briefly, to 0.5 mL of chemically inactivated RNase A (6 mg, 400 nmol) was added 5-amino-2-hydroxymethylphenylboronic acid (10 mg, 50 μmol), and adjusted to pH 5. EDC was then added (19 mg, 100 μmol), and the resulting solution was adjusted to pH 5. The reaction mixture was incubated at ambient temperature for 20.5 h on a nutating mixer before adding additional EDC (11 mg, 56 μmol), and then incubated for an additional 3.5 h. Inactivated, benzoboroxole-boronated RNase A was dialyzed against distilled, deionized H$_2$O and purified on a 1-mL HiTrap Heparin HP column as described for benzoboroxole-boronated RNase A.

Example 5: Preparation of BODIPY FL-Labeled Ribonucleases

A. Unmodified and benzoboroxole-conjugated RNase A were labeled with BODIPY FL. An aliquot (3.83 mL) of a solution of ribonuclease (120 μM) was adjusted to pH 8.3. BODIPY FL STP ester (5 mg; 9 μmol) was dissolved in 0.5 mL of DMF. To the solution of ribonuclease was added 125 μL of the BODIPY FL STP ester solution. The reaction mixture was incubated at ambient temperature on a nutating mixer for 4-6 h, and then incubated at 4° C. on a nutating mixer overnight. Labeled ribonuclease was loaded onto a 1-mL HiTrap Heparin HP column. The column was washed with 30 mL of 10 mM sodium phosphate buffer, pH 6.0. The protein was eluted with a 60-mL linear gradient of NaCl (0.0-1.0 M) and pH (6.0-7.4) in 10 mM sodium phosphate buffer, pH 7.4. Fractions were collected, pooled, concentrated, and analyzed by SDS-PAGE and MALDI-TOF mass spectrometry.

Labeled ribonucleases were dissolved in at least a 10× volume of DPBS, passed through a 0.45-μm syringe filter from Whatman (Piscataway, N.J.), and re-concentrated before being used in assays. In this manner, the proteins were dissolved in solution that was largely DPBS.

Concentrations of proteins were determined by UV spectroscopy using the extinction coefficient of RNase A at 278 nm ($\epsilon$=0.72 (mg·mL$^{-1}$)$^{-1}$·cm$^{-1}$). [54] The absorbance of benzoboroxole was found to be negligible, contributing <5% to the A$_{278\ nm}$ of the boronated ribonuclease. The concentration of labeled ribonucleases was corrected for fluorophore absorbance by using the manufacturer's protocol (http://tools.invitrogen.com/content/sfs/manuals/mp00143.pdf). Percent labeling was determined by UV spectrometry at 504 nm using the extinction coefficient of BODIPY FL ($\epsilon$=68,000 M$^{-1}$·cm$^{-1}$) as per the manufacturer's protocol. The boronated-RNase A conjugate achieved 30% labeling, whereas RNase A achieved 89% labeling.

B. Unmodified and PBA-boronated RNase A were labeled with BODIPY FL similar to unmodified and benzoboroxole-boronated RNase A described above. An aliquot (20 mL) of a solution of a fraction of PBA-boronated RNase A (fraction 3) and unmodified ribonuclease (45 μM) was adjusted to pH 8.8. BODIPY-FL STP ester (5 mg; 9 μmol) was dissolved in 0.5 mL of DMF. To the solutions of ribonuclease was added 250 μL of the BODIPY FL STP ester solution. PBS was added to the solution for a total volume of 50 mL. The reaction mixture was incubated at ambient temperature on a nutating mixer for approximately 2 h, and then dialyzed against PBS at 4° C. overnight. Labeled ribonuclease was loaded onto a 1-mL HiTrap Heparin HP column. The column was washed with 30 mL of 10 mM sodium phosphate buffer, pH 7.4. The protein was eluted with a 60-mL linear gradient of 0.0-1.0 M NaCl in 10 mM sodium phosphate buffer, pH 7.4. Fractions were collected, pooled, concentrated, and analyzed by SDS-PAGE and MALDI-TOF mass spectrometry.

Concentrations of proteins were determined by UV spectrometry using the extinction coefficient of RNase A at 278 nm ($\epsilon$=0.72 (mg·mL-1)-1 cm-1) [54]. The concentration of labeled ribonucleases was corrected for fluorophore absorbance by using the manufacturer protocol (web site: tools.invitrogen.com/content/sfs/manuals/mp00143.pdf). Percent labeling was determined by UV spectrometry at 504 nm using the extinction coefficient of BODIPY FL ($\epsilon$=68,000 M-1·cm-1) as per the manufacturer's protocol. Boronated RNase A achieved 30% labeling and RNase A achieved 59%.

Example 6: Heparin-Affinity Assays

To assess the affinity of boronated proteins for oligosaccharides the retention of boronated proteins compared to unmodified protein can be measured on a heparin column.

For example, the affinity of unmodified and benzoboroxole-boronated RNase A for heparin was assessed by retention on a 1.0-mL HiTrap Heparin HP column (GE Healthcare, Piscataway, N.J.). Unmodified and benzoboroxole-boronated RNase A were mixed in a 1:1 ratio (2.0 mg each) in DPBS, and the resulting solution was loaded onto the column. The column was washed with 5 mL of PBS, followed by elution with 45 mL of a linear gradient of NaCl (0.0-1.0 M) in PBS. Elution was monitored by absorbance at 280 nm, and eluted proteins were identified by mass spectrometry. FIG. 2 illustrates an elution profile of a mixture of unmodified RNase A and benzoboroxole-boronated RNase A from a column of immobilized heparin (solid lines). A small amount of unmodified RNase A was apparent in peak B (FIG. 2). It is currently believed that benzoboroxole-boronated RNase A was able to complex to a small amount of unmodified RNase A and extend its elution time. The same assay was then repeated with 100 mM fructose in both buffers (FIG. 2, dashed line). To make fructose-supplemented buffers, fructose (18 g, 100 mmol) was added to 100 mL of a 10× stock solution of PBS, either no additional NaCl or NaCl (58.4 g, 1.00 mol) was added, and both buffers were diluted to a final volume of 1 L and adjusted to pH 7.4.

As shown in FIG. 2, benzoboroxole-boronated RNase A was indeed retained longer on the column. Addition of fructose in the buffer employed was shown to compete with immobilized heparin for boron complexation diminishing retention of benzoboroxole-boronated RNase A and indicating that prolonged retention of benzoboroxole-boronated RNase A was due to boron-saccharide complexation.

Example 7: Assessing the Affinity of Benzoboroxole-Boronated-RNase A for GD3 Ganglioside-Labeled Liposomes Employing Fluorescence Polarization Assays To evaluate the enhanced affinity of benzoboroxole-boronated RNase A for oligosaccharides, its affinity for ganglioside GD3 within a 1,2-dioleoyl-sn-glycero-3-phosphocholine (DOPC) liposome was measured. This ganglioside has two sialic acid residues and is overexpressed on the surface of cancer cells. [15] By using fluorescence polarization to analyze binding, it was demonstrated that boronation increased the affinity of the protein for the ganglioside, an effect that was abrogated by fructose (FIG. 3). The $K_d$ value of benzoboroxole-boronated protein for GD3 ganglioside liposomes was (54±11) μM. This affinity is ~430 fold greater than that for the binding of a single benzoboroxole to Neu5Ac (Table 1), consistent with a multivalent interaction between the benzoboroxole-boronated protein and the ganglioside.

Liposomes were formed by transferring DOPC (dissolved in chloroform solution) and GD3 gangliosides (dissolved in 63:35:5 chloroform/methanol/water) to glass tubes and drying them under Ar (g) and then under vacuum. Lipids were re-suspended in 25 mM HEPES buffer, pH 7.0, containing NaCl (75 mM). The solution of lipids was mixed by vortexing for 2 min, and incubated at 37° C. for 1 h. For DOPC liposomes, DOPC was resuspended at a concentration of 5 mM. For GD3 ganglioside-labeled liposomes, DOPC and GD3 gangliosides were mixed at 3 mM and 2 mM concentrations, respectively. Large unilammelar vesicles were formed by extrusion through a 0.1-μm polycarbonate filter from Whatman (GE Healthcare, Piscataway, N.J.). This process produces a population of vesicles of near uniform size (~100-150 nm diameter as measured by dynamic light scattering). A portion of the DOPC lipids before extrusion were aliquoted as a control.

Fluorescence polarization assays were performed using 50 nM BODIPY FL-labeled unmodified and benzoboroxole-boronated RNase A in black NBS 96-well plates (Corning Costar, Lowell, Mass.). These ribonucleases were incubated with DOPC liposomes (625 μM total lipid) or GD3 ganglioside-labeled liposomes (375 μM DOPC, 250 μM GD3 ganglioside=625 μM total lipid) in 25 mM HEPES buffer, pH 7.0, containing NaCl (75 mM) in the absence or presence of fructose (10 mM). In control wells, ribonucleases were incubated with non-extruded DOPC lipids. Fluorescence polarization at 470/535 nm with a G-factor of 1.257 was recorded after shaking the plate briefly and incubating at ambient temperature for 1 h. Control well polarization was subtracted from experimental well polarization for each ribonuclease. The assay was performed in triplicate.

Figure 21:
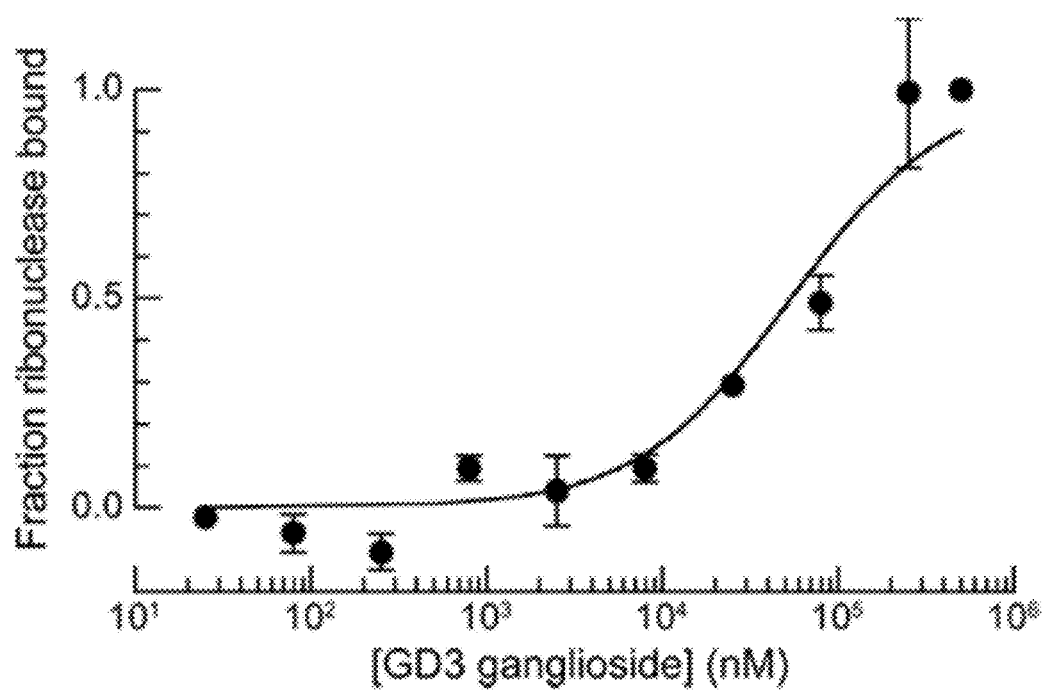
FIG. 21 illustrates fluorescence polarization data for the binding of phenylboronate-conjugated RNase A to GD3 ganglioside in liposomes. BODIPY FL-labeled phenylboronate-conjugated RNase A was incubated with liposomes containing GD3 ganglioside in 25 mM HEPES buffer, pH 7.0, containing NaCl (75 mM). Data points represent the mean (±SE) of duplicate experiments. Data were fitted to a binding isotherm as described in ref. [46] to give Kd=(54±11) µM.

The affinity of benzoboroxole-boronated RNase A for GD3 ganglioside-labeled liposomes was assessed by using serially diluted liposomes. GD3 ganglioside-labeled liposomes were serially diluted in 25 mM HEPES, pH 7.0, containing 75 mM with dilutions of 62.5 nM-1250 μM total lipid. Because the composition of these liposomes was 3:2 DOPC/GD3 ganglioside, this dilution resulted in a solution containing D3 ganglioside at 25 nM-500 μM. Control DOPC liposomes (with no GD3 ganglioside) were likewise diluted in the same buffer, producing solutions of 62.5 nM-1250 μM total lipid. Liposomes were then incubated with 50 nM BODIPY FL-labeled benzoboroxole-boronated RNase A in the same buffer in a black NBS 96-well plate. Fluorescence polarization was recorded after shaking the plate briefly and incubating at ambient temperature for 35 min. Fluorescence polarization from GD3 ganglioside-labeled liposomes was subtracted from that from DOPC-only liposomes, thereby correcting for binding to DOPC and for changes in solution viscosity. The assay was performed in duplicate. The fraction of labeled ribonuclease bound for each sample well was calculated by dividing its polarization from the polarization of ribonucleases incubated with the highest concentration of GD3 ganglioside (set at 100% bound). The value of $K_d$ was calculated by plotting the fraction bound against the concentration of GD3 ganglioside (see FIG. 21) and fitting the data to a binding isotherm as described in ref. [46] to give Kd=(54±11) μM.

Example 8: Cellular Internalization RNase Conjugates

Figure 4B:
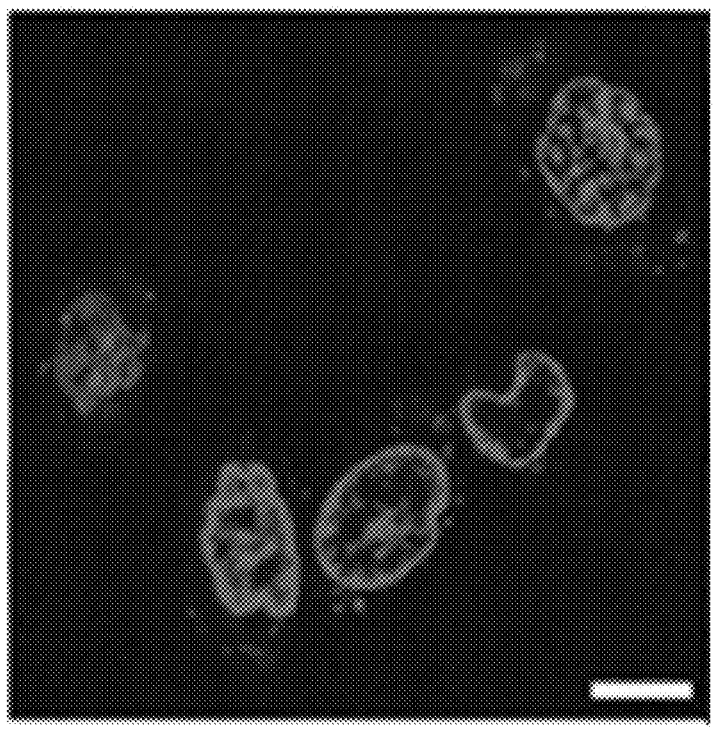
FIG. 4B is a confocal microscopy image of live Pro-5 cells incubated for 4 h with benzoboroxole-boronated RNase A (5 μM) that had been labeled covalently with a green fluorophore. Nuclei were stained blue with Hoechst 33322 (2 μg/mL). Scale bar: 10 μm.
Figure 4C:
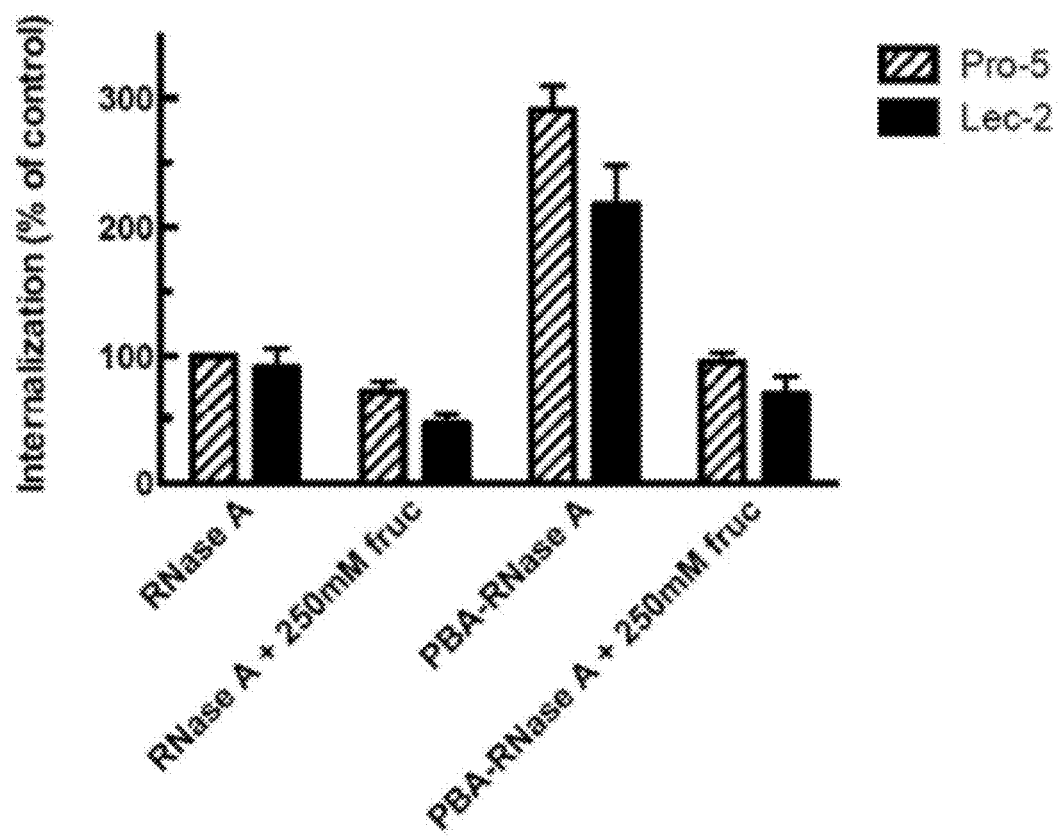
FIG. 4C is a graph of the results of flow cytometry experiments measuring internalization of unmodified and phenylboronate-boronated RNase A into Pro-5 and Lec-2 cells in the absence or presence of fructose (0.25 M). Flow cytometry data were normalized to the internalization of unmodified RNase A into Pro-5 cells. Error bars represent the SD.

To quantify cellular internalization, Fluorophore-labeled protein and flow cytometry were used to quantify cellular internalization of boronated protein. To determine concurrently if the pendant boronates elicited selectivity for cells with higher quantities of cell-surface sialic acid, a line of Chinese hamster ovary cells (Lec-2) was used. These cells have lower levels of sialic acid in their glycocalyx, than their progenitor line (Pro 5). [16]. As shown in FIG. 4A boronation of RNase A with benzoboroxole increased its cellular uptake by 4- to 5-fold in both cell lines tested. As shown in FIG. 4C boronation of RNase A with PBA increased its cellular uptake by 2.5-3 fold in both cell lines tested. In both cases, this enhancement was eliminated by addition of fructose.

Cell-surface sialic acid-content (comparing Pro-5 to Lec-2 cells) was not observed to affect uptake significantly. This result is consistent with the modest increase observed in the $K_a$ value for benzoboroxole with sialic acid versus glucose (Table 1).

Confocal microscopy of boronated protein (benzoboroxole-boronated RNase) demonstrated punctate staining (FIG. 4B), which is consistent with uptake by endocytosis following complexation with cell-surface saccharides.

A. Cell Culture

Cell lines were obtained from American Type Culture Collection (Manassas, Va.) and were maintained according to the recommended procedures. Cells were grown in a cell culture incubator at 37° C. under $CO_2$ (5% v/v) in flat-bottomed culture flasks. Cell medium was supplemented with GIBCO fetal bovine serum (FBS) (10% v/v), penicillin (100 units/mL), and streptomycin (100 μg/mL) in the appropriate cellular medium as follows: Pro-5, MEM α+ribonucleosides+deoxyribonucleosides; Lec-2, MEM α-ribonucleosides-deoxyribonucleosides; and K562, RPMI 1640. Cells were counted by hemocytometry for dispensing into 12-well plates (Corning Costar, Lowell, Mass.) or 8-well chambered coverglass slides (Nuc Lab-Tek II, Thermo Scientific).

B. Flow Cytometry Assays

BODIPY-FL was excited with a 488 nm solid-state laser and the emission was collected with a 530/30 bandpass filter. To collect the most reproducible data, for every flow cytometry experiment, the sensitivity (voltage) of the photomultiplier tube was set for all data collections using mid-range Rainbow beads from Spherotech (Lake Forest, Ill.) to a predetermined fluorescence target value. At least 10,000 cellular events were acquired for each sample. Data were analyzed using FlowJo 8.1.3 (Treestar, Ashland, Oreg.).

The day prior to an experiment, Pro-5 and Lec-2 cells were plated in 12-well plates at $1 \times 10^5$ cells/well. The day of the experiment, the appropriate amount of fructose was dissolved into the cellular medium to obtain a final fructose concentration of 250 mM, and the medium was passed through a 0.45-μm syringe filter from Whatman (Piscataway, N.J.). Non-fructose-containing medium was filtered likewise. Stock solutions of fluorescently labeled ribonucleases were diluted into the cell culture to a final concentration of 5 μM. Ribonucleases were incubated with cells for 4 h. Cells were then rinsed with PBS (2×400 μL), removed from the cell culture plate with trypsin (400 μL, 0.05% (1×) with EDTA; Invitrogen, Carlsbad, Calif.), placed in flow cytometry tubes containing 80 μL of FBS, and incubated on ice until analyzed by flow cytometry. Final fluorescence values were divided by the percent fluorophore labeling of the ribonuclease to determine the corrected value of fluorescence. Experiments were run twice in triplicate unless otherwise indicated. Data is illustrated in FIG. 4A and FIG. 4C.

C. Confocal Microscopy

Pro-5 cells were plated on Nunc Lab-tek II 8-well chambered coverglass 24 h before use and grown to 80% confluency. Cells were incubated with 5 μM BODIPY FL-labeled ribonucleases for 4 h. Cell nuclei were stained with Hoechst 33342 (Invitrogen, 2 μg/mL) for the final 15 min of incubation. Cells were then washed twice with PBS, suspended in PBS, and examined using a Nikon Eclipse C1 laser scanning confocal microscope. Results are illustrated in FIG. 4B.

Example 9: Assessing Cytosol Delivery

Although flow cytometry can quantify protein internalization into a cell, it does not differentiate between proteins in endosomes versus those in the cytosol. Delivery into the cytosol is important for the efficacy of numerous putative chemotherapeutic agents. Boronated RNase A retained ribonucleolytic activity (17±2% for benzoboroxole-boronated RNase A.) The activity loss is believed attributable, at least in part, to the modification of the carboxyl group of aspartic acid 121 on reaction with the boronic acid. Aspartic acid 121 is known to contribute to RNAse A activity (L. W. Schultz, D. J. Quirk, R. T. Raines, Biochemistry 1998, 37, 8886-8898). Boronated RNase A thus has the potential to be cytotoxic, if it can enter the cytosol.

Benzoboroxole-boronated RNase A was found to inhibit the proliferation of a line of human erythroleukemia cells (K-562; FIG. 5). The addition of fructose diminished cytotoxic activity, presumably by decreasing overall internalization of boronated RNase A. In contrast, chemically inactivated, benzoboroxole-boronated RNase A was much less cytotoxic, indicating that ribonucleolytic activity induced toxicity, not the pendant boronates. Boronation not only facilitates cellular uptake of an enzyme, but also allows for its delivery to the cytosol and the maintenance of its catalytic activity.

A. Ribonucleolytic Activity Assays

The ribonucleolytic activities of RNase A, boronated RNase A, and boronated inactive RNase A were determined by quantifying their ability to cleave 6-FAM-dArUdAdA-6-TAMRA, as described in [50]. Assays were carried out at ambient temperature in 2 mL of 0.10 M MES-NaOH buffer, pH 6.0, containing NaCl (0.10 M). Fluorescence data were fitted to the equation: $k_{cat}/K_M = (\Delta I/\Delta t)/(I_f - I_0)[E]$, in which $\Delta I/\Delta t$ is the initial reaction velocity, $I_0$ is the fluorescence intensity before addition of ribonuclease, $I_f$ is the fluorescence intensity after complete substrate hydrolysis, and [E] is the total ribonuclease concentration. The assay was performed in triplicate.

B. Cell-Proliferation Assays

The effect of unmodified and boronated RNase A on the proliferation of K-562 cells was assayed as described in For assays, 5 μL of a solution of the ribonuclease or PBS (control) was added to 95 μL of cells ($5.0 \times 10^4$ cells/mL). For co-treatment assays with fructose, ribonucleases were first serially diluted at 2× concentration, followed by addition of an equal volume of 2 M fructose in PBS to each ribonuclease dilution, resulting in a 1× ribonuclease [51] dilution as before but now containing 1 M fructose. Then, 5 μL of each dilution was added to cells as above, including a control of PBS containing 1 M fructose. Because 5 μL of samples were added to 95 μL of cells, the final concentration of fructose in each well was 50 mM.

After a 44-h incubation, K-562 cells were treated with [methyl-$^3$H]thymidine for 4 h, and the incorporation of radioactive thymidine into cellular DNA was quantitated by liquid scintillation counting. The results are shown as the percentage of [methyl-$^3$H]thymidine incorporated relative to control cells treated with PBS in FIG. 5. Data are the average of three measurements for each concentration, and the entire experiment was repeated in triplicate. Values for $IC_{50}$ were calculated by fitting the curves by nonlinear regression to the equation:

$$y=100\%/(1+10^{(log(IC_{50})-log\,[ribonuclease])h}),$$

in which y is the total DNA synthesis following the [methyl-$^3$H]thymidine pulse and h is the slope of the curve.

Example 10: Boronation of Lysozyme

Boronated lysozyme was synthesized similarly to boronated RNase A as described in Example 3. For the synthesis of the benzoboroxole-boronated lysozyme, 5-amino-2-hydroxymethylphenylboronic acid (1, 160 mg, 0.9 mmol) was added to 20 mL of double deionized H$_2$O and the pH of the solutions were adjusted to 5.0 with NaOH. To the solution was added lysozyme (from chicken egg white, 20 mg, 1.4 μmol), followed by EDC (320 mg, 1.7 mmol), and the pH was re-adjusted to 5 with NaOH. PBA-boronated lysozyme was analogously synthesized employing 3-aminophenyboronic acid (2, 160 mg, 1.2 mmol). Reactions were incubated at ambient temperature overnight on a nutating mixer. The reaction solutions were then centrifuged briefly (5 min at 1 k rpm, 5 min at 5 k rpm) to remove insoluble boronic acid and dialyzed (3500 MWCO) against double deionized H$_2$O for 3 d at 4° C., with daily water exchanges.

Proteins were loaded onto a 1 mL HiTrap Heparin HP column. The column was washed with 20 mL of 10 mM sodium phosphate buffer, pH 7.4. Protein was eluted with a 10 mL linear gradient of 0.0-1.5 M NaCl in 10 mM sodium phosphate buffer, pH 7.4. Fractions were collected, pooled, and analyzed by MALDI-TOF mass spectrometry. The mass spectrum between 13-16 kDa was fitted to a Gaussian curve with Graph Pad Prism version 5.02 software to determine the average mass and calculate the number of boronates conjugated/lysozyme.

Lysozyme control: 14,260±52 Da, expected 14,307 Da (from Sigma Aldrich website of similar protein with reference to Canfield, R. E., J. Biol. Chem., 238, 2698-2707 (1963)). Therefore, the correction factor=14,307 Da−14,260 Da=47 Da. For PBA-boronated lysozyme, the measured mass was 14,568±199 Da+47 Da (correction factor)=14,615±199 Da. Mass due to conjugated PBA is then 308 Da and the mass of each PBA is 118.79 Da. On average, 2.6±1.7 PBA are conjugated to the lysozyme. For benzoboroxole-conjugated lysozyme a similar calculation, using measured corrected mass for benzoboroxole-conjugated lysozyme of 14,700±187 Da, and mass/benzoboroxole conjugation of 167.4 Da, gives on average 2.3±1.1 benzoboroxole conjugated per lysozyme.

BODIPY FL-labeled lysozyme and BODIPY FL-labeled boronated lysozyme were synthesized similarly to BODIPY FL-labeled RNase A and boronated RNase A as described in Example 5. Lysozyme, PBA-boronated lysozyme, and benzoboroxole-boronated lysozyme were diluted with 0.1 M sodium bicarbonate buffer (pH 8.3) to 3 mg/mL in 550 μL total (1.65 mg, 115 nmol). To this was added 25 μL of 5 mg/mL BODIPY FL, STP ester dissolved in 0.1 M sodium bicarbonate buffer (pH 8.3) (0.125 mg, 231 nmol, 2×). An additional 575 μL of 0.1 M sodium bicarbonate buffer (pH 8.3) was added. The reaction was incubated at ambient temperature for about 2 h on a nutating mixer. Labeled proteins were then loaded onto a 1 mL HiTrap Heparin HP column. The column was washed with 20 mL of 10 mM sodium phosphate buffer (pH 7.4). Protein was eluted with a 40 mL linear gradient of 0.0-1.5 M NaCl in 10 mM sodium phosphate buffer (pH 7.4). Fractions were collected, and those with the most fluorescence at 501/522 nm were pooled and concentrated. Note that in a SDS-PAGE gel, there was a small molecular weight fluorescent contaminant in the BODIPY-labeled unmodified lysozyme control, but that ≥50% of the labeled product was at the correct molecular weight.

Concentrations of lysozyme and lysozyme conjugates were estimated by UV spectrometry at 280 nm using the extinction coefficient of lysozyme at 281.5 nm (ϵ=26.4 (1% w/v)$^{-1}$ cm$^{-1}$) (Aune, K. C. and Tanford, C. Thermodynamics of the Denaturation of Lysozyme by Guanidine Hydrochloride. I. Dependence on pH at 25° C. Biochemistry 1969, 8, 4579-4585). The concentration of labeled lysozymes were corrected for BODIPY FL absorbance following the manufacturer's protocol (which can be found at http://tools.invitrogen.com/content/sfs/manuals/mp00143.pdf) using the following equation:

$$\text{Absorbance protein}=A_{280\,nm}-A_{504\,nm}*(CF),$$

where CF=correction factor supplied by the manufacturer. The percent labeling was determined by UV spectrometry at 504 nm using the extinction coefficient of BODIPY FL (ϵ=68,000 M$^{-1}$ cm$^{-1}$) as per manufacturer protocol (which can be found at http://tools.invitrogen.com/content/sfs/manuals/mp00143.pdf) using the following equation:

$$\text{Degree of Labeling}=(A_{504\,nm}*mw\,\text{protein})/(\text{protein}\,mg/mL*\epsilon_{BODIPY}),$$

where molecular weight was assumed as 14.3 kDa for all proteins.

These calculation indicated the degree of labeling for the indicated species:
BODIPY FL lysozyme: 36.7%
BODIPY FL PBA-boronated lysozyme: 9.6%
BODIPY FL benzoboroxole-boronated lysozyme: 26.0%

Example 11: Cell Internalization of Boronated Lysozyme

Figure 6:
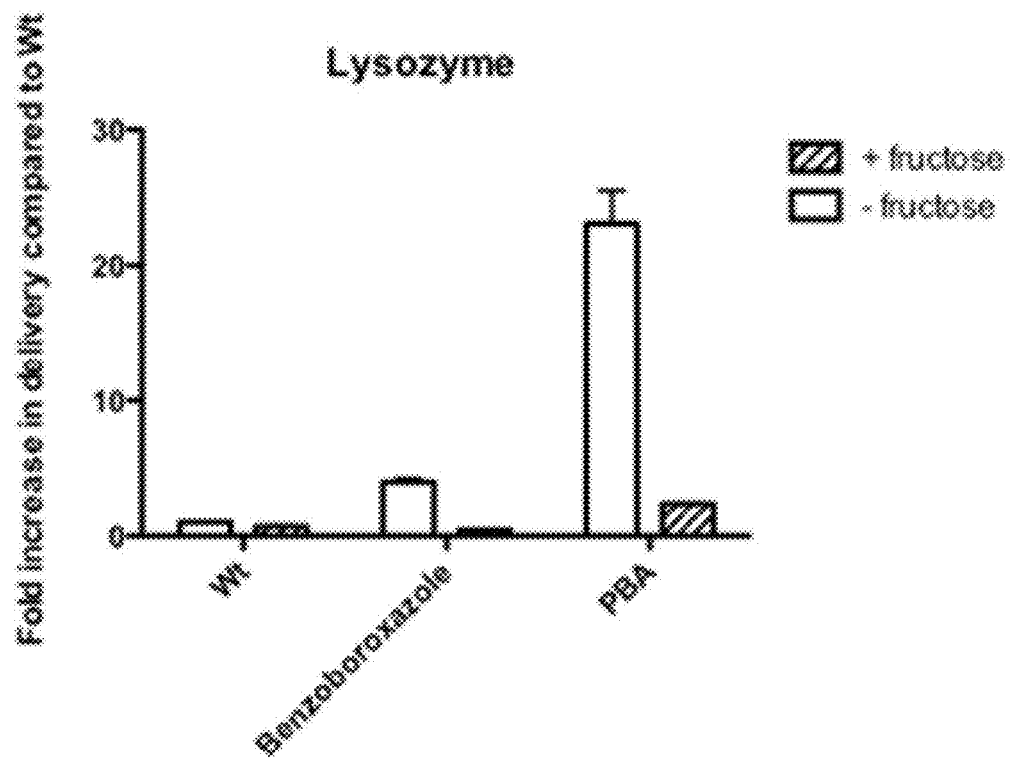
FIG. 6 is a graph of the results of flow cytometry experiments measuring internalization of unmodified lysozyme compared to lysozyme boronated with benzoboroxole into HeLa cells in the presence and absence of fructose. Error bars represent the SD.

As shown in FIG. 6, boronation of lysozyme with benzoboroxole increased its cellular uptake into HeLa cells by about 4-fold. In contrast, boronation of lysozyme with PBA increased its cellular uptake by about 20-fold in HeLa cells. In both cases, this enhancement was decreased by addition of fructose.

Cell Cultures:

Cell lines were obtained from American Type Culture Collection (Manassas, Va.) and were maintained according to the recommended guidelines. Cells were grown in a cell culture incubator at 37° C. and 5% CO2 in flat-bottomed culture flasks. Cell media was supplemented with 10% (v/v) GIBCO fetal bovine serum (FBS), 100 units/mL penicillin, and 100 μg/mL streptomycin in the appropriate cellular media for HeLa cells: DMEM, high glucose (Invitrogen, Carlsbad, Calif.). Cells were counted by hemocytometry for dispensing into 12-well plates (Corning Costar, Lowell, Mass.).

Flow Cytometry Assays

BODIPY-FL was excited with a 488 nm solid-state laser and the emission was collected with a 530/30 bandpass filter. At least 10,000 cellular events were acquired for each sample. Data were analyzed using FlowJo 8.1.3 (Treestar, Ashland, Oreg.).

The day prior to the experiment, 1×105HeLa cells/well were plated in 12 well plates. The day of the experiment, the appropriate amount of fructose was dissolved into the cellular medium to obtain a final 250 mM fructose concentration, then it was sterile filtered with a 0.45 μm Whatman (Piscataway, N.J.) syringe filter. Non-fructose containing medium was likewise sterile filtered to maintain consistency between the experimental groups. Stock solutions of fluorescently labeled proteins were diluted into the cell culture to a final concentration of 5 μM. proteins were incubated with cells for four hours, then the cells were rinsed twice with PBS, removed from the cell culture plate with trypsin, placed in flow cytometry tubes containing 80 μL of FBS (to ensure cell viability), and incubated on ice until analyzed by flow cytometry. Final fluorescence values were divided by the percent fluorophore labeling of the protein to determine the corrected value of fluorescence. Experiments were run in triplicate (except for PBA-boronated lysozyme, which was in duplicate) and the data is reported as the mean±standard deviation normalized to the wild type protein uptake.

Example 12: Boronation of a Biotin-Peptide Conjugate and its Complexation to NeutrAvidin; Cell Internalization of Boronated Avidin A. Preparation of Boronated Biotin-Peptide Conjugate The exemplary Biotin-peptide conjugated used was: Biotin-Anx-GEGEGEGEGEGEG-OH, MW: 1531.54 Da, purchased as a custom synthesis from Biomatik (Cambridge, Ontario, Canada), where Anx stands for ε-aminocaproic acid, G is glycine, and E is glutamic acid.

PBA-boronated biotin-peptide conjugate was prepared similarly to boronated proteins. In 5 mL double deionized water, biotin-peptide (5 mg, 3.3 μmol) was added and the pH of the solution was adjusted to 5.0. Then EDC (80 mg, 0.4 mmol) and 3-aminophenylboronic (2, 29.6 mg, 0.2 mmol) was added. The solution was left to stir overnight on a nutating mixer at ambient temperature. After dialysis, PBA-boronated biotin-peptide was analyzed by MALDI-TOF.

The biotin-peptide control was measured to have 1528.73 Da major peak, the expected peak in anion mode was 1530 Da, therefore, the correction factor was calculated as 1.27 Da. The PBA-boronated biotin-peptide conjugate was measured to have a 2254.20 Da major peak which was corrected to 2255.47 Da. Each PBA conjugation represents 118.9 Da, so on average about 6.1 PBA are conjugated to the biotin-peptide conjugate, noting that 6 glutamates plus the C-terminus are available for conjugation of the phenylboronate.

An analogous method employed 5-amino-2-hydroxymethylphenylboronic acid (1) to prepare benzoboroxole-boronated biotin peptide conjugate. However, the benzoboroxole-boronated biotin peptide crashed out of solution and was insoluble. Addition of high concentrations of fructose to the solution containing the benzoboroxole-boronated biotin peptide solubilized it.

B. Preparation of Boronated-Avidin

The PBA-boronated biotin-peptide can be used to generate boronated Avidin. PBA-boronated biotin-peptide conjugate (having on average 6 PBA) was placed into 8 mL of 100 mM fructose in double deionized $H_2O$ (0.625 mg/mL, 277 μM). Fluorescein-conjugated NeutrAvidin (5.5 mg), was dissolved in 1 mL double deionized $H_2O$ (5.5 mg/mL, 91.7 μM). For a total volume of 1.8148 mL, an aliquot of 0.1818 mL Fluorescein-conjugated NeutrAvidin (9 μM final concentration) was added to an aliquot of 1.633 mL of peptide (249 μM final concentration, 28× fold excess compared to NeutrAvidin). For control NeutrAvidin, for a total volume of 981.8 μL, an aliquot of 181.8 μL NeutrAvidin (17 μM final concentration) was added to an aliquot of 800 μL of 0.2 mg/mL biotin (667 μM final concentration, 39× fold excess compared to NeutrAvidin). Complexations were incubated for 1-2 h at ambient temperature in the dark, then dialyzed overnight in 10 mM fructose in double deionized $H_2O$. Fructose was used throughout to help with solubility of the boronates. Note that NeutrAvidin should be tetrameric, so 4 peptides should complex, giving about 24 boronic acids/NeutrAvidin.

Concentrations of proteins were determined by UV spectrometry at 494 nm using the extinction coefficient of fluorescein ($\epsilon$=68,000 M−1 cm−1) (web site:/tools.invitrogen.com/content/sfs/manuals/mp00143.pdf) and dividing by 2 as ≥2 moles fluorescein were conjugated to 1 mole of NeutrAvidin as per manufacturer protocol (web site:www.piercenet.com/coapdfs/CofA-31006-SPECS.pdf). Avidin control (with biotin only) was 414.8 μM fluorescein; ca. 207.4 μM avidin. Avidin-PBA-boronated biotin-peptide complex was 6.78 μM fluorescein; ca. 3.39 μM avidin. These results indicate that the boronated biotin-protein complex functioned for binding to Avidin.

C. Cell Internalization of Boronated Avidin

Figure 7:
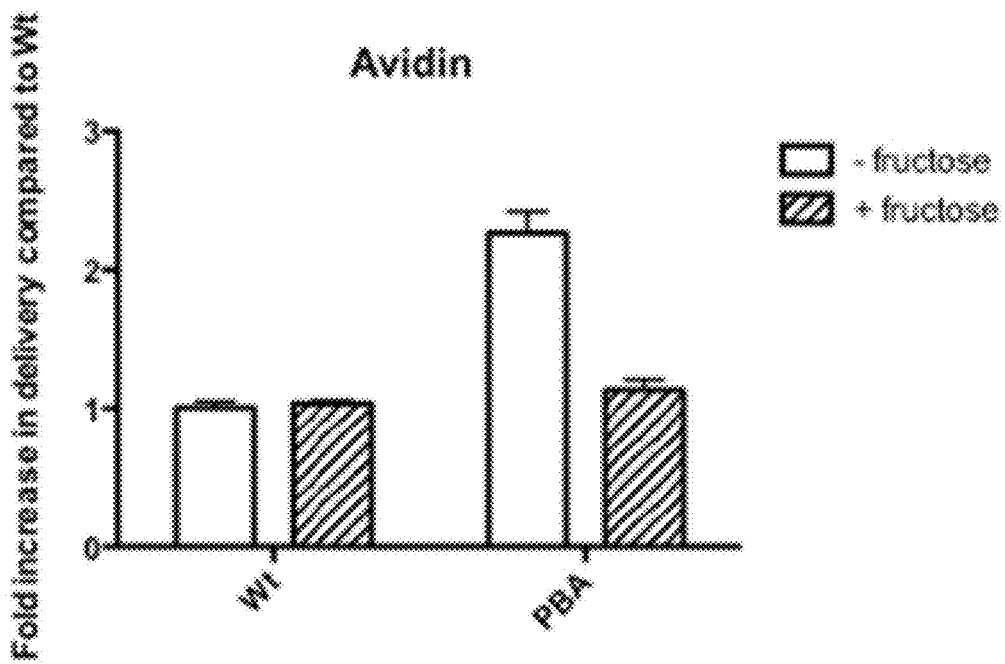
FIG. 7 is a graph of the results of flow cytometry experiments measuring internalization into HeLa cells of unmodified avidin compared to avidin complexed to PBA-boronated biotin peptide in the presence and absence of fructose. Error bars represent the SD.

Flow cytometry experiments were conducted as described in Example 11 with Fluorescein-conjugated NeutrAvidin and Boronated Fluorescein-conjugated NeutrAvidin (boronated by complexation to the PBA-boronated Biotin-peptide conjugate) in HeLa cells. As illustrated in FIG. 7, boronation of Avidin with PBA increased internalization in HeLa cells by about 2-fold.

Example 13: Preparation of Phenylboronated Amino Acids for Synthesis of Boronated Oligopeptides A. Fmoc-protected glutamic acid boronated with 5-amino-2-hydroxymethyl-phenylboronic acid, Fmoc-L-glutamic acid 1-tert-butyl ester (2.66 g, 6.251 mmol),

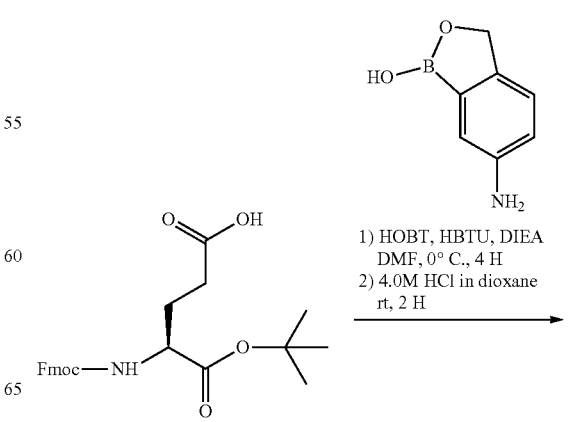

1) HOBT, HBTU, DIEA DMF, 0° C., 4 H
2) 4.0M HCl in dioxane rt, 2 H

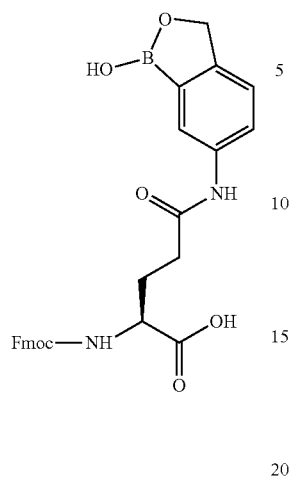

was added to a round bottom flask with 1-Hydroxybenzotriazole (HOBT, 1.914 g, 12.50 mmol) and 2-(1H-benzotriazol-1-yl)-1,1,3,3-tetramethyluronium hexafluorophosphate (HBTU, 3.557 g, 9.377 mmol). The flask was placed under argon and dry DMF was added (62 mL). N,N-diisopropylethylamine (DIEA, 5.88 mL, 33.78 mmol) was then added at 0° C. and the reaction was allowed to stir for 10 minutes. Under argon, 5-amino-2-hydroxymethyl-phenylboronic acid (2.318 g, 12.0 mmol) was combined with dry DMF (5 mL) and N,N-diisopropylethylamine (5 mL, 28.72 mmol). The solution of amine was added dropwise to the reaction mixture over an hour. Upon complete addition, the round bottom flask was removed from the ice bath and stirred at room temperature for 4 h. The DMF was then removed by vacuum. The product was diluted in 200 mL 1M HCl and extracted with ether (10×200 mL). The organics were concentrated, loaded with celite, and purified with silica gel chromatography (4% methanol, 96% dichloromethane) to yield product (533 mg, 14%). $^1$H-NMR (400 MHz; CDCl$_3$) δ=7.94 (s, 1H), 7.73 (d, J=7.5 Hz, 3H), 7.55 (t, J=8.9 Hz, 2H), 7.37 (t, J=7.4 Hz, 2H), 7.29-7.26 (m, 2H), 7.22 (d, J=8.3 Hz, 1H), 5.83 (d, J=7.9 Hz, 1H), 4.99 (s, 2H), 4.39 (t, J=6.7 Hz, 2H), 4.29 (m, 1H), 4.13 (t, J=6.8 Hz, 1H), 2.42 (m, 2H), 2.30 (m, 1H), 1.99 (m, 1H), 1.45 (s, 9H). $^{13}$C NMR (100 MHz; CDCl$_3$): δ 176.3, 171.2, 170.9, 157.1, 149.5, 143.81, 143.70, 141.4, 137.4, 127.9, 127.2, 125.26, 125.12, 123.3, 121.63, 121.54, 120.1, 83.1, 77.2, 71.1, 67.3, 54.0, 47.3, 34.1, 30.1, 28.1.

The t-butyl ester protected product was added to a round bottom flask and 4.0M HCl in dioxane (10 mL, 40 mmol) was added under argon to remove the t-butyl group. The mixture was allowed to stir for 2 hours at rt. The solution was concentrated under reduced pressure and purified by flash chromatography (silica gel, 1:99-10:90, methanol/dichloromethane). $^1$H-NMR (400 MHz; MeOH) δ=7.78 (m, 7.2 Hz, 3H), 7.65 (m, 3H), 7.36 (quintet, J=7.4 Hz, 2H), 7.28 (m, 3H), 4.97 (s, 2H), 4.35-4.27 (m, 2H), 4.22 (dd, J=12.5, 6.4 Hz, 1H), 4.12 (t, J=6.7 Hz, 1H), 2.50-2.40 (m, 2H), 2.28 (td, J=12.3, 5.7 Hz, 1H), 2.07 (dt, J=15.1, 7.5 Hz, 1H). HRMS (ESI$^-$) m/z calculated for (C$_{27}$H$_{24}$BN$_2$O$_7$)$^-$ 498.1708, measured 498.1729. overall yield: 256 mg

B. Fmoc-Protected Glutamic Acid Boronated with 5-Aminophenylboronic Acid

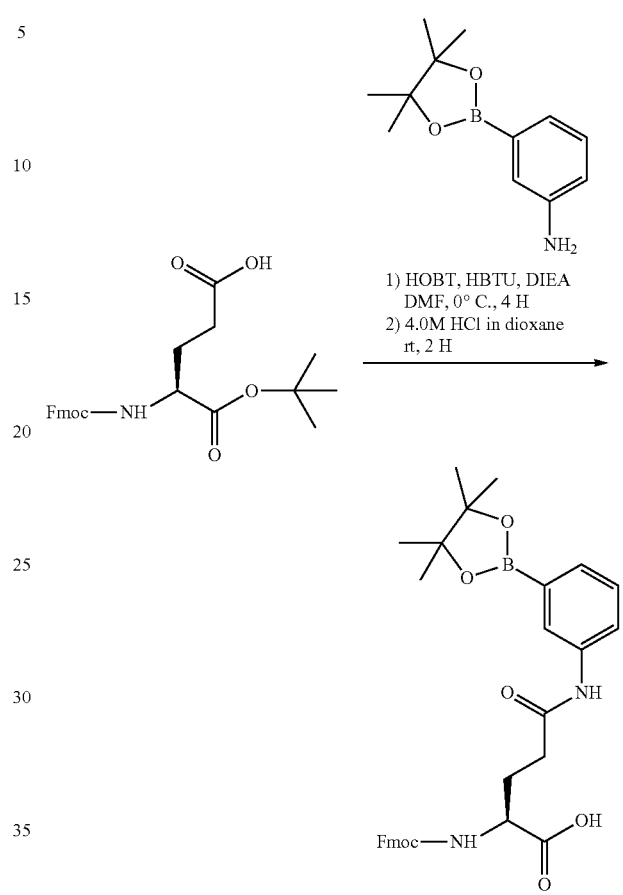

Fmoc-L-glutamic acid 1-tert-butyl ester (2.61 g, 6.128 mmol) was added to a round bottom flask with HOBt (1.876 g, 12.26 mmol) and HBTU (3.486 g, 9.19 mmol). The flask was placed under argon and dry DMF added (61 mL). N,N-diisopropylethylamine (5.67 mL, 32.56 mmol, 0.742 g/mL) was added at 0° C. and the reaction was allowed to stir for 10 minutes. Under argon, 3-aminophenylboronic acid pinacol ester (2.685 g, 12.26 mmol) was combined with dry DMF (5 mL) and N,N-diisopropylethylamine (5 mL, 28.72 mmol, 0.742 g/mL). The solution of amine was added dropwise over an hour. Upon complete addition, the round bottom was removed from the ice bath and allowed to stir at rt for 4 h. The DMF was removed by vacuum. The product was diluted in 200 mL 1M HCl and extracted with ether (3×200 mL). The organics were concentrated, loaded with celite, and purified with silica gel chromatography (40% ethyl acetate, 60% hexanes) to yield product 2.929 g, 80.4%). $^1$H NMR (400 MHz; CDCl3): δ=8.08 (s, 1H), 7.86-7.81 (m, 2H), 7.76 (d, J=7.5, 2H), 7.59 (t, J=8.2, 2H), 7.53 (d, J=7.2, 1H), 7.39 (t, J=7.4, 2H), 7.31 (dt, J=7.1, 3.3, 2H), 5.61 (d, J=7.7, 1H), 4.42 (t, J=6.6, 2H), 4.29 (t, J=6.8, 1H), 4.20 (t, J=6.9, 1H), 2.39 (t, J=6.2, 2H), 2.31 (s, 1H), 1.96 (s, 1H), 1.31 (s, 12H), 1.24 (s, 9H). $^{13}$C NMR (100 MHz; CDCl$_3$) δ=175.1, 171.1, 170.5, 156.9, 143.94, 143.79, 141.5, 137.7, 130.7, 128.6, 127.9, 127.2, 125.9, 125.29, 125.20, 123.1, 120.1, 84.0, 83.0, 75.2, 67.3, 47.3, 34.0, 30.0, 28.1, 25.0.

The t-butyl ester protected product was added to a round bottom flask and 4.0M HCl in dioxane (10 mL, 40 mmol)

was added under argon. The mixture was allowed to stir for 2 hours at rt. The solution was concentrated under reduced pressure and purified by flash chromatography (silica gel, 1:99-10:90, methanol/dichloromethane). $^1$H-NMR (400 MHz; CDCl$_3$) δ=7.93 (s, 1H), 7.77 (m, 4H), 7.57 (d, J=6.4 Hz, 3H), 7.35 (m, 7.7 Hz, 4H), 6.04 (d, J=6.9 Hz, 1H), 4.38 (d, J=6.5 Hz, 2H), 4.18 (t, J=6.7 Hz, 1H), 2.65-2.59 (br m, 1H), 2.57-2.51 (br m, 1H), 2.36-2.28 (br m, 1H), 2.14-2.06 (br m, 1H), 1.32 (s, 12H). (KJ-2-104-2). Overall yield: 1.124 g; M–H, Expected: 568.2490, observed: 568.2498.

C. Fmoc-Protected Phenylalanine Boronated with Phenylboronic Acid.

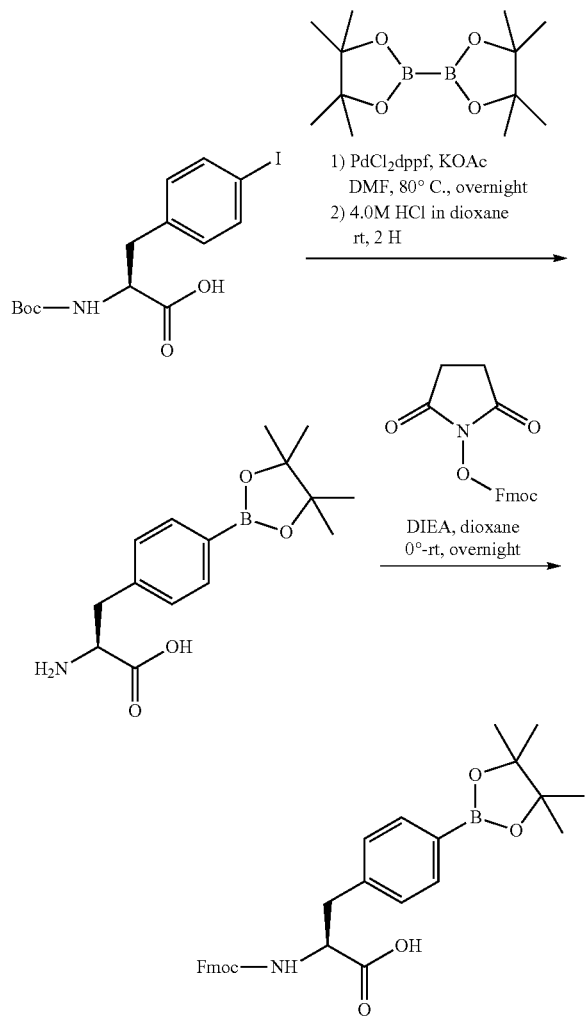

Boc-4-iodo-L-phenylalanine (10 g, 25.56 mmol), bis(pinacolato)diboron (9.737 g, 38.34 mmol), KOAc (12.543 g, 127.8 mmol), PdCl$_2$(dppf) (1.744 g, 2.38 mmol) were added to a round bottom flask. The flask was placed under argon and dry, degassed DMF added (250 mL). The reaction was heated to 80° C. overnight. The reaction was cooled and filtered through a celite plug and washed with EtOAc. The filtrate was concentrated under reduced pressure and purified by flash chromatography (40% EtOAc/Hexanes, then 100% EtOAc with 1% acetic acid) to yield the crude product (7.4 g). $^1$H NMR (400 MHz; CDCl3) δ=7.76 (d, J=7.9, 2H), 7.20 (d, J=7.6, 2H), 4.90 (d, J=6.7, 1H), 4.59 (d, J=7.4, 1H), 3.22 (dd, J=14.4, 4.8, 1H), 3.11 (dd, J=15.0, 7.1, 1H), 1.42 (s, 9H), 1.34 (s, 12H).

Boc-4-pinicalborane-L-phenylalanine (3.7 g, 9.456 mmol) was added to a round bottom flask with 4.0 M HCl in dioxane (40 ml, 160 mmol HCl) and stirred at room temperature overnight to remove the Boc protecting group. The reaction was purged with Ar gas for thirty minutes to remove the HCl gas and concentrated under reduced pressure. $^1$H NMR (400 MHz; MeOH) δ=7.76 (d, J=8.0, 2H), 7.32 (d, J=7.9, 2H), 4.27 (dd, J=7.9, 5.6, 1H), 3.36 (d, J=5.3, 1H), 3.16 (dd, J=14.6, 8.1, 1H), 1.35 (s, 12H). 4-Pinicolborane-L-phenylalanine (4.554 g, 13.80 mmol), N,N-diisopropylethylamine (9.62 mL, 55.21 mmol), and Fmoc N-hydroxysuccinimide ester (5.133 g, 15.18 mmol) was added to a round bottom flask. The reaction was put under Ar and anhydrous dioxane (130 mL) was added. The reaction was stirred at room temp overnight, concentrated under reduced pressure, and purified by silica flash chromatography (1% MeOH/DCM, then 20% MeOH/DCM v/v). $^1$H-NMR (400 MHz; CDCl$_3$) δ=7.76 (d, J=7.4 Hz, 4H), 7.54 (t, J=7.4 Hz, 2H), 7.40 (t, J=7.5 Hz, 2H), 7.30 (m, 2H), 7.18 (d, J=7.3 Hz, 2H), 5.20 (d, J=7.8 Hz, 1H), 4.71 (q, J=6.3 Hz, 1H), 4.42 (m, 1H), 4.34 (t, J=8.9 Hz, 1H), 4.20 (t, J=7.2 Hz, 1H), 3.24 (dd, J=13.8, 5.2 Hz, 1H), 3.14 (dd, J=14.2, 5.7 Hz, 1H), 1.34 (s, 12H). $^{13}$C NMR (126 MHz; CDCl3): δ=174.9, 155.9, 143.90, 143.77, 141.4, 138.9, 135.3, 128.9, 127.9, 127.2, 125.26, 125.21, 120.1, 84.1, 77.2, 67.3, 54.5, 47.2, 38.0, 25.0. Total yield=8.238 g, 16.0 mmoles, 62.6% overall yield.

Fmoc-protected boronated amino acids as described herein are employed to prepare boronated peptides for boronation of peptides and proteins. For example, Fmoc-protected boronated glutamic acid is used in place of Fmoc-protected glutamic acid in conventional Fmoc solid phase peptide synthesis to prepare boronated oligopeptides containing one or more boronated glutamic acids, such as Anx-GE$_B$GE$_B$GE$_B$GE$_B$GE$_B$GE$_B$G, where E$_B$ represent boronated glutamic acid. Similarly, Fmoc-protected boronated phenylalanine can be used to prepare boronated oliogpeptides containing one or more boronated phenylalanines. Conventional Fmoc solid phase described in Chan, W. C. and White P. D. Fmoc Solid Phase Peptide Synthesis—A Practical Approach, Oxford University Press 2000. This reference is incorporated by reference herein in its entirety for its description of methods and materials for solid phase peptide synthesis.

Example 14: Bioreversible Boronation of Proteins; Boronation Reagent 100 for Traceless Delivery of Proteins into Cells An exemplary boronation reagent (100) combines 2-hydroxymethylphenylboronic acid (benzoxaborole) with an immolative linker for delivery of native proteins into the cytosol of a cell. An immolative linker is used for linking the phenylboronate group to the cargo molecule, e.g., a protein, and which can be removed, for example, by enzyme action, to release the native cargo molecule, thus the linker is traceless (does not leave behind any atom or moiety that is not found in the native cargo molecule). Immolative or traceless linkers are of particular benefit in delivery of peptides or protein into cells in their native form. The exemplary reagent 100 used a o-hydroxydihydrocinnamic acid derivative, known as the trimethyl lock (TML), as the linker between benzoxaborole and a protein cargo. After being triggered, the TML exhibits extremely high lactonization rates to release a cargo of interest. The TML is a specific example of a trialkyl lock system, as is known in the art. Reagent 100 (also designated TMLB-NHS) carries an N-hydroxysuccinimide ester for chemoselective conjugation to amino groups, such as those at the N terminus and on the side chains of lysine residues, which have a ~6% abundance in proteins. The attachment of benzoxaborole to an immolative linker via an ester linkage allows the boronic acid moiety to be removable in the presence of endosomal esterases, to afford the delivery of completely native protein. It will be appreciated that various other reactive groups can be employed in place of the N-hydroxysuccinimide ester e.g., other amine reactive groups or chemoselective reactive groups which react selectively with groups present in the cargo molecule.

Figure 27:
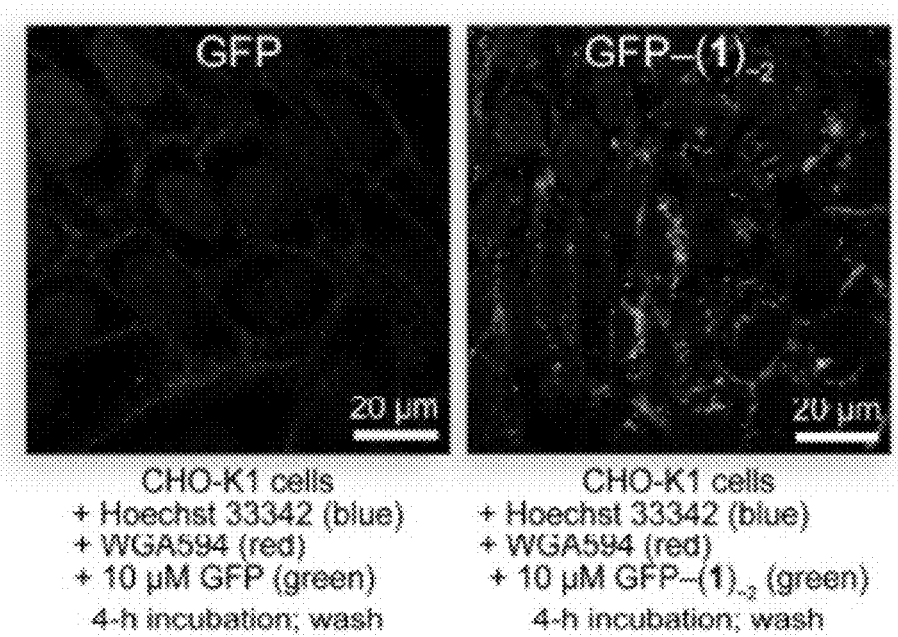
FIG. 27 illustrates cellular uptake of boronated GFP (Green Fluorescent Protein) as in Example 14. GFP labelled with only about 2 molecules of phenylboronate was taken up readily by CHO-K1 cells (right) compared to unboronated GFP (left).

The ability of reagent 100 to enhance the cellular internalization of a model protein: green fluorescent protein (GFP) was assessed. GFP was chosen due to its distinctive fluorescent read-out and the inability of native GFP to enter mammalian cells. Overnight incubation at ambient temperature GFP with 100-fold excess of reagent 100 in 3:1 PBS/acetonitrile yielded 3±1 labels per protein molecule. The labeling (boronation) was reversible, as co-incubation of TMLB-GFP with a lysate from CHO K1 cells removed all of the labels. The uptake of TMLB-GFP and unlabeled GFP by CHO K1 cells was compared FIG. 27. After a 4-h incubation, a dramatic increase in the cellular uptake of TMLB-GFP was observed. The fluorescence in microscopy images was largely punctate, indicating that TMLB-GFP was taken up into cells by an endosomal pathway. Co-localization of this bright punctate staining with a stain for transferrin was consistent with this conclusion. After a 24-h incubation, some cytosolic staining was observed (data not shown), indicating endosomal escape.

To confirm that the boronate moiety was responsible for the difference in cellular entry, additional experiments were performed. A non-boronated reagent (TMOAC-NHS ester) that lacks the benzoxaborole functionality to modify GFP, yielding a level of labeling similar to that from TMLB-NHS ester.

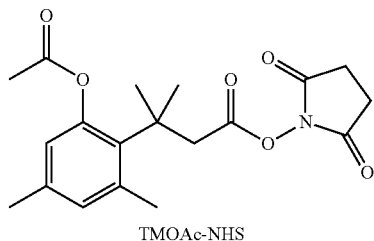 [SMILES: CC(=O)Oc1cc(C)cc(C)c1C(C)(C)CC(=O)ON1C(=O)CCC1=O]

TMOAc-NHS

When incubated with cells for 4 h, TMLOAc-GFP was taken up comparably to unlabeled GFP rather than TMLB-GFP. These results indicate that the effects are not due to modification of the lysine residues themselves, or to the TML portion of TMLB.

The importance of the boronic acid motif for uptake was assessed by repeating the cellular uptake experiments using TMLB-GFP in the presence of fructose, which has a Ka of 336 M−1 for benzoxaborole.34 In the presence of fructose as a competitor, a significant decrease in GFP uptake was observed by both confocal microscopy and flow cytometry. Taken together, these results indicate that the boronic acid portion of TMLB-GFP is responsible for enhanced cellular uptake.

The efficacy of reagent 100 as a delivery vehicle for another protein, a cytotoxic ribonuclease was also assessed. This enzyme, which is the G88R variant of ribonuclease A, must reach cytosolic RNA to elicit its cytotoxic activity. After labeling the ribonuclease by the same procedure used to label GFP, an average of 1.6±0.7 labels per molecule of protein was observed. This lower level of labeling is consistent with GFP (20) having more amino groups than does the ribonuclease (13). The labeling was reversible, as incubation with a CHO K1 cell lysate removed all of the labels. The the ability of TMLB-ribonuclease and unlabeled ribonuclease to inhibit the proliferation of K-562 cells, which are from a human leukemia line was assessed. The boronate modifications resulted in a decrease in $IC_{50}$ (FIG. 28), indicating that the boronate enables more ribonuclease to reach the cytosol.

Figure 29:
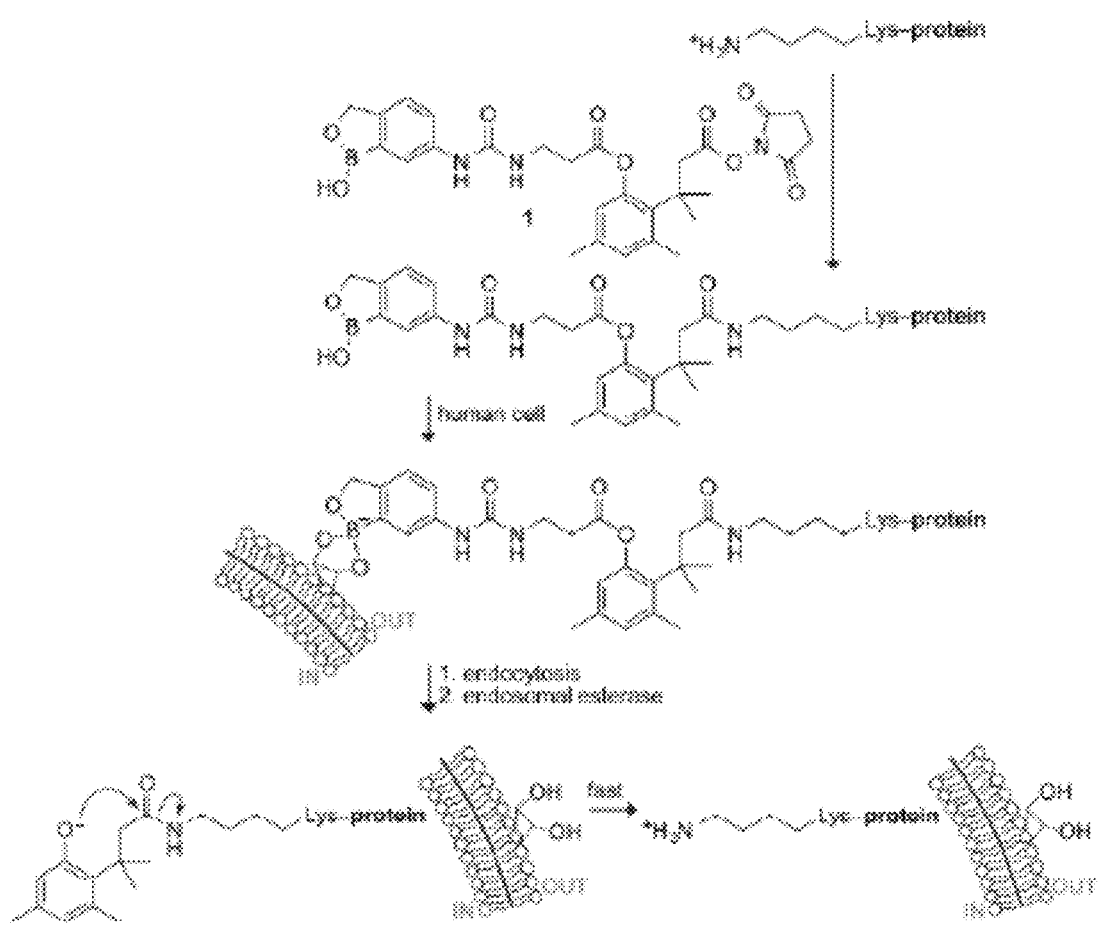
FIG. 29 illustrates bioreversible protein uptake employing the boronation reagent 100.

FIG. 29 illustrates a possible mechanism of bioreversible modification of a protein using reagent 100.

The immolative boronate-based reagent 100 increases the cellular delivery of proteins, as measured by fluorescence microscopy, flow cytometry, or a cytotoxic phenotype based on ribonucleolytic activity. The delivery of protein is traceless, as cellular esterase activity returns the proteins to an unmodified state.

Cell Culture.

Cell lines were obtained from American Type Culture Collection (Manassas, Va.) and were maintained according to the recommended procedures. Medium and added components were the Gibco® brand from Thermo Fisher Scientific (Waltham, Mass.). Cells were grown in flat-bottomed culture flasks in a cell-culture incubator at 37° C. under $CO_2$ (g) (5% v/v). Chinese hamster ovary (CHO K1) cells were grown in F12K nutrient medium and K562 cells were grown in RPMI 1640 medium, both supplemented with fetal bovine serum (FBS) (10% v/v), penicillin (100 units/mL), and streptomycin (100 μg/mL). Cells were counted with a hemocytometer to determine the seeding density in 12-well plates from Corning Costar (Lowell, Mass.) or microscopy dishes from Ibidi (Madison, Wis.). All flow cytometry and confocal microscopy was performed with live cells, incubated on ice at the time of analysis.

Labeling of GFP

Preparation of Green Fluorescent Protein (GFP)

The gene encoding the eGFP variant GFP was inserted into the pET22b vector (Novagen), along with an N-terminal $His_6$ tag followed by a spacer region and a TEV protease recognition sequence. The GFP gene was modified with the following 17 substitutions to generate a "superfolding" variant that folds readily when produced in Escherichia coli: F64L, S65T, F99S, M153T, V163A, S30R, Y145F, I171V, A106V, Y39I, N105K, E111V, I128T, K166T, I167V, S205T, L221H, F223Y, T225N. [52a-e] The vector also contained a T7 promoter and ampicillin resistance gene.

The expression vector was transformed into electrocompetent BL21(DE3) E. coli cells from New England Biolabs (Ipswich, Mass.), then plated on LB agar containing ampicillin (200 μg/mL). On the following day, a single colony was used to inoculate 50 mL of LB medium, and the resulting culture was grown overnight at 37° C. in a shaking incubator. On the following day, 10 mL of starter culture was used to inoculate 1.00 L of Terrific Broth medium from Research Products International (Mt. Prospect, Ill.) in a 3.8-L glass flask with ampicillin at a final concentration of 200 μg/mL. Flasks were shaken at 200 rpm at 37° C. in a shaking incubator until cells reached log phase (OD 0.6-0.8 at 600 nm). The production of GFP was induced by adding IPTG to a final concentration of 1 mM, and cells were grown overnight at 37° C. in a shaking incubator.

Cells were harvested by centrifugation for 20 min at 5,000 rpm at 4° C. Cell pellets, which were bright yellow in color, were collected and resuspended in 15 mL of lysis buffer per 2 L of liquid growth, which was 50 mM Tris-HCl buffer, pH 7.0, containing NaCl (100 mM) and imidazole (30 mM). Cell pellets were vortexed and stored frozen at −20° C. overnight.

Cells were lysed with a TS Series cell disrupter from Constant Systems (Kennesaw, Ga.), and the lysate was subjected to centrifugation immediately for 1 h at 11,000 rpm at 4° C. The supernatant was filtered through 5-μM syringe filters from EMD Millipore (Billerica, Mass.) and solid, pelleted material was discarded. Filtered cell lysates were purified by chromatography on Ni-NTA resin from GE Healthcare (Little Chalfont, UK) and eluted using a linear gradient of imidazole. The binding and wash buffer was 30 mM sodium phosphate buffer, pH 7.4, containing NaCl (0.50 M) and imidazole (20 mM). The elution buffer was 30 mM sodium phosphate buffer, pH 7.4, containing NaCl (0.50 M) and imidazole (0.50 M). Eluted fractions were collected, pooled, and dialyzed against 4 L of 20 mM Tris-HCl buffer, pH 7.0, containing EDTA (1 mM).

The dialyzed solution was purified again using anion-exchange chromatography on a hiTrap Q column from GE Healthcare. The protein was eluted by using a linear gradient of NaCl (0-1.00 M) in 20 mM Tris-HCl buffer, pH 7.0, containing EDTA (1.0 mM). Upon elution, colored fractions were pooled and concentrated (if necessary). The overall yield of GFP was ~120 mg per L of culture.

Labeling of GFP with TMLB-NHS Ester:

TMLB-NHS ester (2.2 mg, 4 μmol, 100 equiv) was added to a 150-μL solution of GFP (300 μM, 0.04 μmol) in PBS. The vial was placed on a nutator in foil overnight at room temperature. The solution was transferred to 10,000 MWCO dialysis tubing and dialyzed twice against 4 L of PBS for 4 h at 4° C. The extent of labeling was characterized by MALDI-TOF mass spectrometry. To determine the extent of labeling, the average mass of labeled protein was taken as a weighted average for all events within the defined peak range on the background-corrected MALDI-TOF spectra. The molecular weight of non-labeled protein was then subtracted from the given value to give the average total mass of all labels. This value was then divided by the molecular weight of the modifying small molecule minus the mass of N-hydroxysuccinimide (565.38 Da−115.09 Da=450.29 Da), which was lost during conjugation, to give the average number of labels per molecule of protein. On average there were approximately 3±1 labels per GFP. The labeled protein is referred to as TMLB-GFP. An identical procedure was used with non-boronated TML (TMLOAc) commercially available from sigma Aldrich (Milwaukee, Wis.) in which the phenolic oxygen is protected as acetate. The TMLOAc-GFP was also decorated with 3±1 labels.

Hydrolysis of Labeled GFP by CHO K1 Cell Lysate:

CHO K1 cells were grown to confluence in a 10-cm$^2$ dish before their collection and lysis with M-PER (Thermo Fisher Scientific). The presence of esterase activity in the lysate was verified by a colorimetric assay using p-nitrophenyl acetate (data not shown). A solution of TMLB-GFP (10 μg) was added to 200 μL of CHO K1 cell lysate, and the reaction mixture was nutated at ambient temperature for 12 h. The GFP was subsequently purified with HisPur™ Ni-NTA Magnetic Beads (Thermo Fisher Scientific). The regeneration of unlabeled GFP was confirmed with MALDI-TOF mass spectrometry.

TMLB-GFP Internalization

Flow Cytometry.

CHO K1 cells were seeded at a density of 50,000 cells/ well in 12-well plates. Cells were incubated with GFP (10 μM), TMLB-GFP (10 μM), or TMLOAc-GFP (10 mM) for 4 h. Cells were then rinsed twice with Dulbecco's PBS (DPBS) from Thermo Fisher Scientific and released from the plate with 250 μL of trypsin/EDTA (0.25% w/v). Cells were resuspended in an additional 500 μL of medium and incubated on ice until analyzed by flow cytometry. The fluorescence intensity of at least 20,000 events was measured by flow cytometry. Alexa Fluor488® was excited with a 488-nm solid-state laser, and the emission was measured through a 530/30 bandpass filter.

Microscopy.

CHO K1 cells were seeded at a density of 50,000 cells/ dish in 35-mm μ-dish microscopy imaging dishes from Ibidi. Cells were incubated with GFP (10 μM), TMLB-GFP (10 μM), or TMLOAc-GFP (10 μM) for 4 h. Cells were then rinsed twice with DPBS and cell nuclei were stained with Hoechst 33342 (2 μg/mL) for 5 min at 37° C. and cell membrane was stained with WGA-594 (5.0 μg/mL) (Invitrogen) for 15 min on ice. Cells were then washed twice with wash buffer, and examined live using a scanning confocal microscope.

Colocalization with Organelles

Microscopy.

CHO K1 cells were seeded at a density of 50,000 cells/ dish in 35-mm μ-dish microscopy imaging dishes from Ibidi. Cells were incubated with 10 μM TMLB-GFP for 4 h, then rinsed twice with DPBS, and cell nuclei were stained with Hoechst 33342 (2 μg/mL) for 5 min at 37° C. and cell membranes were stained with either WGA-594 (5.0 μg/mL) for 15 min on ice, CellTracker™ Orange CMTMR dye (1 μM) at 37° C. for 15 min, Transferrin-594 (25 μg/mL) at 37° C. for 15 min or LysoTracker Red (50 nM) at 37° C. for 30 min (all from Invitrogen). Cells were then washed twice with wash buffer, and examined live using a scanning confocal microscope.

Internalization Over Time

Microscopy.

CHO K1 cells were seeded at a density of 50,000 cells/ dish in an 8-well μ-slide microscopy imaging dish from Ibidi. Cells were incubated with GFP (10 μM) or TMLB-GFP (10 μM) for 4 or 24 h. Cells were then rinsed twice with DPBS, and cell nuclei were stained with Hoechst 33342 (2 μg/mL) for 5 min at 37° C., and cell membranes were stained with WGA-594 (5.0 μg/mL) for 15 min on ice. Cells were then washed twice with wash buffer, and examined live using a scanning confocal microscope.

Fructose Competition:

10 μM TMLB-GFP was preincubated in an aqueous solution of fructose (175 mM) for 30 min, then used to treat CHO K1 cells for 4 h before analysis by either confocal microscopy or flow cytometry as described above.

Ribonuclease A Protein Labeling

Preparation of FLAG-Ribonuclease A (RNase A) and G88R RNase A:

FLAG-RNase A and G88R RNase A were produced and purified by methods described previously. [51, 53]

Labeling of FLAG-RNase A and G88R RNase A:

The labeling of FLAG-RNase A and G88R RNase A with TMLB-NHS ester, and characterization of the extent of labeling was carried out as described for GFP. On average, there were 1.6±0.7 labels per FLAG-RNase A, and 2±1 labels per G88R RNase A.

Hydrolysis of Labeled FLAG-RNase A by K562 Cell Lysate:

K-562 cells were grown to confluence in a T75 flask before their collection and lysis with M-PER from Thermo Fisher Scientific. The presence of esterase activity in the lysate was verified by a colorimetric assay using p-nitrophenyl acetate (data not shown). A solution of esterified FLAG-RNase A (10 µg) was added to 200 µL of K-562 cell lysate, and the reaction mixture was nutated at ambient temperature for 12 h. FLAG-RNase A was purified with anti-FLAG® M2 Magnetic Beads from Sigma-Aldrich. The regeneration of unlabeled FLAG-RNase A was confirmed with MALDI-TOF mass spectrometry.

Figure 28:
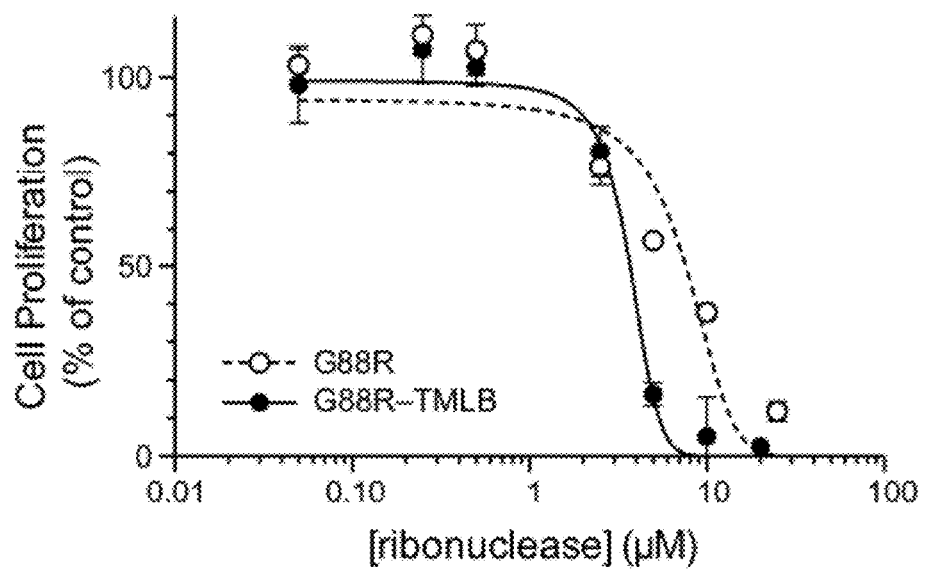
FIG. 28 is a graph showing inhibition of K-562 cell proliferation by a TMLB-labeled ribonuclease and the unmodified ribonuclease. G88R RNase A, $IC_{50}$=(6.4±0.1) µM; TMLB-labeled G88R RNase A, $IC_{50}$=(3.5±0.8) µM). Each data point represents the mean±SE for three separate experiments, each performed in duplicate.

Cell-Proliferation Assays:

The effect of unmodified G88R RNase A and TMLB-G88R RNase A on the proliferation of K-562 cells was assayed using a CyQUANT® NF Cell Proliferation Assay Kit (Invitrogen). Briefly, $5 \times 10^4$ cells/mL were added to each well of a 96-well plate in 100 µL of serum-free RPMI 1640 medium. Cells were incubated with G88R RNase A or TMLB-G88R RNase A for 48 h, with PBS and $H_2O_2$ serving as negative and positive controls, respectively. Cells were then washed and incubated in CyQUANT® reagent for 30 min and fluorescence intensity was measured with excitation at ~485 nm and emission detection at ~530 nm. Data are the average of two measurements for each concentration, and the entire experiment was repeated in triplicate. The results are shown as the percentage of dye incorporated relative to control cells treated with PBS. Values for $IC_{50}$ were calculated by fitting the curves by nonlinear regression to the equation:

$$y=100\%/(1+10^{(log(IC50)-log\ [ribonuclease])h})$$

where y is the total DNA synthesis following the CyQUANT dye pulse and h is the slope of the curve (FIG. 28).

Example 15: Synthesis of Boronation Reagent 100

The boronation reagent 100 was synthesized by the scheme illustrated in FIG. 24.

General:

All chemicals were from Sigma-Aldrich (Milwaukee, Wis.) and were used without further purification. All glassware was flame-dried, and all reactions were performed under an atmosphere of $N_2$ (g). Reagent grade solvents, i.e., dichloromethane (DCM), tetrahydrofuran (THF), triethylamine (TEA), and dimethylformamide (DMF), were dried over a column of alumina and were accessed under an atmosphere of $N_2$ (g). The removal of solvents "under reduced pressure" refers to the use of a rotary evaporator with water-aspirator pressure (<20 torr) and a water bath of <40° C. Column chromatography was performed with Silicycle 40-63 Å silica (230-400 mesh); thin-layer chromatography (TLC) was performed with EMD 250-µm silica gel 60-F254 plates. PBS contained $Na_2HPO_4$ (10 mM), $KH_2PO_4$ (1.8 mM), NaCl (137 mM), and KCl (2.7 mM) at pH 7.3. All procedures were performed at room temperature (~22° C.) unless noted otherwise.

$^1H$ and $^{13}C$ NMR spectra were acquired at ambient temperature with a Bruker Avance III 500i spectrometer at the National Magnetic Resonance Facility at Madison (NMRFAM) and referenced to residual protic solvent. Electrospray ionization (ESI) mass spectrometry of small molecules was performed with a Micromass LCT in the Mass Spectrometry Facility in the Department of Chemistry at the University of Wisconsin-Madison. Matrix-assisted laser desorption ionization-time-of-flight (MALDI-TOF) mass spectrometry of proteins was performed with a Voyager DE-Pro instrument at the Biophysics Instrumentation Facility at the University of Wisconsin-Madison. Absorbance measurements were made with an infinite M1000 plate reader from Tecan (Männedorf, Switzerland). Confocal microscopy was performed with an Eclipse TE2000-U laser scanning confocal microscope from Nikon (Tokyo, Japan), equipped with an AxioCam digital camera from Zeiss (Jena, Germany). Flow cytometry was performed at the University of Wisconsin-Madison Carbone Cancer Center Flow Cytometry Facility with a FACS Calibur instrument from BD Biosciences (San Jose, Calif.). Cytometry data were analyzed by using the program FlowJo 8.7 from Treestar (Ashland, Oreg.). Calculations were performed with Prism version 6 software from Graph Pad Software (La Jolla, Calif.).

Synthesis (FIG. 24):

Step 1.

2,5-Dimethylphenol (5.0 g, 40.9 mmol) was dissolved in methanesulfonic acid (10 mL). Methyl-3,3-dimethylacrylate (5.61 g, 49.1 mmol) was added, and the resulting solution was heated to 70° C. for 24 h. The reaction mixture was then allowed to cool to room temperature and poured into separating funnel with 250 ml of water. The mixture was then extracted with ethyl acetate (3×100 mL). The organic layer was washed with saturated aqueous $NaHCO_3$ followed by brine. The organic layers were combined and dried over $NaSO_4$ (s). The solvent was removed under reduced pressure and the crude product was purified by chromatography on a column of silica gel (2:8 EtOAc/hexanes) to afford the indicated product as an off-white solid (7.6 g, 92%).

$^1H$ NMR (500 MHz, $CDCl_3$, δ): 1.45 (s, 6H), 2.27 (s, 3H), 2.46 (s, 3H), 2.60 (s, 2H), 6.83 (d, J=6.86 Hz, 1H), 6.99 (d, J=6.85 Hz, 1H); $^{13}C$ NMR (125 MHz, $CDCl_3$, δ): 16.28, 23.10, 27.63, 35.35, 45.61, 124.56, 127.98, 129.10, 129.49, 133.54, 149.75, 168.43; HRMS (ESI) calculated for $[C_{13}H_{16}O_2]^+$ $(M+NH_4)^+$ requires m/z 222.1489; found m/z 222.1486.

Step 2.

The product of step 1 (3.5 g, 17.1 mmol) was dissolved in anhydrous THF (20 mL). The resulting solution was added dropwise to a suspension of $LiAlH_4$ (0.971 g, 25.6 mmol) in anhydrous THF (170 mL) that had been cooled to 0° C. The reaction mixture was allowed to warm to room temperature and stirred overnight. The reaction was quenched by the slow addition of ethyl acetate (20 mL) followed by the slow addition of water (20 mL). The mixture was filtered to remove the aluminum salts, and the filtrate was dried over $NaSO_4$ (s). The solvent was removed under reduced pressure, and the crude product was purified by chromatography on a column of silica gel (4:6 EtOAc/hexanes) to afford the indicated product as a colorless oil (2.8 g, 80%).

$^1H$ NMR (500 MHz, $CDCl_3$, δ): 1.45 (s, 6H), 2.18 (s, 3H), 2.22 (t, J=7.12 Hz, 2H), 2.48 (s, 3H), 3.59 (t, J=7.11 Hz, 2H), 5.31 (s, 1H), 6.59 (d, J=7.60 Hz, 1H), 6.86 (d, J=7.58 Hz, 1H); $^{13}C$ NMR (125 MHz, $CDCl_3$, δ): 16.24, 25.69, 32.06, 39.90, 44.93, 61.36, 121.82, 125.57, 127.98, 131.55, 135.88, 153.54; HRMS (ESI) calculated for $[C_{13}H_{20}O_2]^+$ $(M^{+*})$ requires m/z 208.1458; found m/z 208.1453.

Step 3.

The product of step 2 (2.5 g, 12 mmol) and tert-butyl dimethylchlorosilane (3.6 g, 24 mmol) were dissolved in DCM (120 mL). Triethylamine (5 mL, 36 mmol) was then added, and the reaction mixture was allowed to stir overnight. The solvent was removed under reduced pressure, and the crude product was purified by chromatography on a column of silica gel (2:8 EtOAc/hexanes) to afford the indicated product as a white solid (2.8 g, 73%).

$^1H$ NMR (500 MHz, $CDCl_3$, δ): 0.03 (s, 6H), 0.89 (s, 9H), 1.59 (s, 6H), 2.15 (t, J=6.76 Hz, 2H), 2.21 (s, 3H), 2.48 (s, 3H), 3.61 (t, J=6.77 Hz, 2H), 5.82 (s, 1H), 6.60 (d, J=7.63 Hz, 1H), 6.88 (d, J=7.57 Hz, 1H); $^{13}C$ NMR (125 MHz, $CDCl_3$, δ): 5.41, 16.43, 18.30, 25.62, 25.92, 32.27, 39.68, 44.91, 61.75, 122.88, 125.17, 127.79, 132.07, 135.53, 153.87; HRMS (ESI) calculated for $[C_{19}H_{34}O_2Si]^+$ (M+H$^+$) requires m/z 323.2401; found m/z 323.2394.

Step 4.

Boc-protected β-alanine (1.75 g, 9.3 mmol), EDC (2.3 g, 18.6 mmol), and DMAP (2.28 g, 18.6 mmol) were added to a flame-dried 250-mL round-bottom flask. The flask was evacuated and flushed with N$_2$ (g), and DCM (42 mL) was added. Compound 3 (2.0 g, 6.2 mmol) was dissolved in dry DCM (20 mL), and the resulting solution was added dropwise. The reaction mixture was allowed to stir overnight. The reaction mixture was diluted with 10% w/v aqueous NaHCO$_3$ and then washed with 1 N HCl. The solution was dried over NaSO$_4$ (s), and solvent was removed under reduced pressure. The crude product was purified by chromatography on a column of silica gel (1:9 EtOAc/hexanes) to afford the indicated product as a white solid (1.98 g, 65%).

$^1$H NMR (500 MHz, CDCl$_3$, δ): 0.03 (s, 6H), 0.84 (s, 9H), 1.49-1.44 (m, 18H) 2.02 (s, 3H), 2.09-2.08 (m, 2H), 2.53 (s, 3H); 3.48-3.44 (m, 4H), 5.15-5.12 (bs, 1H), 6.92 (d, J=7.71 Hz, 1H), 6.96 (d, J=7.64 Hz, 1H); $^{13}$C NMR (125 MHz, CDCl$_3$, δ): 5.36, 17.21, 18.24, 25.26, 25.92, 28.38, 31.88, 34.87, 35.94, 39.40, 46.06, 60.72, 79.39, 128.46, 128.95, 131.26, 136.34, 137.29, 148.57, 155.85, 171.28; HRMS (ESI) calculated for $[C_{27}H_{47}NO_5Si]^+$ (M+H$^+$) requires m/z=494.3297; found m/z=494.3294.

Step 5.

The product of step 4 (1.5 g, 3.0 mmol) was dissolved in a mixture of THF (6 mL), H$_2$O (6 mL), and concentrated glacial acetic acid (18 mL). The reaction mixture was stirred and reaction progress was monitored with TLC. After 2 h, solvent was removed under reduced pressure, and the crude product was purified by passage through a short (2-in) plug of silica gel (2:8 EtOAc/hexanes) to afford the indicated product as a colorless oil (1.34 g, quant).

$^1$H NMR (500 MHz, CDCl$_3$, δ): 1.43 (s, 9H), 1.46 (s, 3H), 1.51 (s, 3H), 1.93-1.89 (m, 2H), 2.02 (s, 3H), 2.53 (s, 3H), 2.84-2.82 (m, 2H) 3.57-3.45 (m, 4H), 5.20 (bs, 1H), 6.92-6.91 (d, J=7.70 Hz, 1H), 6.97-6.95 (d, J=7.73 Hz, 1H); $^{13}$C NMR (125 MHz, CDCl$_3$, δ): 17.22, 25.39, 28.41, 32.20, 34.94, 35.93, 39.50, 45.77, 60.38, 79.54, 128.65, 129.14, 131.43, 136.47, 137.09, 148.58, 155.86, 171.78; HRMS (ESI) calculated for $[C_{21}H_{33}NO_5]^+$ (M+H$^+$) requires m/z 380.2432; found m/z 380.2437.

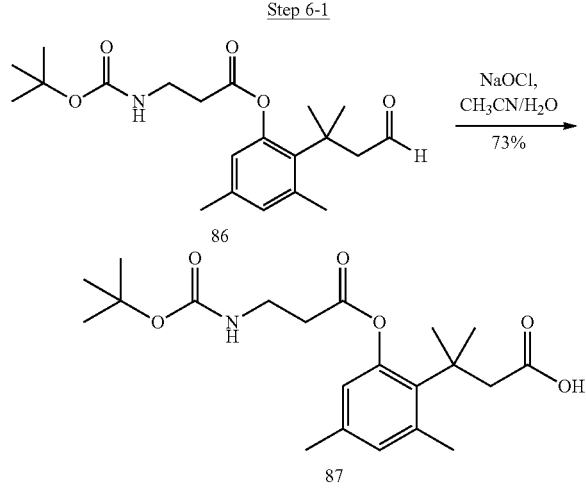

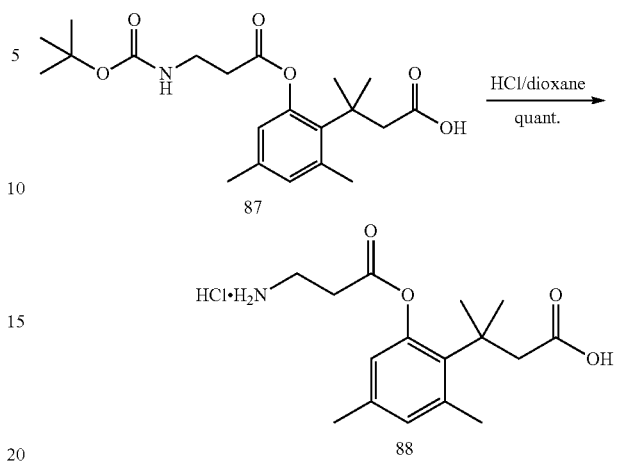

Step 6 (1 and 2).

A solution of the product of step 5 (1.0 g, 2.6 mmol) in anhydrous DCM (5 mL) was added slowly to a suspension of PCC (2.2 g, 10.4 mmol) in DCM (21 mL), and the reaction mixture was allowed to stir overnight. The reaction mixture was then filtered, and solvent was removed under reduced pressure. The crude product was purified by chromatography on a column of silica gel (4:6 EtOAc/hexanes) to afford the indicated product 87 as a clear oil (0.83 g, 85%).

$^1$H NMR (500 MHz, CDCl$_3$, δ): 1.52-1.44 (s, 16H), 2.04 (s, 3H), 2.55 (s, 3H), 2.93-2.55 (m, 4H), 3.51-3.48 (s, 2H), 5.08 (t, J=6.40 Hz, 1H), 6.97 (d, J=7.72 Hz, 1H), 7.02 (d, J=7.73 Hz, 1H), 9.51 (t, J=2.63 Hz, 1H); $^{13}$C NMR (125 MHz, CDCl$_3$, δ): 17.18, 25.35, 28.37, 34.88, 35.90, 38.42, 56.70, 79.50, 129.23, 129.42, 131.70, 135.78, 135.91, 148.21, 155.80, 171.20, 202.81; HRMS (ESI) calculated for $[C_{21}H_{31}NO_5]^+$ (M+H$^+$) requires m/z 378.2275; found m/z 378.2280.

The product of step 6-1 (0.8 g, 2.1 mmol) and NaH$_2$PO$_4$ (0.26 g, 1.59 mmol) were dissolved in CH$_3$CN (10 mL), and the resulting solution was cooled to −10° C. A solution of 80% w/v sodium chlorite (0.6 g, 6.3 mmol) in water (10 mL) was added dropwise. The reaction mixture was stirred for 1 h at −10° C. and then allowed to warm to room temperature. Saturated sodium sulfite solution (2 mL) was added, and the reaction mixture was acidified to pH 2.0 with 1 N HCl followed by extraction with ethyl acetate (3×15 mL). The organic layer was washed with brine and then dried over NaSO$_4$ (s). The solvent was removed under reduced pressure, and the crude product was purified by chromatography on a column of silica gel (5-10% v/v MeOH/DCM) to afford the indicated product as a clear oil (0.61 g, 73%)

$^1$H NMR (500 MHz, CDCl$_3$, δ): 1.43 (s, 9H), 1.54 (s, 3H), 1.63 (s, 3H), 2.02 (s, 3H), 2.55 (s, 3H), 2.85-2.74 (m, 4H), 3.48 (s, 2H), 5.16 (t, J=6.14 Hz, 1H), 6.93 (d, J 7.76 Hz, 1H), 6.98, (d, J=7.78 Hz, 1H); $^{13}$C NMR (125 MHz, CDCl$_3$, δ): 17.19, 25.23, 28.36, 31.23, 31.55, 34.87, 35.92, 39.00, 47.48, 79.50, 128.82, 131.44, 136.04, 136.69, 148.26, 155.89, 171.27, 175.98; HRMS (ESI) calculated for $[C_{21}H_{31}NO_6]^+$ (M+H$^+$) requires m/z 394.2225; found m/z 394.2219.

Step 7.

The product of step 6-2 (0.5 g, 1.2 mmol) was dissolved in a solution of 4 M HCl in dioxane (8.4 mL) and allowed to stir for 1 h. N$_2$ (g) was then bubbled though the solution for 15 min to remove excess HCl, and solvent was removed under reduced pressure. Diethyl ether was added to precipitate the indicated product compound 88 as its HCl salt (0.4 g; quant).

$^1$H NMR (500 MHz, CD$_3$OD, δ): 1.54 (s, 6H), 2.18 (s, 3H), 2.53 (s, 3H), 2.77 (s, 2H). 2.99-3.01 (t, J=6.52 Hz, 2H), 3.25-3.28 (m, 6H), 6.65 (s, 1H), 6.83 (s, 1H); $^{13}$C NMR (125 MHz, CD$_3$OD, δ): 20.22, 25.50, 32.09, 33.08, 36.21, 39.80, 124.01, 133.41, 134.86, 137.33, 139.54, 150.55, 171.46, 175.54; HRMS (ESI) calculated for [C$_{16}$H$_{24}$NO$_4$]$^+$ (M-Cl)$^+$ requires m/z 294.1779; found m/z 294.1793.

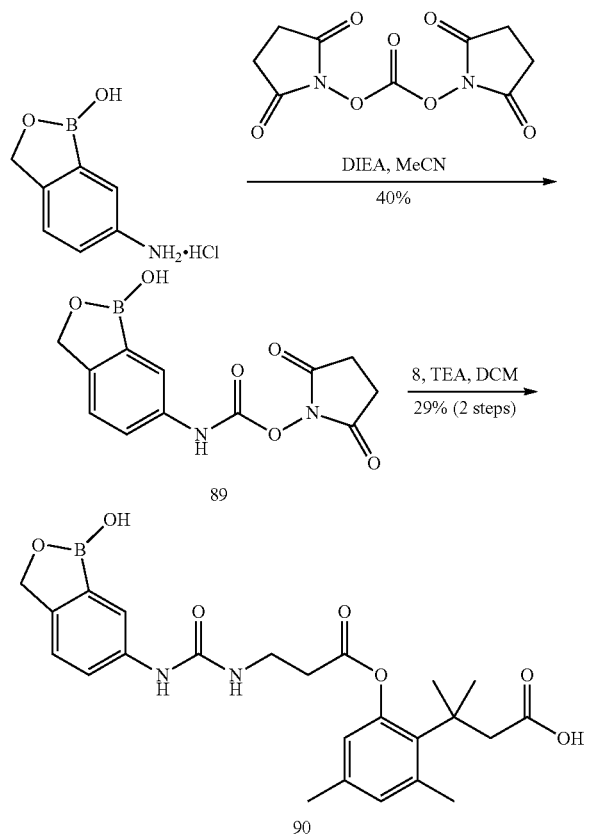

Step 8.

5-Amino-2-hydroxymethylphenylboronic acid (0.200 g, 1.07 mmol) was dissolved in 10.4 mL of dry acetonitrile. N,N-Disuccinimidyl carbonate (0.303 g, 1.18 mmol) was then added to the solution, followed by the dropwise addition of DIEA (0.20 mL, 2.14 mmol). The reaction mixture was allowed to stir overnight. The reaction mixture was then filtered to remove the insoluble N-hydroxysuccinimide (NHS) byproduct. The solvent from the filtrate was removed under reduced pressure to give the crude product as a yellow solid. The crude solid was dissolved in chloroform and cooled to −20° C. in the freezer for 1 h. The solution was filtered, and solvent was removed under reduced pressure to give compound 89 as a light yellow solid. The compound was used without further purification.

Compound 88 (0.080 g, 0.244 mmol) was dissolved in dry THF (2.4 mL). Compound 89 (0.078 g, 0.268 mmol) was then added to the solution, followed by the dropwise addition of DIEA (0.06 mL, 0.73 mmol). The reaction mixture was allowed to stir overnight. The reaction mixture was then filtered, and solvent was removed under reduced pressure. The crude product was purified by chromatography on a column of silica gel (3-5% v/v MeOH:DCM) to afford the indicated product compound 90 as a white solid (0.083 g, 73%).

$^1$H NMR (500 MHz, CD$_3$OD, δ): 1.56 (s, 3H), 2.20 (s, 3H), 2.55 (s, 3H), 2.80 (s, 2H), 2.87-2.85 (t, J=6.16 Hz, 2H), 3.60-3.67 (t, J=6.18 Hz, 2H), 5.03 (s, 2H), 6.63 (s, 2H), 6.68 (s, 1H), 7.28-7.29 (d, J=8.22 Hz, 1H), 7.50-7.52 (d, J=8.24 Hz, 1H), 7.62 (s, 1H); $^{13}$C NMR (125 MHz, CD$_3$OD, δ): 18.66, 24.00, 24.73, 30.45, 35.16, 38.22, 70.56, 119.96, 120.95, 122.28, 122.62, 131.62, 133.49, 135.96, 137.84, 138.42, 147.83, 149.29, 156.70, 171.60, 173.36, 174.05; note: the signal for the carbon attached to boron was not observable due to quadrupolar relaxation; HRMS (ESI) calculated for the methyl boronic ester [C$_{25}$H$_{31}$$^{11}$BN$_2$O$_7$]$^+$ (M+H)$^+$ requires m/z 483.2298; found m/z 483.2308.

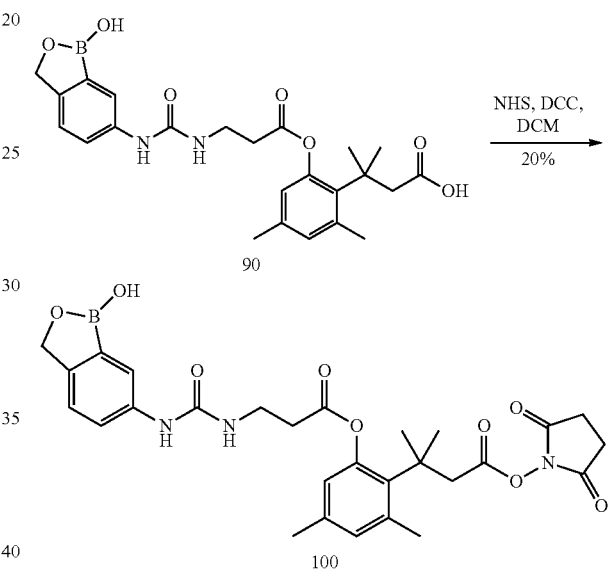

Step 9.

Compound 10 (0.068 g, 0.129 mmol) was dissolved in dry DCM (1.3 mL). The reaction mixture was then cooled to 0° C. and DCC (0.032 g, 0.155 mmol) followed by N-hydroxysuccinimide (0.016 g, 0.142 mmol) were added. The reaction mixture was allowed to warm to room temperature and stir over night. The reaction mixture was then cooled to 0° C. and the solid was removed by filtration. The solvent was removed under reduced pressure and the resulting residue and dissolved in ethyl acetate and chilled to −20° C. in a freezer for 3 h. The solids were removed by filtration, and the filtrate was extracted with water to remove any residual urea byproduct. The organic layers were combined, and the solvent was removed under reduced pressure to afford the compound 100 as a white solid (0.012 g, 20%).

$^1$H NMR (500 MHz, CD$_3$OD, δ): 1.61 (s, 6H), 2.20 (s, 3H), 2.55 (s, 3H), 2.75 (s, 4H), 2.93-2.90 (t, J=5.76 Hz, 2H), 3.15 (s, 2H), 3.61-3.58 (t, J=6.74 Hz, 2H), 5.03 (s, 2H), 6.66 (s, 1H), 6.84 (s, 1H), 7.28-7.29 (d, J=8.21 Hz, 1H), 7.51-7.49 (d, J=8.19 Hz, 1H), 7.61 (s, 1H); $^{13}$C NMR (125 MHz, CD$_3$OD, δ): 20.24, 25.50, 26.45, 31.56, 36.54, 36.72, 40.04, 45.15, 72.11, 121.51, 122.51, 123.84, 124.29, 133.32m 133.95, 137.71, 139.17, 139.99, 149.38, 150.86, 158.22, 168.16, 171.79, 173.13; note: the signal for the carbon attached to boron was not observable due to quadrupolar relaxation; HRMS (ESI) calculated for the methyl boronic ester $[C_{29}H_{34}{}^{10}BN_3O_9]^+$ $(M+Na)^+$ requires m/z 602.2286; found m/z 602.2290.

REFERENCES

[1] a) S. D. Patil, D. G. Rhodes, D. J. Burgess, *AAPS J.* 2005, 7, E61-77; b) D. K. Malik, S. Baboota, A. Ahuja, S. Hasan, J. Ali, *Curr. Drug Deliv.* 2007, 4, 141-151; c) M. S. Shim, Y. J. Kwon, *FEBS J.* 2010, 277, 4814-4827; d) Fu, A., Tang, R., Hardie, J., Farkas, M. E., and Rotello, V. M. (2014) Promises and pitfalls of intracellular delivery of proteins. Bioconjug. Chem. 25, 1602-1608; e) Onoue, S., Yamada, S., and Chan, H. K. (2014) Nanodrugs: Pharmacokinetics and safety. Int. J. Nanomed. 9, 1025-1037.

[2] a) Y. Gao, G. Gao, Y. He, T. Liu, R. Qi, *Mini Rev. Med. Chem.* 2008, 8, 889-900; b) M. Rapoport, H. Lorberboum-Galski, *Expert Opin. Drug Deliv.* 2009, 6, 453-463; c) X. Sun, N. Zhang, *Mini Rev. Med. Chem.* 2010, 10, 108-125; d) N. Schmidt, A. Mishra, G. H. Lai, G. C. Wong, *FEBS Lett.* 2010, 584, 1806-1813.

[3] a) X. Zhao, H. Li, R. J. Lee, *Expert Opin. Drug Deliv.* 2008, 5, 309-319; b) S. S. Rizk, A. Luchniak, S. Uysal, C. M. Brawley, R. S. Rock, A. A. Kossiakoff, *Proc. Natl. Acad. Sci. USA* 2009, 106, 11011-11015; c) C. Mohanty, M. Das, J. R. Kanwar, S. K. Sahoo, *Curr. Drug Deliv.* 2011, 8, 45-58.

[4] A. Varki, R. D. Cummings, J. D. Esko, H. H. Freeze, P. Stanley, C. R. Bertozzi, G. W. Hart, *Essentials of Glycobiology*, 2nd edition, Cold Spring Harbor Laboratory Press, New York, 2009.

[5] M. Ishiguro, T. Hisako, R. Sakakibara, J. Yamaguchi, Y. Aso, *J. Fac. Agric. Kyushu Univ.* 2002, 46, 367-379.

[6] T. D. James, M. D. Phillips, S. Shinkai, *Boronic Acids in Saccharide Recognition*, Royal Society of Chemistry, Cambridge, UK, 2006.

[7] a) Y. R. Vandenburg, Z. Y. Zhang, D. J. Fishkind, B. D. Smith, *Chem. Commun.* 2000, 149-150; b) W. Yang, H. Fan, X. Gao, S. Gao, V. V. Karnati, W. Ni, W. B. Hooks, J. Carson, B. Weston, B. Wang, *Chem. Biol.* 2004, 11, 439-448; c) R. Polsky, J. C. Harper, D. R. Wheeler, D. C. Arango, S. M. Brozik, *Angew. Chem. Int. Ed.* 2008, 120, 2671-2674; d) A. Matsumoto, N. Sato, K. Kataoka, Y. Miyahara, *J. Am. Chem. Soc.* 2009, 131, 12022-12023; e) X. Zhong, H. J. Bai, J. J. Xu, H. Y. Chen, Y. H. Zhu, *Adv. Funct. Mater.* 2010, 20, 992-999; f) A. Matsumoto, H. Cabral, N. Sato, K. Kataoka, Y. Miyahara, *Angew. Chem. Int. Ed.* 2010, 49, 5494-5497.

[8] a) P. R. Westmark, B. D. Smith, *J. Pharm. Sci.* 1996, 85, 266-269; b) J. I. Jay, B. E. Lai, D. G. Myszka, A. Mahalingam, K. Langheinrich, D. F. Katz, P. F. Kiser, *Mol. Pharm.* 2009, 7, 116-129; c) R. F. Barth, *Appl. Radiat. Isot.* 2009, 67, S3-6; d) W. Wu, N. Mitra, E. C. Yan, S. Zhou, *ACS Nano* 2010, 4, 4831-4839; e) Q. Peng, F. Chen, Z. Zhong, R. Zhuo, *Chem. Commun.* 2010, 46, 5888-5890; f) A. Kumar, I. Hozo, K. Wheatley, B. Djulbegovic, *Am. J. Hematol.* 2011, 86, 18-24.

[9] a) G. D'Alessio, J. F. Riordan, Ed., *Ribonucleases: Structures and Functions*, Academic Press, New York, 1997; b) R. T. Raines, *Chem. Rev.* 1998, 98, 1045-1065; c) G. R. Marshall, J. A. Feng, D. J. Kuster, *Biopolymers* 2008, 90, 259-277; d) C. M. Cuchillo, M. V. Nogués, R. T. Raines, *Biochemistry* 2011, 50, xxx-xxx.

[10] a) P. A. Leland, R. T. Raines, *Chem. Biol.* 2001, 8, 405-413; b) J. Futami, T. Maeda, M. Kitazoe, E. Nukui, H. Tada, M. Seno, M. Kosaka, H. Yamada, *Biochemistry* 2001, 40, 7518-7524; c) J. Futami, K. Nukui, T. Maeda, M. Kosaka, H. Tada, M. Seno, H. Yamada, *J. Biochem. (Tokyo)* 2002, 132, 223-228; d) T. J. Rutkoski, E. L. Kurten, J. C. Mitchell, R. T. Raines, *J. Mol. Biol.* 2005, 354, 41-54; e) J. Futami, M. Kitazoe, T. Maeda, E. Nukui, M. Sakaguchi, J. Kosaka, M. Miyazaki, M. Kosaka, H. Tada, M. Seno, J. Sasaki, N. H. Huh, M. Namba, H. Yamada, *J. Biosci. Bioeng.* 2005, 99, 95-103; f) T. J. Rutkoski, R. T. Raines, *Curr. Pharm. Biotechnol.* 2008, 9, 185-189.

[11] D. H. Dube, C. R. Bertozzi, *Nat. Rev. Drug Discov.* 2005, 4, 477-488.

[12] a) G. Springsteen, B. Wang, *Tetrahedron* 2002, 58, 5291-5300; b) H. Otsuka, E. Uchimura, H. Koshino, T. Okano, K. Kataoka, *J. Am. Chem. Soc.* 2003, 125, 3493-3502; c) K. Djanashvili, L. Frullano, J. A. Peters, *Chem. Eur. J.* 2005, 11, 4010-4018.

[13] a) M. Dowlut, G. Dennis, *J. Am. Chem. Soc.* 2006, 128, 4226-4227; b) M. Bérubé, M. Dowlut, D. G. Hall, *J. Org. Chem.* 2008, 73, 6471-6479.

[14] A. Wlodawer, L. A. Svensson, L. Sjölin, G. L. Gilliland, *Biochemistry* 1988, 27, 2705-2717.

[15] F. Malisan, R. Testi, *IUBMB Life* 2005, 57, 477-482.

[16] S. L. Deutscher, N. Nuwayhid, P. Stanley, E. I. Briles, C. B. Hirschberg, *Cell* 1984, 39, 295-299.

[17] The lost activity is attributable, at least in part, to the modification of the carboxyl group of aspartic acid 121, which is known to contribute to catalysis (L. W. Schultz, D. J. Quirk, R. T. Raines, *Biochemistry* 1998, 37, 8886-8898).

[18] S. Mothana, J. M. Grassot, D. G. Hall, *Angew. Chem. Int. Ed.* 2010, 49, 2883-2887.

[19] The HOB of benzoboroxole has $pK_a$ 7.2 (ref 13b), preserving most of the anionicity of a carboxyl group at pH 7.4.

[20] a) D. Venturoli, B. Rippe, *Am. J. Physiol. Renal Physiol.* 2005, 288, F605; b) D. E. Owens, 3rd, N. A. Peppas, *Int. J. Pharm.* 2006, 307, 93-102.

[21] Y. F. Cheng, M. Y. Li, S. R. Wang, H. J. Peng, S. Reid, N. T. Ni, H. Fang, W. F. Xu, B. H. Wang, *Sci. China. Chem.* 2010, 53, 3-20.

[22] A. Pal, M. Bérubé, D. G. Hall, *Angew. Chem. Int. Ed.* 2010, 49, 1492-1495

[23] J. Yan, S. Jin, B. Wang, Tetrahedron Letters 2005, 46, 8503-8505.

[24] Barth, R. F., Coderre, J. A., Vicente, M. G. & Blue, T. E. Boron neutron capture therapy of cancer: current status and future prospects. Clin Cancer Res 11, 3987-4002, (2005).

[25] Westmark, P. R., Gardiner, S. J. & Smith, B. D. Selective Monosaccharide Transport through Lipid Bilayers Using Boronic Acid Carriers J. Am. Chem. Soc. 118:11093-11100 (1996).

[26] Ma, R., and Shi, L. (2014) Phenylboronic acid-based glucose-responsive polymeric nanoparticles: synthesis and applications in drug delivery. Polym. Chem. 5, 1503.

[27] Jia, H. Z., Zhu, J. Y., Wang, X. L., Cheng, H., Chen, G., Zhao, Y. F., Zeng, X., Feng, J., Zhang, X. Z., and Zhuo, R. X. (2014) A boronate-linked linear-hyperbranched polymeric nanovehicle for pH-dependent tumor-targeted drug delivery. Biomaterials 35, 5240-5249.

[28] Zhao, Y., B. G. Trewyn, I. I. Slowing, and Lin, V. S.-Y. (2009) Mesoporous silica nanoparticle-based double drug delivery system for glucose-responsive controlled release of Insulin and Cyclic AMP. J. Am. Chem. Soc. 131, 8398-8400.

[29] Wang, Y., Chai, Z., Ma, L., Shi, C., Shen, T., and Song, J. (2014) Fabrication of boronic acid-functionalized nanoparticles via boronic acid-diol complexation for drug delivery. RSC Adv. 4, 53877-53884.

[30] Wang, B., Chen, L., Sun, Y., Zhu, Y., Sun, Z., An, T., Li, Y., Lin, Y., Fan, D., and Wang, Q. (2015) Development of phenylboronic acid-functionalized nanoparticles for emodin delivery. J. Mater. Chem. B 3, 3840-3847.

[31] Cal, P. M., Frade, R. F., Chudasama, V., Cordeiro, C., Caddick, S., and Gois, P. M. (2014) Targeting cancer cells with folic acid-iminoboronate fluorescent conjugates. Chem. Comm. 50, 5261-5263.

[32] Li, Y., Xiao, W., Xiao, K., Berti, L., Luo, J., Tseng, H. P., Fung, G., and Lam, K. S. (2012) Well-defined, reversible boronate crosslinked nanocarriers for targeted drug delivery in response to acidic pH values and cis-diols. Angew. Chem. Int. Ed. 51, 2864-2869.

[33] Wang, J., Zhang, Z., Wang, X., Wu, W., and Jiang, X. (2013) Size- and pathotropism-driven targeting and washout-resistant effects of boronic acid-rich protein nanoparticles for liver cancer regression. J. Control. Release 168, 1-9.

[34] Wang, M., Sun, S., Neufeld, C. I., Perez-Ramirez, B., and Xu, Q. (2014) Reactive oxygen species-responsive protein modification and its intracellular delivery for targeted cancer therapy. Angew. Chem. Int. Ed.

[35] Liu, J., Detrembleur, C., Debuigne, A., De Pauw-Gillet, M.-C., Mornet, S., Vander Elst, L., Laurent, S., Duguet, E., and Jérôme, C. (2014) Glucose-, pH- and thermoresponsive nanogels crosslinked by functional superparamagnetic maghemite nanoparticles as innovative drug delivery systems. J. Mater. Chem. B 2, 1009.

[36] Zhao, Z., Yao, X., Zhang, Z., Chen, L., He, C., and Chen, X. (2014) Boronic acid shell-crosslinked dextran-b-PLA micelles for acid-responsive drug delivery. Macromol. Biosci. 14, 1609-1618.

[37] Yang, B., Lv, Y., Zhu, J. Y., Han, Y. T., Jia, H. Z., Chen, W. H., Feng, J., Zhang, X. Z., and Zhuo, R. X. (2014) A pH-responsive drug nanovehicle constructed by reversible attachment of cholesterol to PEGylated poly(L-lysine) via catechol-boronic acid ester formation. Acta. Biomater. 10, 3686-3695.

[38] Tomsho, J. W., Pal, A., Hall, D. G. & Benkovic S. J. Ring Structure and Aromatic Substituent Effects on the pKa of the Benzoxaborole Pharmacophore. ACS Med. Chem. Letts. 3(1):48-52 (2012) published on-line Oct. 19, 2011.

[39] Adamczyk-Wozniak, A.; Cyranski, M. K.; Zubrowska, A.; Sporzynski, A. Benzoxaboroles-Old compounds with new applications. J. Organomet. Chem. 2009, 694 (22), 3533-3541.

[40] Snyder, H. R.; Reedy, A. J.; Lennarz, W. J. Synthesis of Aromatic Boronic Acids—Aldehydo Boronic Acids and a Boronic Acid Analog of Tyrosine. J. Am. Chem. Soc. 1958, 80 (4), 835-838.

[41] a. Torssell, K. Arylboronic acids. A review. Svensk Kemisk Tidskrift 69:34-44 (1957); b. Torssell, K. Arylboronic acids I. Arkiv foer Kemi 10:473-482 (1957); c. Torssell, K. Arylboronic acids II. Arkiv foer Kemi 10:497-505 (1957); d. Torssell, K. Arylboronic acids III. Bromination of tolylboronic acids according to Wolf-Ziegler. Arkiv foer Kemi 10:507-511 (1957); e. Torssell, K. Arylboronic acids IV. Nitration of several arylboronic acids and characteristics of the boron-carbon bond. Arkiv foer Kemi 10:513-521 (1957); f. Torssell, K. Arylboronic acids. V. Effects of arylboronic acids on microorganisms and enzymes. Arkiv. Kemie 10:529-540 (1957); g. Torssell, K. Arylboronic acids. VII. Complex formation between phenylboronic acid and fructose. Arkiv foer Kemie 10:541-547 (1957).

[42] Chames, P. Van Regenmortel, M. Weiss, E. & Baty, D. Therapeutic antibodies: successes, limitations and hopes for the future. Br J Pharmacol. 2009 May; 157(2): 220-233.

[43] Maiese, K.; Chong, Z. Z.; Shang, Y. C.; Hou, J. L. Med. Res. Rev. 2009, 29, 395-418.

[44] Lavis et al. (2011) Chemical Science 2:521-530

[45] a. Levine and Raines (2012) Chemical Science 3(8): 2412-2420; b. Zheng, A.; Wang, W.; Zhang, H.; Wang, B. Tetrahedron (1999) 55, 4237-4254; c. Liao, Y.; Wang, B. Bioorg. Med. Chem. Lett. (1999) 9, 1795-1800; d. Gomes, P.; Vale, N.; Moreira, R. *Molecules* (2007), 12, 2484-2506; e. Simplicio, A. L.; Clancy, J. M.; Gilmer, J. F. *Molecules* 2008, 13, 519-547; f. Wang, W.; Camenisch, G.; Sane, D. C.; Zhang, H.; Hugger, E.; Wheeler, G. L.; Borchardt, R. T.; Wang, B. *J. Control. Release* 2000, 65, 245-251.

[46] M. H. Roehrl, J. Y. Wang, G. Wagner, Biochemistry 2004, 43, 16056-16066

[47] a. Offer and Dawson Org. Lett., 200, 2, 23-26; b. U.S. Pat. No. 6,972,320, c. U.S. Pat. No. 7,256,259; d. U.S. Pat. No. 7,317,129, e. Garcia, et al. Tetrahedron Lett. 1984, 25, 4841-4844; f. Malkinson, L. P.; Falconer, R. A; Toth, I. J. Org. Chem. 2000, 65, 5249-5252; g. Saxon, E.; Bertozzi, C. R. Science 2000, 287, 2007-2010.

[48] Martin-Belmonte, F.; Perez-Moreno, M. Nat. Rev. Cancer 2012, 12, 23-38.

[49] B. D. Smith, M. B. Soellner, R. T. Raines, J. Biol. Chem. 2003, 278, 20934-20938.

[50] B. R. Kelemen, T. A. Klink, M. A. Behlke, S. R. Eubanks, P. A. Leland, R. T. Raines, Nucleic Acids Res. 1999, 27, 3696-3701.

[51] P. A. Leland, L. W. Schultz, B. M. Kim, R. T. Raines, Proc. Natl. Acad. Sci. USA 1998, 95, 10407-10412.

[52] a. Crameri, A., Whitehorn, E. A., Tate, E., and Stemmer, W. P. C. (1996) Improved green fluorescent protein by molecular evolution Using DNA shuffling. Nat. Biotechnol. 14, 315-319; b. Patterson, G. H., Knobel, S. M., Sharif, W. D., Kain, S. R., and Piston, D. W. (1997) Use of the green fluorescent protein and its mutants in quantitative fluorescence microscopy. Biophys. J. 73, 2782-2790; c. Waldo, G. S., Standish, B. M., Berendzen, J., and Terwilliger, T. C. (1999) Rapid protein-folding assay using green fluorescent protein. Nat. Biotechnol. 17, 691-695; d. Cabantous, S., Terwilliger, T. C., and Waldo, G. S. (2005) Protein tagging and detection with engineered self-assembling fragments of green fluorescent protein. Nat. Biotechnol. 23, 102-107; e. Pedelacq, J.-D., Cabantous, S., Tran, T., Terwilliger, T. C., and Waldo, G. S. (2006) Engineering and characterization of a superfolder green fluorescent protein. Nat. Biotechnol. 24, 79-88.

[53] McGrath, N. A., Andersen, K. A., Davis, A. K. F., Lomax, J. E., and Raines, R. T. (2015) Diazo compounds for the bioreversible esterification of proteins. *Chem. Sci.* 6, 752-755.

[54] M. Sela, C. B. Anfinsen, W. F. Harrington, Biochim. Biophys. Acta 1957, 26, 502-512.]

We claim:

1. A boronation reagent of formula:

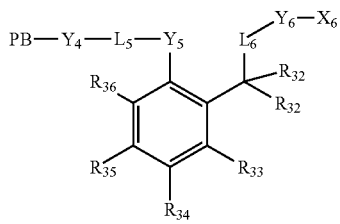

where:

PB is a phenylboronate group;

$Y_4$, $Y_5$ and $Y_6$ are independently selected from —O—, —S—, —NRc-, —CO—, —O—CO—, —CO—O—, —CO—NRc-, —NRc-CO—, —NRc-CO—NRc-, —OCO—NRc-, —NRc-CO—O—, —N=N—, —N=N—NRc-, —CO—S—, —S—CO—, —S—S—, —SO$_2$—, and —CRc(OH)—CRc(OH)—, where Rc is hydrogen or C1-C3 alkyl;

$L_5$ and $L_6$ are divalent spacer moieties;

$X_6$ is a leaving group and —$Y_6$—$X_6$ together is a reactive group;

$R_{33}$ and each $R_{32}$ are independently selected from a C1-C8 alkyl group or a C3-C8 cycloalkyl group;

$R_{34}$-$R_{36}$ are selected from the group consisting of hydrogen, a straight-chain or branched aliphatic group having 1-8 carbon atoms, a C3-C8 cycloalkyl group, an alicyclic group, an aryl group, a heterocyclic group, a heteroaryl group, a —CO$_2$R$_{10}$ group, a —O—CO—R$_{10}$ group, a —CON(R$_{12}$)$_2$ group, a —O—CON(R$_{12}$)$_2$ group; a —N(R$_{12}$)$_2$ group, a —OR$_{10}$ group, a —(CH$_2$)$_m$—OH group, a —(CH$_2$)$_m$—N(R$_{12}$)$_2$ group, a halogen, a nitro group, a cyano group, a —SO$_2$—OR$_{10}$ group, or $R_{36}$ together with $R_{35}$ or $R_{35}$ together with $R_{34}$ and the ring carbons to which $R_{34}$-$R_{36}$ are attached, form a 5-8-member alicyclic, heterocyclic, aryl or heteroaryl ring moiety, each of which groups or moieties is optionally substituted;

m is an integer from 1-8;

each $R_{10}$ is independently selected from hydrogen, a straight-chain or branched aliphatic group having 1-8 carbon atoms, an alicyclic group, an aryl group, a heterocyclic group, or a heteroaryl group, each of which groups is optionally substituted;

each $R_{12}$ is independently selected from hydrogen, a straight-chain or branched aliphatic group having 1-8 carbon atoms, an alicyclic group, an aryl group, a heterocyclic group, a heteroaryl group, or two $R_{12}$ together with the nitrogen to which they are attached form a 5-8 member heterocyclic or heteroaryl ring moiety, each of which groups or moieties is optionally substituted; and wherein optional substitution is substitution by one or more substituents selected from halogen, an oxo group, a nitro group, a cyano group, a C1-C6 alkyl group, a C1-C6 alkoxy group, a C2-C6 alkenyl group, a C2-C6 alkynyl group, a 3-7 member alicyclic ring, wherein one or two ring carbons of the alicyclic ring are optionally replaced with —CO— and which alicyclic ring optionally contains one or two double bonds, an aryl group having 6-14 carbon ring atoms, a 5- or 6-member ring heterocyclic group having 1-3 heteroatoms and wherein one or two ring carbons of the heterocyclic group are optionally replaced with —CO— and which heterocyclic group optionally contains one or two double bonds, a heteroaryl group having 1-3 heteroatoms, a —CO$_2$R$_{13}$ group, a —OCO—R$_{13}$ group, a —CON(R$_{14}$)$_2$ group, a —OCON(R$_{14}$)$_2$ group, a —N(R$_{14}$)$_2$ group, a —SO$_2$—OR$_{13}$ group, a —OR$_{13}$ group, a —(CH$_2$)$_m$—OR$_{13}$ group, a —(CH$_2$)$_m$—N(R$_{14}$)$_2$ group, where m is 1-8 and each $R_{13}$ or $R_{14}$ is independently hydrogen, an unsubstituted C1-C6 alkyl group, an unsubstituted aryl group having 6-14 carbon atoms, an unsubstituted 5- or 6-member ring heterocyclic group having 1-3 heteroatoms and wherein one or two ring carbons of the heterocyclic group are optionally replaced with —CO— and which heterocyclic group optionally contains one or two double bonds, and a heteroaryl group having 1-3 heteroatoms and wherein two $R_{14}$ together with the nitrogen to which they are attached optionally form a heterocyclic or heteroaryl ring moiety.

2. The reagent of claim 1 wherein $Y_6$—$X_6$ together is a reactive group that reacts with one or more of an amino group, a carboxylic acid group or ester thereof, a sulfhydryl group, a hydroxyl group, an azide group, a thioester group, a phosphinothioester group, an aldehyde group or a ketone group of an amino acid, peptide or protein.

3. The reagent of claim 1 wherein $Y_6$ is a —CO— and $X_6$ is a leaving group of an activated ester.

4. The reagent of claim 3 wherein $X_6$ is selected from the group consisting of a nitro-substituted phenolate group, a halogen-substituted phenolate group, an N-oxido-succinimidyl or an N-oxido-sulfosuccinimidyl group.

5. The reagent of claim 4 wherein $X_6$ is pentafluorophenolate, tetrafluorophenolate, p-nitrophenolate or p-sulfo-tetrafluorophenolate.

6. The reagent of claim 1 wherein $L_5$ and $L_6$ are selected from:

alkylene linkers (—(CH$_2$)$_y$—) wherein y is 1-12, and alkoxyalkyl linkers —[(CH$_2$)$_q$—O—(CH$_2$)$_r$]$_a$— wherein q and r are zero or integers from 1-4, one of q and r is not zero, and a is 1-6.

7. The reagent of claim 1 wherein $L_5$ is —(CH$_2$)$_2$— and $L_6$ is —CH$_2$—.

8. The reagent of claim 1 wherein $R_{33}$ and each $R_{32}$ are C1-C3 alkyl groups.

9. The reagent of claim 1 wherein $R_{33}$ and each $R_{32}$ are methyl groups.

10. The reagent of claim 1 wherein $R_{34}$-$R_{36}$ are selected from hydrogen, a C1-C8 alkyl group, a C3-C8 cycloalkyl group, a halogen, a nitro group, or a cyano group.

11. The reagent of claim 1 wherein $R_{34}$-$R_{36}$ are selected from hydrogen, a C1-C3 alkyl group, or a halogen.

12. The reagent of claim 1 wherein $Y_4$ is —NH—CO—NH—.

13. The reagent of claim 1 wherein $Y_5$ is —CO—O—.

14. The reagent of claim 1 wherein PB is selected from:

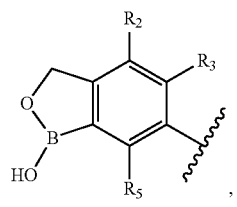

PB1

-continued

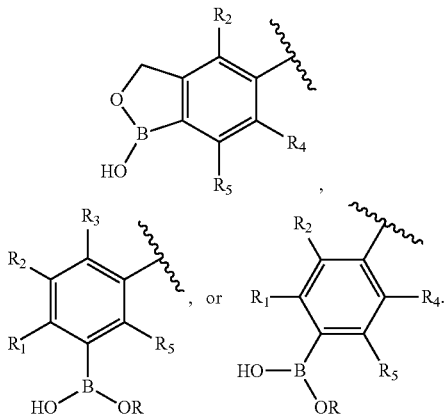

15. A method for reversibly boronating a cargo molecule having one or more amino groups which comprises reacting the cargo molecule with a reagent of claim 1 wherein $Y_6$—$X_6$ together is a reactive group that reacts with an amino group.

16. A method for delivering a cargo molecule into a cell which comprises boronating the cargo molecule by reacting the cargo molecule with a reagent of claim 1 and contacting the cell with the boronated cargo molecule.

17. The reagent of claim 1 wherein:
$Y_4$ is —NH—CO—NH—, $Y_5$ is —CO—O—, each $R_{32}$, $R_{33}$ and $R_{35}$ are methyl groups, and $R_{34}$ and $R_{36}$ are hydrogens.

18. The reagent of claim 17 wherein PB is selected from:

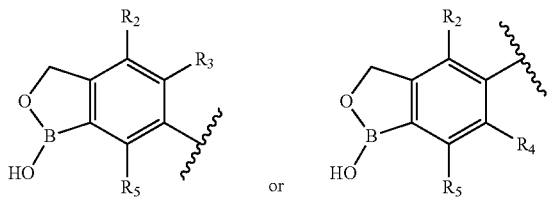

where $R_2$-$R_5$ are all hydrogens.

19. The reagent of claim 17 wherein $X_6$ is selected from an N-oxido-succinimidyl or an N-oxido-sulfosuccinimidyl group.

20. The reagent of claim 17 which is:

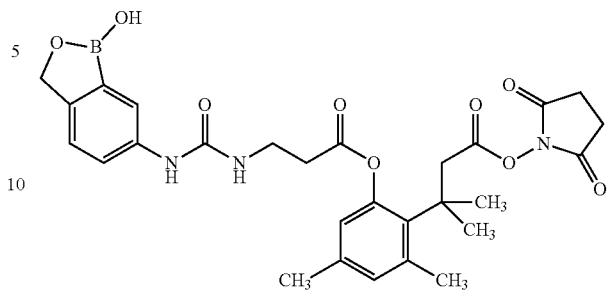

21. The reagent of claim 1 wherein optional substitution is substitution by one or more substituents selected from halogen, an oxo group; a nitro group, a cyano group, a C1-C6 alkyl group, a C1-C6 alkoxy group, a C2-C6 alkenyl group, a C2-C6 alkynyl group, a phenyl group, and a benzyl group.

22. The reagent of claim 21 wherein $Y_6$—$X_6$ together is a reactive group that reacts with an amine group.

23. The reagent of claim 1 wherein $Y_4$ and $Y_5$ are independently selected from —O—, —S—, —NRc-, —CO—, —O—CO—, —CO—O—, —CO—NRc-, —NRc-CO—, and —NRc-CO—NRc, where Rc is hydrogen or C1-C3 alkyl.

24. The reagent of claim 14 wherein:
each $R_{32}$, $R_{33}$ and $R_{35}$ are methyl groups, and $R_{34}$ and $R_{36}$ are hydrogens.

25. The reagent of claim 24 wherein $Y_6$—$X_6$ together is a reactive group that reacts with one or more of an amine group, a carboxylic acid group or ester thereof, a sulfhydryl group, a hydroxyl group, an azide group, a thioester group, a phosphinothioester group, an aldehyde group or a ketone group of an amino acid, peptide or protein.

26. The reagent of claim 25 wherein $L_5$ and $L_6$ are selected from:
alkylene linkers (—$(CH_2)_y$—) wherein y is 1-12.

27. The reagent of claim 26 wherein $Y_4$ and $Y_5$ are independently selected from —O—, —S—, —NRc-, —CO—, —O—CO—, —CO—O—, —CO—NRc-, —NRc-CO—, and —NRc-CO—NRc, where Rc is hydrogen or C1-C3 alkyl.

* * * * *